US012648928B2

(12) United States Patent
Nieuwdorp et al.

(10) Patent No.: US 12,648,928 B2
(45) Date of Patent: Jun. 9, 2026

(54) INTERVENTION STRATEGY FOR PREVENTION OR TREATMENT OF DIABETES MELLITUS, AUTOIMMUNE DISEASE, INFLAMMATORY DISEASE OR CARDIOVASCULAR DISEASE

(71) Applicants: ACADEMISCH MEDISCH CENTRUM, Amsterdam (NL); WAGENINGEN UNIVERSITEIT, Wageningen (NL)

(72) Inventors: Max Nieuwdorp, Amsterdam (NL); Willem Meindert De Vos, Amsterdam (NL)

(73) Assignees: ACADEMISCH MEDISCH CENTRUM, Amsterdam (NL); WAGENINGEN UNIVERSITEIT, Wageningen (NL)

( * ) Notice: Subject to any disclaimer, the term of this patent is extended or adjusted under 35 U.S.C. 154(b) by 817 days.

(21) Appl. No.: 17/905,133

(22) PCT Filed: Feb. 26, 2021

(86) PCT No.: PCT/EP2021/054924
§ 371 (c)(1),
(2) Date: Aug. 26, 2022

(87) PCT Pub. No.: WO2021/170848
PCT Pub. Date: Sep. 2, 2021

(65) Prior Publication Data
US 2023/0181531 A1 Jun. 15, 2023

(30) Foreign Application Priority Data

Feb. 28, 2020 (NL) ..................................... 2025020
Feb. 28, 2020 (NL) ..................................... 2025021
Feb. 28, 2020 (NL) ..................................... 2025022

(51) Int. Cl.
| | |
|---|---|
| A61K 31/405 | (2006.01) |
| A61K 9/48 | (2006.01) |
| A61K 35/745 | (2015.01) |
| A61K 35/747 | (2015.01) |
| A61P 3/08 | (2006.01) |

(52) U.S. Cl.
CPC .......... *A61K 31/405* (2013.01); *A61K 9/4833* (2013.01); *A61K 35/745* (2013.01); *A61K 35/747* (2013.01); *A61P 3/08* (2018.01)

(58) Field of Classification Search
CPC .. A61K 31/405; A61K 9/4833; A61K 35/745; A61K 35/747; A61K 31/685; A61K 35/74; A61K 45/06; A61P 3/08; A61P 3/10; A61P 9/00; A61P 37/00
See application file for complete search history.

(56) References Cited

U.S. PATENT DOCUMENTS 7,670,619 B2 * 3/2010 Mihaylov ............... A61P 25/24
514/415
2003/0225035 A1 12/2003 Harats et al.

FOREIGN PATENT DOCUMENTS

| | | |
|---|---|---|
| CN | 108785322 A | 11/2018 |
| WO | 2010/083368 A2 | 7/2010 |
| WO | 2017/072278 A1 | 5/2017 |
| WO | 2019/168401 A1 | 9/2019 |

OTHER PUBLICATIONS

Tin et al. (J Am Soc Nephrol 29: 1939-1947, 2018).*
Roager et al. (Nature Comm., (2018) 9:3294, 10 pages).*
Burrello et al. (Cells 2019, 8, 517, 18 pages).*
Guo et al. (BioMed Research International, 2013, 581631, 9 pages, 2013).*
Jimenez ("Bromotryptophan and its Analogs in Peptides from Marine Animals", Protein & Peptide Letters, vol. 26, Issue 4, 2019, pp. 251-260).*
Peters (Biochemical Pharmacology, vol. 20 (1971), pp. 1413-1420).*
International Search Report for International Application No. PCT/EP2021/054924, mailed Jul. 12, 2021, 7 pages.
International Written Opinion for International Application No. PCT/EP2021/054924, mailed Jul. 12, 2021, 12 pages.
Search Report and Written Opinion for the Netherlands Application No. NL 2025020, mailed Oct. 14, 2020, 8 pages.
Search Report and Written Opinion for the Netherlands Application No. NL 2025021, mailed Oct. 16, 2020, 10 pages.
Search Report and Written Opinion for the Netherlands Application No. NL 2025022, mailed Oct. 14, 2020, 9 pages.
Southam, et al. "Structural requirements of the competitive binding site of recombinant human indoleamine 2,3-dioxygenase" Medicinal Chemistry Research, vol. 6, Issue 5, Jan. 1, 1996, pp. 343-352 (Abstract Only).

(Continued)

*Primary Examiner* — Robert H Havlin
(74) *Attorney, Agent, or Firm* — TraskBritt

(57) ABSTRACT

An intervention strategy in the prevention or treatment of a subject having an inflammation-related disease such as Diabetes mellitus, autoimmune disease, inflammatory disease or cardiovascular disease. The intervention strategy preferably relates to administration of a chloro-, fluoro-, or bromo-substituted tryptophan, preferably 6-bromotryptophan, and/or a mono- or di-fatty acid substituted glycerol phosphocholine (GPC), preferably chosen from the group consisting of 1-myristoyl-2-arachidonoyl-glycero-phosphocholine (MA-GPC) and 1-arachidonoyl-glycero-phosphocholine (A-GPC), or any derivative or functional equivalent of these. Alternatively, the intervention relates to administration of a *Desulfovibrio* species, wherein the *Desulfovibrio* species is preferably chosen from the group consisting of *Desulfovibrio piger, Desulfovibrio fairfieldensis, Desulfovibrio desulfuricans, desulfovibrio* indonensis, *Desulfovibrio alaskensis, Desulfovibrio vulgaris, Desulfovibrio vietnamensis* and *Desulfovibrio gigas.*

3 Claims, 32 Drawing Sheets
Specification includes a Sequence Listing.

(56)                    References Cited

OTHER PUBLICATIONS

Stefanaki et al. "Examining the gut bacteriome, virome, and mycobiome in glucose metabolism disorders: Are we on the right track?" Metabolism Clinical and Experimental, Issue 73 (May 2017) pp. 52-66.

Yamamoto et al. "Effects of Various Phytochemicals on Indoleamine 2,3-Dioxygenase 1 Activity: Galanal Is a Novel, Competitive Inhibitor of the Enzyme" PLOS ONE, vol. 9, Issue 2 (Feb. 2014) 8 pages.

Chinese First Office Action for Chinese Application No. 202180014499.X, dated Mar. 8, 2024, 10 pages with English translation.

Pubill-Ulldemolins et al. "Heck Diversification of Indole-Based Substrates under Aqueous Conditions: From Indoles to Unprotected Halo-tryptophans and Halo-tryptophans in Natural Product Derivatives" Chem. Eur. J. 2019, vol. 25, pp. 10866-10875.

De Vos "Fame and future of faecal transplantations—developing next-generation therapies with synthetic microbiomes" Microb Biotechnol . Jul. 2013;6(4):316-25. doi: 10.1111/1751-7915.12047. Epub Apr. 10, 2013.

Ganju et al "Microbial community profiling shows dysbiosis in the lesional skin of Vitiligo subjects" Sci Rep 6, 18761 (Jan. 2016).

Henikoff et al "Amino acid substitution matrices from protein blocks" Proc Natl Acad Sci USA, Nov. 15, 1992;89(22):10915-9.

Japanese Notice of Reasons for Refusal for Japanese Application No. 2022-552221, dated Feb. 4, 2025, 13 pages with English translation.

Kolho et al. "Fecal Microbiota in Pediatric Inflammatory Bowel Disease and Its Relation to Inflammation" Am J Gastroenterol. Jun. 2015;110(6):921-30. doi: 10.1038/ajg.2015.149. Epub May 19, 2015.

Korpela et al "Intestinal microbiome is related to lifetime antibiotic use in Finnish pre-school children." Nature communications vol. 7 10410. Jan. 26, 2016, doi:10.1038/ncomms10410.

Marazuela et al. "Regulatory T cells in human autoimmune thyroid disease", J. Clin. Endocrinol. Metab. Sep. 2006; 91(9):3639-46 (Epub Jun. 27, 2006).

Rajilic-Stojanovic et al. "The first 1000 cultured species of the human gastrointestinal microbiota" FEMS Microbiology Reviews, vol. 38, Issue 5, Sep. 2014, pp. 996-1047,.

Saito et al. "4-Chloro-3-hydroxyanthranilate, 6-chlorotryptophan and norharmane attenuate quinolinic acid formation by interferon-y-stimulated monocytes (THP-i cells)" Biochem. J. (1993) 291, 11-14 (Printed in Great Britain) Accepted Jan. 28, 1993.

Tin et al. "Serum 6-Bromotryptophan Levels Identified as a Risk Factor for CKD Progression" J Am Soc Nephrol. May 18, 2018;29(7):1939-1947.

Verdu et al. "Common ground: shared risk factors for type 1 diabetes and celiac disease" Nature Immunology, vol. 19 (Jul. 2018) pp. 685-695.

Chen et al. "Isolation of *Desulfovibrio* spp. from human gut microbiota using a next-generation sequencing directed culture method" Letters in Applied Microbiology, vol. 68, Issue 6, pp. 553-561 (Mar. 5, 2019).

Cheng et al. "A nanoparticle-incorporated STING activator enhances antitumor immunity in PD-L1-insensitive models of triplenegative breast cancer" JCI Insight. 2018;3(22):e120638 (Nov. 15, 2018).

Chou et al. "Impact of intracellular innate immune receptors on immunometabolism" Springer Nature, Cellular & Molecular Immunology (2022) 19:337-351 (Oct. 25, 2021).

Serna-Cock et al. "Probiotic encapsulation" African Journal of Microbiology Research, vol. 7(40), pp. 4743-4753, Oct. 4, 2013.

Koh et al. "Microbially Produced Imidazole Propionate Impairs Insulin Signaling through mTORC1" Cell 175, 947-961 (Nov. 1, 2018).

Lachin et al. "Sample Size Requirements for Studies of Treatment Effects on Beta-Cell Function in Newly Diagnosed Type 1 Diabetes" Plos One, vol. 6, Issue 11, e26471(Nov. 2011).

* cited by examiner

RAW264.7 cells expressing NFκB luciferase reporter

SEQUENCE LISTING

```
<160> NUMBER OF SEQ ID NOS: 1

<210> SEQ ID NO 1
<211> LENGTH: 1542
<212> TYPE: DNA
<213> ORGANISM: Desulfovibrio piger

<400> SEQUENCE: 1
agagtttgat cctggctcag attgaacgct ggcggcgtgc ttaacacatg caagtcgtac      60
gcgaaaggga cttcggtccc gagtaaagtg gcgcacgggt gagtaacacg tggataatct     120
gcctctatga tggggataac agttggaaac gactgctaat accgaatacg ctcatgatga     180
actttgtgag gaaaggtggc ctctgcttgc aagctatcgc atagagatga gtccgcgtcc     240
cattagctag ttggtggggt aacggcctac caaggcaacg atgggtagcc gatctgagag     300
gatgatcggc cacactggaa ctgaaacacg gtccagactc ctacgggagg cagcagtggg     360
gaatattgcg caatgggcga aagcctgacg cagcgacgcc gcgtgaggga tgaaggtctt     420
cggatcgtaa acctctgtca gaagggaaga aactagggtg ttctaatcat catcctactg     480
acggtacctt caaaggaagc accggctaac tccgtgccag cagccgcggt aatacggagg     540
gtgcaagcgt taatcggaat cactgggcgt aaagcgcacg taggctgtta tgtaagtcag     600
gggtgaaagc ccacggctca accgtggaac tgcccttgat actgcacgac tcgaatccgg     660
gagagggtgg cggaattcca ggtgtaggag tgaaatccgt agatatctgg aggaacatca     720
gtggcgaagg cggccacctg gaccggtatt gacgctgagg tgcgaaagcg tggggagcaa     780
acaggattag ataccctggt agtccacgcc gtaaacgatg gatgctagat gtcgggatgt     840
atgtctcggt gtcgtagtta acgcgttaag catcccgcct ggggagtacg gtcgcaaggc     900
tgaaactcaa agaaattgac ggggcccgc acaagcggtg gagtatgtgg tttaattcga     960
tgcaacgcga agaaccttac ctaggtttga catctgggga accctcccga aaatgagggg    1020
tgcccttcgg ggagccccaa gacaggtgct gcatggctgt cgtcagctcg tgtcgtgaga    1080
tgttgggtta agtcccgcaa cgagcgcaac ccctatgcat agttgccagc aagtaaagtt    1140
gggcactcta tgcagactgc ccgggttaac cgggaggaag gtggggacga cgtcaagtca    1200
tcatggccct tacacctagg gctacacacg tactacaatg gcacgcacaa agggcagcga    1260
taccgtgagg tggagccaat cccaaaaaac gtgtcccagt ccggattgca gtctgcaact    1320
cgactgcatg aagtcggaat cgctagtaat tcgaggtcag catactcggg tgaatgcgtt    1380
```

-continued

```
cccgggcctt gtacacaccg cccgtcacac cacgaaagtc ggttttaccc gaagccggtg    1440
agccaactag caatagaggc agccgtctac ggtagggccg atgattgggg tgaagtcgta    1500
acaaggtagc cgtaggggaa cctgcggctg gatcacctcc tt                       1542
```

INTERVENTION STRATEGY FOR PREVENTION OR TREATMENT OF DIABETES MELLITUS, AUTOIMMUNE DISEASE, INFLAMMATORY DISEASE OR CARDIOVASCULAR DISEASE

CROSS-REFERENCE TO RELATED APPLICATIONS

This application is a national phase entry under 35 U.S.C. § 371 of International Patent Application PCT/EP2021/054924, filed Feb. 26, 2021, designating the United States of America and published as International Patent Publication WO 2021/170848 A1 on Sep. 2, 2021, which claims the benefit under Article 8 of the Patent Cooperation Treaty to Netherlands Patent Application Serial No. 2025020, filed Feb. 28, 2020, Netherlands Patent Application Serial No. 2025021, filed Feb. 28, 2020, and Netherlands Patent Application Serial No. 2025022, filed Feb. 28, 2020.

STATEMENT REGARDING ELECTRONIC FILING OF A SEQUENCE LISTING

Pursuant to 37 C.F.R. § 1.831-1.834, a Sequence Listing text file entitled "2022-08-26-Sequence Listing-P16978US," 2,378 bytes in size, generated Aug. 26, 2022, has been submitted for this application, the contents of which are hereby incorporated by reference.

TECHNICAL FIELD

The disclosure relates to the prevention and/or treatment of an inflammation-related disease chosen from the group consisting of Diabetes mellitus, autoimmune disease, inflammatory disease and cardiovascular disease, more specifically the use of compositions comprising specific microorganisms and/or metabolites thereof in the prevention and/or treatment.

BACKGROUND

The role of inflammation in both type 1 and type 2 Diabetes mellitus has generated increasing interest in targeting inflammation in order to improve prevention and treatment of the disease. Evidence has shown that inflammatory pathways are the principal mediators in the pathology of diabetes under the stimulus of risk factors including obesity or being overweight.

Also, the relationship between diabetes and cardiovascular disease is well established, with the risk for cardiovascular disease being significantly elevated in patients with diabetes. Atherosclerosis represents the most common cause of coronary artery disease, and the characterization of the disease as a chronic low-grade inflammatory condition is now largely accepted.

In addition, the classic sign of autoimmune diseases is also inflammation. The diseases may have flare-ups, i.e., when they get worse, and remissions, i.e., when symptoms get better or disappear. Treatment of autoimmune diseases depends on the type of disease, but in most cases one important goal is to reduce inflammation.

The current therapeutics for Diabetes, cardiovascular diseases, autoimmune diseases and inflammatory diseases have anti-inflammatory properties in addition to their major modes of action. Non-pharmacological treatments, such as lifestyle interventions reduce inflammation status, for examples assessed as circulating C-reactive protein (CRP)

and Interleukin-6 (IL-6) concentrations, and improve cardiovascular and all-cause mortality.

This makes therapeutic approaches that target inflammation an attractive area for research.

Novel therapeutic strategies are needed to improve quality of life in patients with inflammation related disorders including Diabetes mellitus, autoimmune disease, inflammatory disease, and cardiovascular disease. There remains a need to develop a new or improved prevention and/or treatment strategy.

BRIEF SUMMARY

It was investigated whether administration of fecal transplants, from either allogenic (healthy donor) or autologous (own) sources, may have beneficial effects in patients with autoimmune disease. Confirming earlier studies, it was found that administration of autologous fecal transplants can bring about an immune reset within patients with autoimmune disease, and thereby reduction of the severity of the autoimmune disease.

It was surprisingly found that the beneficial effects could be traced back to specific constituents in the fecal matter. These constituents with therapeutic application were found to relate most specifically to

- bacteria of the genus *Desulfovibrio*, preferably chosen from the group consisting of *Desulfovibrio piger, Desulfovibrio fairfieldensis, Desulfovibrio desulfuricans, desulfovibrio* indonensis, *Desulfovibrio alaskensis, Desulfovibrio vulgaris, Desulfovibrio vietnamensis* and *Desulfovibrio gigas*, most preferably *Desulfovibrio piger*. and
- the metabolites 6-bromotryptophan, 1-myristoyl-2-arachidonoyl-glycero-phosphocholine (MA-GPC) and 1-arachidonoyl-glycero-phosphocholine (A-GPC), or, more generally, chloro, fluoro or bromo-substituted tryptophans, or mono- or di-fatty acid substituted glycerol phosphocholines, or any derivative or functional equivalent of these.

Upon further research, it was surprisingly found that *Desulfovibrio* species and/or metabolites according to the disclosure, in particular, 6-bromotryptophan, have an anti-inflammatory effect, i.e., reduce inflammation status and reduce inflammation markers e.g., related to type 1 and type 2 Diabetes mellitus, autoimmune disease, cardiovascular disease, and inflammatory disease such as Systemic Inflammatory Response Syndrome (SIRS) or sepsis.

Further, an inverse relationship was found between plasma 6-bromotryptophan levels and presence of type 2 Diabetes mellitus. This suggests that *Desulfovibrio* species and/or metabolites according to the disclosure, in particular, 6-bromotryptophan, may contribute to the prevention of type 2 Diabetes mellitus and may contribute to the prevention or treat (microvascular and macrovascular) cardiovascular complications. Further, it was found that *Desulfovibrio* species and/or metabolites according to the disclosure, in particular, 6-bromotryptophan, may promote insulin secretion by beta cells.

Mechanistically, it is shown that the biological actions of 6-BT appear distinct from the ones of tryptophan. 6-BT does not act through activation of AhR, but it does inhibit NFkB activation and enhance mitochondrial metabolism. The latter is typically used by cells harboring an anti-inflammatory phenotype. Because of its broad effects on multiple cell types, its inhibitory action on NFkB signaling and its promotion of mitochondrial metabolism and fitness, 6-BT can be a very useful therapeutic not only in the context of type 1 and type 2 diabetes but also in many other inflammation related disorders such as sepsis, Systemic Inflammatory Response Syndrome (SIRS), and cardiovascular diseases.

In addition, without being bound by any theory, it is considered that the *Desulfovibrio* species and the metabolites according to the disclosure may modulate the immune system, e.g., by resetting B-cell clone function and regulatory T-cells, which in turn may inhibit autoimmune response.

It is thought that during early life, the immune system is trained via continuous crosstalk with a developing intestinal microbiome composition. In this way, the intestinal microbiome plays an essential role in modulating adaptive immune cell development, composition, and function (see e.g., Agace and McCoy, Immunity 46, Apr. 18, 2017). It is this process, amongst others, that leads to a proper functioning immune system, devoid of autoimmune factors.

However, the crosstalk between the immune system and the intestinal microbiome, or the end result thereof, may be disturbed, which can lead to the production of autoimmune antibodies (by B cells) and formation of autoreactive T cells. The treatment according to the disclosure may overcome this disturbance, by re-initiating the crosstalk between the immune system and the intestinal microbiome (including its specific bacteria, and/or derived products such as metabolites) and resulting in inhibition of the auto-immune response.

Accordingly, the use of the above-mentioned *Desulfovibrio* species and/or metabolites in autoimmune diseases, may stop the autoimmune destruction of targeted tissue and re-establish immune tolerance. The disclosure can achieve this by stimulating the immune system, wherein the *Desulfovibrio* species and/or metabolites are preferably administered to the duodenum (directly or indirectly such as via oral administration). The disclosure preferably does not aim to alter the intestinal microbiome, i.e., the gut microbiota composition.

WO2019168401 discloses the use of fecal matter in the prevention and treatment of autoimmune disease, wherein the fecal matter is autologous to the subject, and preferably administered to the small intestine, preferably the duodenum, where it can initiate an immune reset and thereby reduce severity of the autoimmune disease. However, there is room for improvement in the therapeutic efficacy of the method of WO2019168401, and its treatment is laborious and difficult to upscale.

Hence, the disclosure is aimed at the prevention or treatment of inflammation-related diseases chosen from the group consisting of:

type 1 diabetes mellitus;

type 2 diabetes mellitus;

cardiovascular diseases, particularly coronary artery disease (also known as coronary heart disease and ischemic heart disease), peripheral arterial disease, cerebrovascular disease (for example, stroke or TIA, Transient Ischemic Attack), atherosclerosis, stenosis, renal artery stenosis, aortic disease, aortic aneurysm, cardiomyopathy, hypertensive heart disease, hypertension, heart failure, pulmonary heart disease, cardiac dysrhythmias, cardiovascular inflammation, inflammatory heart disease, endocarditis, inflammatory cardiomegaly, myocarditis, eosinophilic myocarditis, valvular heart disease, congenital heart disease, or rheumatic heart disease;

inflammatory disease, in particular, cardiovascular inflammation, for example, carditis, endocarditis, myocarditis, pericarditis, vasculitis, arteritis, phlebitis, or capillaritis, or for example inflammation of the gastrointestinal tract, e.g., esophagitis, gastritis, gastroenteritis, enteritis, colitis, enterocolitis, duodenitis, ileitis, caecitis, appendicitis, or proctitis. Inflammatory diseases further include hepatic inflammation, pulmonary inflammation, skeletal inflammation, Systemic Inflammatory Response Syndrome (SIRS), sepsis; and autoimmune diseases, particularly (endocrine) autoimmune diseases (e.g., Hashimoto hypothyroidism, Graves hyperthyroidism, Rheumatoid arthritis, Celiac disease, Asthma/COPD, Addison's disease, IBD (Crohn and colitis ulcerosa)), Systemic lupus erythematosus, Vasculitis, Guillain Barre and CIDP, Multiple sclerosis, Psoriasis (arthritis), Vitiligo, and Bechterew's disease.

Additionally or alternatively, the use according to the disclosure may be for improving general health and/or reducing inflammation status.

The disclosure thus also encompasses prevention of the recited diseases, i.e., type 1 or type 2 diabetes mellitus, cardiovascular disease, inflammatory disease or autoimmune disease. Accordingly, the said *Desulfovibrio* species and/or metabolites according to the disclosure can be administered to a subject in order to avoid onset of any of the diseases, for example, in subjects wherein risk markers associated with pre-stage or early stage of the respective disease have been detected (before diagnosis of the respective disease). Such primary or secondary prevention strategy may prevent the development of the disease.

Some of the autoimmune diseases as referred herein are currently treated with immune therapy, such as by using antibodies to TNFα. However, these expensive immune therapies may only be successful in a subset of patients. This has been ascribed to deviations in the intestinal microbiota (Kolho et al., 2015 Am. J. Gastroenterol. 110(6):921-30). It is envisaged that treatment with a TNFα antagonist or anti-TNFα may be synergistic with treatment according to the disclosure, e.g., administration of the *Desulfovibrio* species and/or metabolites according to the disclosure.

The disclosure relates to the prevention or treatment of inflammation-related diseases chosen from the group consisting of type 1 or type 2 Diabetes mellitus, autoimmune disease, cardiovascular disease and inflammatory disease, by using one or more agent(s) chosen from the group consisting of:

*Desulfovibrio* species, preferably chosen from the group consisting of *Desulfovibrio piger, Desulfovibrio fairfieldensis, Desulfovibrio desulfuricans, desulfovibrio indonensis, Desulfovibrio alaskensis, Desulfovibrio vulgaris, Desulfovibrio vietnamensis* and *Desulfovibrio gigas*, most preferably *Desulfovibrio piger*; and the compounds (metabolites) 6-bromotryptophan, 1-myristoyl-2-arachidonoyl-glycero-phosphocholine (MA-GPC) and 1-arachidonoyl-glycero-phosphocholine (A-GPC), or, more generally, chloro, fluoro or bromo-substituted tryptophans, or mono- or di-fatty acid substituted glycerol phosphocholines, or any derivative or functional equivalent thereof.

Accordingly, the disclosure provides for a method of prevention or treatment of a subject in need thereof, particularly a subject having an inflammation-related disease, e.g., type 1 or type 2 Diabetes mellitus, autoimmune disease (such as an endocrine autoimmune disease), cardiovascular disease or inflammatory disease, comprising the step of administrating one or more of the above-mentioned agent(s).

In comparison to administration of autologous fecal matter, as described in WO2019168401, it was found that the method according to the disclosure has improved therapeutic efficacy in autoimmune disease, is less laborious, easier to administer, easier to produce e.g., under certified Quality Management Systems (QMS) or under Good Manufacturing Practice (GMP), and/or easier to upscale.

The disclosure, at least a priori, preferably does not aim to alter the intestinal microbiome, i.e., the gut microbiota composition or particularly the colon microbiota composition.

In the context of the disclosure, the autoimmune disease can be any autoimmune disease, including systemic and localized (organ specific) autoimmune diseases, particularly an autoimmune disease chosen from the group consisting of endocrine autoimmune disease (e.g., Type 1 Diabetes mellitus, Hashimoto's disease, Graves's disease, or Addison's disease); skin autoimmune disease (e.g., Psoriasis or Vitiligo); rheumatoid autoimmune diseases (e.g., rheumatoid arthritis, Systemic lupus erythematosus, Vasculitis or Bechterew's disease), and gastrointestinal autoimmune disease (e.g., Celiac disease, Inflammatory Bowel Disease), Neurological diseases (Guillain Barre, CIDP and Multiple sclerosis) and Lung diseases (COPD/Asthma).

In the context of the disclosure, the cardiovascular disease can be any cardiovascular disease, for example, coronary artery disease (also known as coronary heart disease and ischemic heart disease), peripheral arterial disease, cerebrovascular disease (for example, stroke or TIA, Transient Ischemic Attack), atherosclerosis, stenosis, renal artery stenosis, aortic disease, aortic aneurysm, cardiomyopathy, hypertensive heart disease, hypertension, heart failure, pulmonary heart disease, cardiac dysrhythmias, cardiovascular inflammation, inflammatory heart disease, endocarditis, inflammatory cardiomegaly, myocarditis, eosinophilic myocarditis, valvular heart disease, congenital heart disease, or rheumatic heart disease (optionally, also any of these diseases may be excluded from the disclosure).

Further, in the context of the disclosure, the inflammatory disease can be any inflammatory disease, in particular, cardiovascular inflammation, for example, carditis, endocarditis, myocarditis, pericarditis, vasculitis, arteritis, phlebitis, or capillaritis, or, for example, inflammation of the gastrointestinal tract, e.g., esophagitis, gastritis, gastroenteritis, enteritis, colitis, enterocolitis, duodenitis, ileitis, caecitis, appendicitis, or proctitis. The inflammatory disease according to the disclosure may further refer to hepatic inflammation, pulmonary inflammation, or skeletal inflammation. Alternatively, the inflammatory disease may refer to systemic inflammatory response syndrome (SIRS) or sepsis (optionally, also any of these diseases may be excluded from the disclosure).

Diabetes Mellitus

Type 1 Diabetes Mellitus

Type 1 Diabetes mellitus is a chronic endocrine autoimmune disease wherein the pancreas produces too little or no insulin. It is generally regarded as associated with progressive beta cell destruction, and linked to an increased morbidity and mortality risk compared to healthy subjects. As beta cell function can also deteriorate in Type 2 Diabetes mellitus, the disclosure may also concern prevention and/or treatment of Type 2 Diabetes mellitus.

It was found that the agent(s) according to the disclosure can be used to prevent and/or treat Type 1 Diabetes mellitus. Such treatment may also extend the honeymoon phase in Type 1 Diabetes mellitus, i.e., the period following diagnosis wherein the own pancreas is still able to produce a significant enough amount of insulin to limit exogenous insulin needs in the body and maintain blood glucose control.

Extending this period can dramatically improve quality of life in patients. The treatment can also be applied to reduce severity of symptoms of Type 1 Diabetes mellitus, for example, symptoms or complications related to impaired function of eye(s), kidney(s), nerves and/or brain.

More specifically, the treatment may inhibit decay of beta cell function and/or inhibit production of autoantibodies associated with Type 1 Diabetes mellitus, such as islet (beta) cell autoantibodies, autoantibodies to insulin, autoantibodies to GAD (GAD65), autoantibodies to the tyrosine phosphatases IA-2 and IA-2$\gamma$, and/or autoantibodies to zinc transporter 8 (ZnT8).

The symptoms of Type 1 Diabetes mellitus may include polyuria, polydipsia, polyphagia, weight loss, fatigue, nausea, and blurred vision. The onset of symptomatic disease can be sudden. In this regard, it is not unusual that patients with Type 1 Diabetes mellitus suffer from diabetic ketoacidosis (DKA). The following diagnostic criteria can be applied for Type 1 and Type 2 Diabetes mellitus (American Diabetes Association, ADA):

A fasting plasma glucose (FPG) level $\geq$126 mg/dL (7.0 mmol/L), or

A 2-hour plasma glucose level $\geq$200 mg/dL (11.1 mmol/L) during a 75-g oral glucose tolerance test (OGTT), or A random plasma glucose $\geq$200 mg/dL (11.1 mmol/L) in a patient with classic symptoms of hyperglycemia or hyperglycemic crisis.

Additionally and/or alternatively, C-peptide response after a mixed meal test can be assessed, as described in the Example and/or as described by Lachin et al. (2011 PLoS ONE Vol. 6(11) e26471).

Type 1 Diabetes mellitus and/or its preceding symptoms can be confirmed by the presence of one or more autoimmune markers, which include islet (beta) cell autoantibodies, autoantibodies to insulin, autoantibodies to GAD (GAD65), autoantibodies to the tyrosine phosphatases IA-2 and IA-2$\gamma$, and autoantibodies to zinc transporter 8 (ZnT8) as well as increased HbA1c and altered glucose tolerance.

Type 2 Diabetes Mellitus

Type 2 diabetes is a common metabolic condition that develops when the body fails to produce enough insulin or when insulin fails to work properly, which is referred to as insulin resistance. Insulin is the hormone that stimulates cells to uptake glucose from the blood to use for energy. When this is the case, cells are not instructed by insulin to take up glucose from the blood, meaning the blood sugar level rises (referred to as hyperglycemia).

People usually develop type 2 diabetes after the age of 40 years, although people of South Asian origin are at an increased risk of the condition and may develop diabetes from the age of 25 onwards. The condition is also becoming increasingly common among children and adolescents across all populations. Type 2 diabetes often develops as a result of overweight, obesity and lack of physical activity and diabetes prevalence is on the rise worldwide as these problems become more widespread. Type 2 diabetes accounts for approximately 90% of all diabetes cases (the other form being type 1 diabetes) and treatment approaches include lifestyle changes and the use of medication.

It was found that the agent(s) according to the disclosure can be used to prevent and/or treat Type 2 Diabetes mellitus. The treatment can be applied to reduce severity of symptoms of Type 2 Diabetes mellitus, for example, symptoms or complications related to polyuria, polydipsia. More specifically, the treatment may reduce the need of exogenous hormone supplementation.

Cardiovascular Diseases

Coronary Artery Disease

Coronary artery disease is the most common of the cardiovascular diseases. It involves the reduction of blood flow to the heart muscle due to build-up of plaque (atherosclerosis) in the arteries of the heart. A common symptom is chest pain or discomfort, which may travel into the shoulder, arm, back, neck, or jaw. In many cases, the first sign is a heart attack. Other complications include heart failure or an abnormal heartbeat.

Risk factors include high blood pressure, smoking, diabetes, lack of exercise, obesity, high blood cholesterol, poor diet, depression, and excessive alcohol. A number of tests may help with diagnoses including: electrocardiogram, cardiac stress testing, coronary computed tomographic angiography, and coronary angiogram, among others.

Inflammatory Disorders

A subject suffering from or at risk of developing inflammatory disease can be identified by methods known in the art, e.g., gross examination of tissue or detection of inflammation associated in tissue or blood. Symptoms of inflammation include pain, redness and swelling of the affected tissue.

Systemic Inflammatory Response Syndrome (SIRS) and Sepsis

Systemic inflammatory response syndrome (SIRS) is an exaggerated defense response of the body to, for example, an infection, trauma, surgery, acute inflammation, ischemia or reperfusion, or malignancy. It involves the release of acute-phase reactants, which are direct mediators of widespread autonomic, endocrine, hematological and immunological alteration in the subject. Even though the purpose is defensive, the dysregulated cytokine storm has the potential to cause massive inflammatory cascade leading to reversible or irreversible end-organ dysfunction and even death. SIRS with a suspected source of infection is termed sepsis. Sepsis with one or more end-organ failure is called severe sepsis and with hemodynamic instability in spite of intravascular volume repletion is called septic shock.

SIRS may be diagnosed by the satisfaction of any two of the criteria below:

Body temperature over 38 or under 36 degrees Celsius;

Heart rate greater than 90 beats/minute;

Respiratory rate greater than 20 breaths/minute or partial pressure of $CO_2$ less than 32 mmHg;

Leucocyte count greater than 12000 or less than 4000/ microliters or over 10% immature forms or bands.

Additionally or alternatively, the use according to the disclosure may be for improving general health and/or reducing inflammation status, the latter preferably measured by higher erythrocyte sedimentation rate in comparison to healthy individuals (e.g., ESR values of at least 35, 40, 45, 50, 55, 60 mm/h) and/or decreased level of C-reactive protein in the blood (plasma), e.g., relative to not administering the composition according to the disclosure. C-reactive protein may, for example, be measured after 1-12, 1-4, 2-8, 4-12 weeks or after 1-12 months or 1-12 years of administration of the composition of the disclosure. C-reactive protein (CRP) is a protein made by the liver. CRP levels in the blood increase when there is a condition causing inflammation somewhere in the body. A CRP test measures the amount of CRP in the blood to detect inflammation status.

Additionally or alternatively, the use according to the disclosure may be for inducing weight loss in a subject, or for reducing Body Mass Index (BMI).

Autoimmune Diseases

Autoimmune diseases are a class of diseases in which the immune system produces an inappropriate response against a subject's own cells, tissues and/or organs. This may result in inflammation, damage and loss of function. Common autoimmune diseases are Hashimoto hypothyroidism, Graves hyperthyroidism, Rheumatoid arthritis, Celiac disease, Asthma/COPD, Addison's disease, IBD (Crohn's disease and colitis ulcerosa), Systemic lupus erythematosus, Vasculitis, Guillain Barre and Chronic Inflammatory Demyelinating Polyneuropathy (CIDP), Multiple sclerosis, Psoriasis (arthritis), Vitiligo, Type 1 diabetes mellitus and Bechterew's disease.

The causes of autoimmune diseases are not clear. However, factors such as infections and genetic disposition may play a role in triggering autoimmune diseases. Autoimmune diseases are usually diagnosed using a combination of clinical history and blood tests (detecting, amongst others, autoantibodies, or markers of inflammation or organ function).

Although there is a wide range of treatment options, which depend on the stage and type of autoimmune disease, there is no definitive cure for autoimmune diseases.

Treatment strategies are generally directed to relieve symptoms, minimize organ or tissue damage and preserve organ function. For example, treatment options may include replacement of organ functions (such as administering insulin in Type 1 diabetes mellitus and thyroxine in Hashimoto's hypothyroidism), non-steroidal anti-inflammatory medications (NSAIDS), corticosteroid anti-inflammatory medications (such as prednisolone), $TNF\alpha$ inhibitors, immunosuppressive medications, or immunoglobulin replacement therapy.

Endocrine Autoimmune Diseases

Among the various autoimmune diseases, autoimmune endocrine disorders are most common. The endocrine system comprises glands that produce hormones and deliver these directly into the circulatory system, as well as feedback loops to achieve homeostasis. The organs of the endocrine system can be affected by several autoimmune diseases, characterized by different impact and severity. Sometimes multiple organs are involved, such as in polyglandular autoimmune syndrome.

Among the different autoimmune endocrine diseases, Type 1 Diabetes mellitus, Hashimoto's disease, Graves' disease, and Addison's disease are especially frequent in clinical practice.

Hashimoto's Disease

Hashimoto's disease is an organ specific autoimmune disorder with the highest occurrence. It is also referred to as Hashimoto's thyroiditis, or chronic lymphocytic thyroiditis and is regarded as an autoimmune disease in which the thyroid gland is gradually destroyed. The causes of Hashimoto's disease are still unclear, although an inappropriate cell-mediated immune response and autoantibody production against the thyroid gland are generally thought to be involved. Both B (CD20+ and CD79 alpha+) cells are seen in the mononuclear lymphatic infiltrates (destruction of thyroid follicles and thyrocytes) as well as excessively stimulated T cells CD4+(T helper type 2 Th2 cells lead to an excessive stimulation and production of B cells that produce antibodies against thyroid antigens, subsequently driving thyroiditis in the thyroid gland Marazuela et al., J. Clin. Endocrinol. Metab. 2006 September; 91(9):3639-46).

Until thyroid hypofunction becomes apparent, an enlargement of the thyroid is typically the only symptom. However, the disease can progress into hypothyroidism, thereby often leading to symptoms including edema, weight gain, and fatiguability (susceptible to fatigue), sensitivity to cold and diarrhea, and physical findings such as dry skin, hoarseness, bradycardia, and/or a prolonged relaxation phase of the Achilles tendon reflex.

Hashimoto's disease may be confirmed by the presence of anti-thyroid peroxidase (TPO) antibodies and anti-thyroglobulin (Tg) antibodies in the patient's serum. Further, an elevated level of thyroid-stimulating hormone (TSH), and lowered levels of free T4 (FT4), lowered levels of free T3, and/or elevated levels of anti-microsomal antibodies, in comparison to the average in healthy individuals, can help obtain positive diagnosis.

Hashimoto's disease is currently treated with thyroid hormone replacement agents such as levothyroxine (FT4 supplementation), triiodothyronine (T3 supplementation) or desiccated thyroid extract. It was found that the agent(s) according to the disclosure can be used to prevent and/or treat Hashimoto's disease, optionally in combination with thyroid hormone replacement agents as described above. The treatment according to the disclosure can also be applied to reduce severity of symptoms of Hashimoto's disease, for example, one or more symptoms or complications as described above.

Graves' Disease

Graves' disease is an autoimmune disease that affects the thyroid, and is the most common cause of hyperthyroidism. The disease can be characterized by the presence of autoantibodies in the serum that bind the thyrotropin receptor, i.e., the thyroid stimulating hormone (TSH) receptor. These anti-TSH receptor antibodies (TBII) overstimulate the thyroid gland, which may lead to goiter and signs of thyrotoxicosis as well as involvement of the eye muscles in a subset of patients (Graves ophthalmopathy).

Among the symptoms are hyperthyroidism, goiter, and orbitopathy. Other major symptoms include weight loss (with increased appetite), fatigability, shortness of breath, hyperhidrosis, finger tremors, diarrhea, periodic paralysis (in male), and muscle weakness. With regard to Graves ophthalmopathy, patients may suffer from proptosis of the eyes, blurred vision and dry/red eyes (in rare cases it can lead to blindness). Two signs are truly specific of Graves' disease and not seen in other hyperthyroid conditions: exophthalmos and pretibial myxedema.

Graves' disease may be confirmed by low serum TSH level (sometimes not detectable) and/or elevations in free T3 and free T4, in comparison to health individuals. Patients may typically be positive for anti-TSH receptor antibodies (TBII) in their serum.

Current treatment of Graves' disease may involve administration of antithyroid drugs (block and replacement therapy), radioiodine (radioactive iodine I-131); and/or thyroidectomy (surgical excision of the gland). Usually, strumazol and methimazole (PTU) are prescribed followed by thyroid hormone replacement agents such as levothyroxine (FT4 supplementation), triiodothyronine (T3 supplementation) or desiccated thyroid extract.

Alternatively or in combination with the above-described treatment, it was found that the agent(s) according to the disclosure can be used to prevent and/or treat Graves' disease including ophthalmopathy. The treatment according to the disclosure can also be applied to reduce severity of symptoms of Graves' disease, for example, one or more symptoms or complications as described above.

Addison's Disease

Addison's disease is a chronic endocrine autoimmune disorder in which the adrenal glands do not produce sufficient steroid hormones. The disease is caused by destruction of the adrenal glands (both cortex and medulla produced hormones). The disease may be a manifestation of polyglandular autoimmune syndrome involving complications by other organ-specific autoimmune disorders (e.g., Type 1 Diabetes mellitus, Hashimoto's disease, Vitiligo).

Hyperpigmentation due to increased secretion of ACTH is a characteristic clinical sign of Graves' disease. Other symptoms include abdominal pain in the stomach region, orthostasis and weight loss.

Medical examination will typically determine if orthostasis, hypoglycemia, hyponatremia, hyperkalemia, and peripheral blood eosinophilia are present. To confirm Addison's disease, demonstration of low adrenal hormone levels even after stimulation (called the ACTH stimulation test or synacthen test) with synthetic pituitary ACTH hormone tetracosactide is generally performed for the diagnosis.

Treatment generally involves replacement therapy with oral hydrocortisone and/or mineralocorticoids like fludrocortisone (if the adrenal medulla is also involved). It was found that the agent(s) according to the disclosure can be used to prevent and/or treat Addison's disease, optionally in addition to treatment with hydrocortisone. The treatment according to the disclosure can also be applied to reduce severity of symptoms of Addison's disease, for example, one or more symptoms or complications as described above.

Skin Autoimmune Disease

Psoriasis (Arthritis)

Psoriasis is a chronic autoimmune disease that leads to rapid production of skin cells. The underlying etiology is that T cells attack healthy skin cells, which causes the skin cell production process to go into overdrive. The new cells are pushed to the skin's surface, where they pile up. This results in the plaques and red inflamed areas of skin, which are most commonly associated with psoriasis. Subtypes of psoriasis include (1) plaque psoriasis, which is the most frequently occurring type of psoriasis. It is characterized by red, inflamed patches that cover areas of the skin, typically on the elbows, knees, and scalp. These patches are often covered with whitish-silver scales or plaques;

(2) Guttate psoriasis, which is the form of psoriasis, which is common in children and causes small pink spots, typically on the torso, arms, and legs;

(3) Pustular psoriasis, which is more common form of psoriasis in adults and causes white, pus-filled blisters and areas of red inflamed skin, typically on the hands or feet;

(4) Inverse psoriasis, which causes bright areas of red, shiny, inflamed skin. Patches of inverse psoriasis typically develop under armpits or breasts, in the groin, or around skinfolds;

(5) Erythrodermic psoriasis, which is a severe and rare type of psoriasis. This form often covers large sections of the body where the skin may appear sunburned. A person with this type of psoriasis may run a fever or become very ill, and this form of psoriasis can be life-threatening;

(6) Psoriatic arthritis with involvement of the joints.

Psoriasis symptoms are different among patients. Common symptoms include red patches of skin covered with thick, silvery scales, small scaling spots (commonly seen in children), dry, cracked skin that may bleed, itching, burning or soreness, thickened, pitted or ridged nails, and/or swollen and stiff joints. Most types of psoriasis can go through cycles, flaring for a few weeks or even months, then subsiding for a period or even going into remission. Psoriasis arthritis (or psoriatic arthritis) is a condition wherein swollen, sore joints of arthritis occur together with psoriasis.

For mild disease that involves only small areas of the body, topical treatments (applied on the skin), such as creams, lotions, and sprays, are generally prescribed. Occasionally, a local injection of steroids directly into a tough or resistant isolated psoriatic plaque may be helpful.

Tumor necrosis factor (TNF) antagonists (or anti TNFα therapy) have become first-line agents in the treatment of moderate-to-severe psoriasis or psoriatic arthritis. Examples include infliximab, etanercept, and adalimumab. Anti TNFα therapy has been found effective in treating both psoriasis and psoriatic arthritis and may also reduce the risk of cardiovascular events. It was found that, in addition or alternatively, the agent(s) according to the disclosure can be used to prevent and/or treat psoriasis and/or psoriatic arthritis. In addition, the treatment according to the disclosure can also be applied to reduce severity of symptoms of psoriasis and psoriatic arthritis, for example, one or more symptoms or complications as described above. Particularly the combined treatment with a TNF antagonist or anti-TNFα and treatment according to the disclosure may be synergistic.

Vitiligo

Vitiligo is a disease wherein white patches of skin appear on different parts of the body. It is generally thought that this is due to autoimmune processes that destroy the cells that make pigment (color) in the skin, i.e., melanocytes. Vitiligo can also occur in mucous membranes (such as inside the mouth and nose) and in the eye.

Recent studies reveal dysbiosis in the diversity of microbial community structure in the skin microbiome of vitiligo subjects. Although the individual specific microbiome signature is dominant over the vitiligo-specific microbiota, a clear decrease in taxonomic richness and evenness can be noted in lesional patches (Ganju et al., Sci. Rep. 2016 Jan. 13; 6:18761).

The white patches of vitiligo are more common in areas where the skin is exposed regularly to sunlight. The patches may be on the hands, feet, arms, face, and lips, but occasionally also on the armpits and groin, around the mouth, eyes, nostrils, navel, genitals, rectal areas. Further, people with vitiligo often have hair that turns gray early (e.g., before age 35).

Ultraviolet (UV) light can be used particularly in the early phase of vitiligo for diagnosis and to determine the effectiveness of UV treatment. Skin with vitiligo, when exposed to UV, typically will glow blue. In contrast, healthy skin will show no reaction.

Vitiligo can be classified into segmental vitiligo (SV) and non-segmental vitiligo (NSV), where NSV is the most common type of vitiligo.

In non-segmental vitiligo (NSV), there typically is symmetry in the location of the patches of depigmentation. In extreme cases, little pigmented skin remains, which is referred to as vitiligo universalis. NSV can initiate at any age, whereas segmental vitiligo is far more prevalent in teenage years.

Segmental vitiligo (SV) tends to affect areas of skin that are associated with dorsal roots from the spinal cord and is most often unilateral. It is much more stable/static in course. SV typically does not improve with UV light therapy, but surgical treatments such as cellular grafting can be effective.

There is no definitive cure for vitiligo but several treatment options are available, including ultraviolet light and/or creams. Topical preparations (i.e., creams) of immune suppressing medications including corticosteroids or glucocorticoids (such as clobetasol and/or betamethasone) and calcineurin inhibitors (such as tacrolimus and/or pimecrolimus) are considered to be first-line vitiligo treatments, while UV(B) therapy is considered a second-line treatment for vitiligo.

It was found that, in addition or alternatively to the above-described treatment(s), the agent(s) according to the disclosure can be used to prevent and/or treat vitiligo. Further, the treatment according to the disclosure can also be applied to reduce severity of symptoms of vitiligo, for example, one or more symptoms or complications as described above.

Rheumatoid Disorder

Rheumatoid Arthritis

Rheumatoid arthritis (RA) can be seen as an autoimmune disease in which the immune system attacks the joints. This leads to inflammation that causes the tissue that lines the inside of joints (the synovium) to thicken, resulting in painful joints.

If not treated, RA can damage cartilage, the elastic tissue that covers the ends of bones in a joint, and even the bones themselves. Eventually, there can be loss of cartilage, joints can become loose, unstable, painful and lose their mobility, or even deform. Unfortunately, joint damage generally cannot be reversed, and therefore early diagnosis and treatment is recommended to control RA.

RA most commonly occurs in the joints of the hands, feet, wrists, elbows, knees and ankles. RA can also affect body systems, such as the cardiovascular or respiratory systems, and is then called systemic RA. In the early stages, people with RA may experience tenderness and pain in the joints.

Symptoms of RA include stiffness and joint pain, specifically small joints (wrists, certain joints of the hands and feet), and typically for six weeks or longer. Along with pain, many people experience fatigue, loss of appetite and a mild fever.

No single test can definitely confirm RA, but blood tests can be performed, which measure inflammation levels and look for biomarkers such as antibodies that are linked with RA.

A high erythrocyte sedimentation rate and a high C-reactive protein (CRP) level, in comparison to healthy individuals, are biomarkers of inflammation. A high ESR or high CRP is not specific to RA, but when combined with the presence of RA-related antibodies, can confirm RA diagnosis.

Rheumatoid factor (RF) is an antibody found in the majority of people with RA. Because RF can occur in other inflammatory diseases, it is not a definitive sign of having RA. However, a different antibody—anti-cyclic citrullinated peptide (anti-CCP)—occurs primarily in RA patients. That makes a positive anti-CCP test a stronger indication of RA. In addition, an X-ray, ultrasound or magnetic resonance imaging scan can be performed to look for joint damage, such as erosions and narrowing of joint space.

With respect to treatment, nonsteroidal anti-inflammatory drugs (NSAIDs) are generally prescribed, which can ease arthritis pain and inflammation. Examples of NSAIDs include ibuprofen, ketoprofen and naproxen sodium. Further, corticosteroids, including prednisone, prednisolone and methylprednisolone, can be administered as anti-inflammatory medications.

DMARDs, i.e., disease-modifying anti-rheumatic drugs, may be used to slow down the progression of the disease. DMARDs include methotrexate, hydroxychloroquine, sulfasalazine, leflunomide, cyclophosphamide and azathioprine. A subcategory of DMARDs is known as "JAK inhibi-
tors," which block the Janus kinase, or JAK, pathways. An
example is Tofacitinib.

Biologicals may work more quickly than traditional
DMARDs, and are injected or given by infusion. In many
people with RA, a biological can slow, modify or stop the
disease. Particularly preferred are tumor necrosis factor
(TNF) antagonists (anti TNFα therapy).

It was found that, in addition or alternatively to the
above-described treatment(s), the agent(s) according to the
disclosure can be used to prevent and/or treat Rheumatoid
arthritis and/or one or more of its symptoms as described
above. The combined treatment according to the disclosure
with a TNF antagonist or anti-TNFα may be synergistic.

Bechterew's Disease

Bechterew's disease (or Ankylosing Spondylitis) is a
chronic autoimmune rheumatoid disorder involving particu-
larly the axial skeleton. Typically, it presents in male adults
of 20-30 years of age.

The most serious symptoms are neck and lower back pain.
A typical symptom is nocturnal pain, as well as inflamma-
tion of the sacroiliac joint. In some patients, bony deformi-
ties of the spine can occur, which may result in motion
restriction. Apart from these spinal complaints, inflamma-
tion of peripheral joints is common.

In order to diagnose Bechterew's disease, examination of
the vertebral column is performed to assess restrictions in
cervical and lumbar spine mobility. A Schober test can be
helpful in estimating the amount of lumbar forward flexion
restriction. The diagnosis could be confirmed by discovery
of HLA-B27 antigens in patient's blood.

Treatment options include administration of NSAID, sul-
fasalazine, methotrexate, leflunomide, corticosteroid, TNFα
inhibitor(s). It was found that, in addition or alternatively to
the above-described treatment(s), the agent(s) according to
the disclosure can be used to prevent and/or treat Bech-
terew's disease and/or one or more of its symptoms as
described above. Particularly the combination of treatment
according to the disclosure with a TNF antagonist or anti-
TNFα may be synergistic.

Systemic Lupus Erythematosus

Systemic lupus erythematosus (SLE), also known simply
as lupus, is an autoimmune disease in which the body's
immune system mistakenly attacks healthy tissue in many
parts of the body. Symptoms vary between people and may
be mild to severe. SLE significantly increases the risk of
cardiovascular disease with this being the most common
cause of death. With modern treatment about 80% of those
affected survive more than 15 years after diagnosis. Com-
mon symptoms include painful and swollen joints, fever,
chest pain, hair loss, mouth ulcers, swollen lymph nodes,
feeling tired, and a red rash, which is most commonly on the
face. Often there are periods of illness, called flares, and
periods of remission during which there are few symptoms.
There is no cure for SLE. Treatments may include NSAIDs,
corticosteroids, immunosuppressants, hydroxychloroquine,
and methotrexate. Although corticosteroids are rapidly
effective, long term use results in side effects. It was found
that, in addition or alternatively to the above-described
treatment(s), the agent(s) according to the disclosure can be
used to prevent and/or treat SLE disease and/or one or more
of its symptoms as described above.

Vasculitis

Vasculitis is seen ranging from large to small vessels that
are inflamed. Large vessel vasculitis diseases are Giant cell
arteritis or arteriitis temporalis, Takayasu's disease (Ta-
kayasu arteritis). Medium large vessel vasculitis diseases are

14

Polyarteritis Nodosa (PAN) and Kawasaki's disease. Small
vessel vasculitis diseases comprise of Microscopic poly-
angiitis, GPA (Granulomatosis with PolyAngiitis also
known as Wegener's disease), EGPA (Eosinophilic Granu-
lomatosis with PolyAngiitis, also known as Churg-Strauss
Syndrome), Henoch-Schonlein syndrome, Anti-GBM
(Goodpasture's syndrome) and Cryoglobulinemia-associ-
ated vasculitis. It was found that the agent(s) according to
the disclosure can be used to prevent and/or treat vasculitis
and/or one or more of its symptoms as described above.

Gastrointestinal Autoimmune Disease

Celiac Disease

Celiac disease (or coeliac disease) is an autoimmune
disorder where the ingestion of gluten leads to damage of the
small intestinal epithelial cells. It may typically occur in
genetically predisposed people and in combination with type
1 diabetes. Celiac disease and Type 1 Diabetes mellitus may
have similar pathogenesis wherein heritable genetic factors
as well as dietary and microbial exposures may play a role,
particularly in early life (see e.g., Verdu and Danska Nature
Immunology| VOL 19| JULY 2018| 685-695).

When people with celiac disease eat gluten (a protein
found in wheat, rye and barley), their body initiates an
immune response that attacks the small intestine, leading to
damage of the villi (small fingerlike projections that line the
small intestine). When the villi get damaged, nutrients
cannot be absorbed properly by the intestine. Symptoms are
abdominal cramps, malnutrition and osteoporosis.

There are several serologic (blood) tests available that
screen for celiac disease antibodies, but the most commonly
used is a tTG-IgA test. For this test to work, the patient must
be consuming gluten. In addition, diagnosis for Celiac
disease can be reached by an endoscopic biopsy. A biopsy is
then taken of the small intestine, which can subsequently be
analyzed to see if there is any damage consistent with celiac
disease. The diagnosis may be confirmed when improve-
ment is seen while on a gluten-free diet.

Currently, the only treatment for celiac disease is a strict
gluten-free diet. People living gluten-free must avoid foods
with wheat, rye and barley, for example, bread and beer.
Ingesting small amounts of gluten can trigger small intestine
damage. It was found that, in addition or alternatively to the
above-described treatment(s), the agent(s) according to the
disclosure can be used to prevent and/or treat Celiac disease
and/or one or more of its symptoms as described above.

Inflammatory Bowel Disease

Inflammatory bowel disease (IBD) is a term for two
conditions (Crohn's disease and colitis ulcerosa) that are
characterized by chronic inflammation of the gastrointesti-
nal (GI) tract. IBD is thought to be caused by a dysregulated
immune response. Symptoms of IBD include persistent
diarrhea, abdominal pain, rectal bleeding/bloody stools,
weight loss, and fatigue. In IBD, the immune system
responds incorrectly to environmental triggers, which causes
inflammation of the gastrointestinal tract. There also appears
to be a genetic component-someone with a family history of
IBD is more likely to develop this inappropriate immune
response.

IBD is diagnosed using a combination of endoscopy (for
Crohn's disease) or colonoscopy (for ulcerative colitis) and
imaging studies, such as contrast radiography, magnetic
resonance imaging (MRI), or computed tomography (CT).

Several types of medications may be used to treat IBD:
aminosalicylates, corticosteroids (such as prednisone),
immunomodulators, and the newest class approved for IBD
the "biologics", such as anti-TNFalpha. Several vaccina-
tions for patients with IBD are recommended to prevent infections. Severe IBD may require surgery to remove damaged portions of the gastrointestinal tract, but advances in treatment with medications mean that surgery is less common than it was a few decades ago. It was found that, in addition or alternatively to the above-described treatment(s), the agent(s) according to the disclosure can be used to prevent and/or treat IBD and/or reduce severity of one or more of its symptoms as described above.

Neurological Diseases

Guillain Barre

Guillain-Barré syndrome (GBS) is a rapid-onset muscle weakness caused by the immune system damaging the peripheral nervous system (acute polyneuropathy). The initial symptoms are typically changes in sensation or pain along with muscle weakness, beginning in the feet and hands, often spreading to the arms and upper body, with both sides being involved. The symptoms may develop over hours to a few weeks. During the acute phase, the disorder can be life-threatening, with about 15 percent of people developing weakness of the breathing muscles and, therefore, requiring mechanical ventilation.

Although the cause is unknown, the underlying mechanism involves an autoimmune disorder in which the body's immune system mistakenly attacks the peripheral nerves and damages their myelin insulation. Sometimes this immune dysfunction is triggered by an infection or, less commonly by surgery and rarely by vaccination. Diagnosis is usually made based on the signs and symptoms, through the exclusion of alternative causes, and supported by tests such as nerve conduction studies and examination of the cerebrospinal fluid. There are a number of subtypes based on the areas of weakness, results of nerve conduction studies and the presence of certain antibodies. Treatment with intravenous immunoglobulins or plasmapheresis, together with supportive care, will lead to good recovery in the majority of people. Recovery may take weeks to years, with about a third having some permanent weakness. It was found that, in addition or alternatively to the above-described treatment(s), the agent(s) according to the disclosure can be used to prevent and/or treat GBS and/or reduce severity of one or more of its symptoms as described above.

CDIP

Chronic inflammatory demyelinating polyneuropathy (CDIP) is an acquired immune-mediated inflammatory disorder of the peripheral nervous system. The disorder is sometimes called chronic relapsing polyneuropathy (CRP) or chronic inflammatory demyelinating polyradiculoneuropathy (because it involves the nerve roots). CIDP is closely related to Guillain-Barre syndrome and it is considered the chronic counterpart of that acute disease. It was found that the agent(s) according to the disclosure can be used to prevent and/or treat CDIP and/or reduce severity of one or more of its symptoms as described above.

Multiple Sclerosis

Multiple sclerosis (MS) is a demyelinating disease in which the insulating covers of nerve cells in the brain and spinal cord are damaged. This damage disrupts the ability of parts of the nervous system to transmit signals, resulting in a range of signs and symptoms, including physical, mental, and sometimes psychiatric problems. Specific symptoms can include double vision, blindness in one eye, muscle weakness and trouble with sensation or coordination. MS takes several forms, with new symptoms either occurring in isolated attacks (relapsing forms) or building up over time (progressive forms). Between attacks, symptoms may disappear completely; however, permanent neurological problems often remain, especially with the advancement of the disease. While the cause is unclear, the underlying mechanism is thought to be either destruction by the immune system or failure of the myelin-producing cells. Proposed causes for this include genetics and environmental factors such as being triggered by a viral infection. MS is usually diagnosed based on the presenting signs and symptoms and the results of supporting medical tests. There is no known cure for multiple sclerosis. Treatments attempt to improve function after an attack and prevent new attacks. It was found that the agent(s) according to the disclosure can be used to prevent and/or treat MS and/or reduce severity of one or more of its symptoms as described above.

Asthma and COPD

In the context of the disclosure, also the prevention and/or treatment of asthma is foreseen, in view of autoimmune mechanisms that might be operating in asthma as well.

Asthma is a common chronic inflammatory disease of the airways of the lungs. It can be characterized by reversible airflow obstruction and bronchospasm. Symptoms include episodes of coughing, wheezing, chest tightness, and shortness of breath.

There is currently no definitive diagnostic test for asthma, and diagnosis is typically based on the pattern of symptoms and response to therapy over time. A diagnosis of asthma can be made if there is a history of recurrent wheezing, coughing or difficulty breathing and these symptoms occur or worsen due to exercise, viral infections, allergens and/or air pollution; also FEV1 test upon bronchodilators are done to study effect on lung function.

An effective treatment for asthma is identifying what triggers the disease, such as cigarette smoke, pets, or aspirin, and eliminating exposure to these triggers. In addition, bronchodilators are often recommended. In the case of mild but persistent disease, low-dose inhaled corticosteroids or alternatively, leukotriene antagonists or mast cell stabilizers can be applied. For serious asthma, i.e., patients who have daily attacks, inhaled corticosteroids, i.e., in a higher dose, can be used.

It was found that, in addition or alternatively to the above-described treatment(s), the agent(s) according to the disclosure can be used to prevent and/or treat asthma and/or one or more of its symptoms as described above.

The effectiveness of the treatment according to the disclosure confirms a link between intestinal microbiome composition and risk of developing asthma, which has been postulated by Korpela et al. (Nat. Commun. 2016 Jan. 26; 7:10410).

(Lung) emphysema is one of the diseases that comprise COPD (chronic obstructive pulmonary disease). Emphysema involves gradual damage of lung tissue, specifically thinning and destruction of the alveoli or air sacs. The agent(s) according to the disclosure can be used to prevent and/or treat COPD, or specifically (lung) emphysema, and/or one or more of its symptoms as described above.

Other Conditions

The disclosure may also be used in the context of preventing and/or treating other autoimmune diseases, particularly including autoimmune hepatitis, Diabetes mellitus Type 1a and/or 1b, polyglandular autoimmune syndrome, Myasthenia gravis, Pernicious anemia, Primary biliary cirrhosis, Sclerosing cholangitis, Antiphospholipid antibody syndromes, Dermatomyositis, Mixed connective tissue disease, Polymyalgia rheumatica, Polymyositis, Scleroderma and Sjögren's syndrome. However, it is also envisaged that any of the above mentioned diseases is excluded from the disclosure.

Additionally, the agent(s) according to the disclosure may be used to prevent and/or treat an allergy, also known as allergic diseases, which are conditions caused by hypersensitivity of the immune system to typically harmless substances in the environment. Common allergies include hay fever (plant pollen allergy) and food allergy (relating e.g., to cow's milk, soy, eggs, wheat, peanuts, tree nuts, fish, and/or shellfish).

The disclosure may also allow for the prevention and/or treatment of the following diseases, but optionally these diseases are excluded from the scope of the disclosure: gastrointestinal disorders, *Clostridium difficile* infection, Morbus Crohn (Crohn's disease), ulcerative colitis or Inflammatory Bowel Disease (IBD), and/or Irritable bowel syndrome (IBS). Alternatively and/or additionally, any of the following diseases may be excluded from the disclosure: systemic and localized (organ specific) autoimmune diseases, endocrine autoimmune disease, Type 1 Diabetes mellitus, Type 2 Diabetes mellitus, Hashimoto's disease, Graves's disease, or Addison's disease, skin autoimmune disease, Psoriasis or Vitiligo, rheumatoid autoimmune diseases, rheumatoid arthritis, Bechterew's disease, and gastrointestinal autoimmune disease, Celiac disease, vasculitis, COPD, CIDP, MS, SLE, Guillain-Barre. The disease according to the disclosure need not be inflammation-related.

Treatment According to the Disclosure

The agent for use in the prevention or treatment of an autoimmune disease as described herein may be a *Desulfovibrio* species, wherein the *Desulfovibrio* species is preferably chosen from the group consisting of *Desulfovibrio piger* (ATCC 29098), *Desulfovibrio fairfieldensis* (ATCC700045), *Desulfovibrio desulfuricans* (Essex 6 ATCC 29577), *D. desulfuricans* (MB ATCC 27774), *Desulfovibrio* indonensis (NCIMB 13468), *Desulfovibrio alaskensis* (NCIMB 13491), *Desulfovibrio vietnamensis* (DSM 10520), *Desulfovibrio gigas* (DSM 1382), *Desulfovibrio intestinalis* (DSM 11275), *Desulfovibrio longreachensis* (ACM 3958), *Desulfovibrio termitidis* (DSM 5308), *Desulfovibrio vulgaris* subsp. vulgaris (DSM 644), and *Desulfovibrio vulgaris* subsp. *oxamicus* (DSM 1925). Additionally or alternatively, the agent may be a *Bacteroides* species, preferably *Bacteroides* stercoris, or relative thereof such as a relative having at least 70, 80, 85, 90, 95, 96, 97, 98, 99, 99.5, 99.9% sequence identity with the 16S rDNA sequence of the type strain of *Bacteroides* stercoris.

Most preferably the *Desulfovibrio* species is *Desulfovibrio piger*, or a relative thereof having at least 70, 80, 85, 90, 95, 96, 97, 98, 99, 99.5, 99.9% sequence identity with the 16S rDNA sequence of *Desulfovibrio piger* (e.g., SEQ ID NO:1). Such cut-off value based on 16S rDNA similarity can define species with similar characteristics and/or functionality.

Preferably, an amount of at least $10^4$, $10^5$, $10^6$, $10^7$, $10^8$ *Desulfovibrio* cells may be used, e.g., in a composition wherein the *Desulfovibrio* species is comprised, for example, per ml or per g of the composition. Alternatively or additionally, a total of between $10^4$ and $10^{16}$, $10^4$ and $10^{15}$, $10^4$ and $10^{14}$, $10^4$ and $10^{12}$, $10^6$ and $10^{12}$, preferably between $10^8$ and $10^{10}$, *Desulfovibrio* cells may preferably be used, e.g., per ml or per g composition wherein the *Desulfovibrio* species is comprised.

Alternatively or additionally, the *Desulfovibrio* cells may be viable, but it is also envisaged that (only) attenuated or dead cells are used, e.g., obtained after pasteurization, or, for example, obtained after incubation at 50-100, 60-80, 65-75, or 70 degrees Celsius, preferably for a period of at least 5, 10, 15, 20, 25, 30, 40, 50 minutes, or obtained exposure to UV or gamma irradiation, preferably for a period of at least 1, 5, 10, 20 30 seconds, or 1, 5, 10, 15, 20, 25, 30, 40, 50 minutes, or obtained after incubation with oxygen, e.g., gas comprising at least 15, 20, 25, 30, 35, 40, 45, 50, 60, 70, 80, 90, 99, 100 vol. % oxygen, preferably for a period of at least 1, 5, 10, 20 30 seconds, or 1, 5, 10, 15, 20, 25, 30, 40, 50 minutes. Preferably, the *Desulfovibrio* species is the first, second, third, fourth, or fifth most dominant bacterial species in the composition, i.e., has the highest cell count in comparison to other bacterial species contained in the composition, or is at least in the top 5.

The *Desulfovibrio* species according to the disclosure is preferably not comprised in fecal matter, or, if it is comprised in fecal matter (e.g., as an alternative to the above-mentioned composition), it is enriched, i.e., the number of *Desulfovibrio* cells is higher than in prior art fecal matter, for example, *Desulfovibrio* cells have been added to the fecal matter, or the fecal matter has been exposed to conditions favoring growth of the *Desulfovibrio* species. If the *Desulfovibrio* species according to the disclosure is comprised in fecal matter, preferably at least at least $10^4$, $10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $10^8$, $10^9$, $10^{10}$, $10^{11}$, $10^{12}$, $10^{13}$ *Desulfovibrio* cells are comprised in the fecal matter, for example, per ml or per g fecal matter. Preferably, the *Desulfovibrio* species is the first, second, third, fourth, or fifth most dominant bacterial species in the fecal matter, i.e., has the highest cell count in comparison to other bacterial species contained in the fecal matter, or is at least in the top 5.

The agent according to the disclosure may additionally or alternatively be an amino acid substituted with one or more halogens, preferably one halogen, preferably a chloro, fluoro or bromo-substituted amino acid. There is a preference for an aromatic amino acid, optionally substituted with one or more halogens, preferably one halogen, e.g., on the 6-position, preferably a chloro, fluoro or bromo-substituted, e.g., on the 6 position, aromatic amino acid. There is a higher preference for tryptophan, tyrosine, or phenylalanine, optionally substituted with one or more halogens, preferably one halogen (e.g., on the 6 position), preferably a chloro, fluoro or bromo-substituted, e.g., on the 6 position, tryptophan, tyrosine, or phenylalanine, for example, a chloro, fluoro or bromo-substituted tryptophan. Even more preferred is a halogenated tryptophan, e.g., on the 6-position, preferably chlorotryptophan, fluorotryptophan or bromotryptophan. The highest preference is 6-bromotryptophan, or any derivative or functional equivalent of thereof. The agent may be used in an amount of at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, 200, 300, 400, 500, 600, 700, 800, 900 µg (microgram), for example, per ml or per g of a composition wherein it is comprised. Alternatively or additionally, a total of between 0.1-10, 0.5-15, 1-20, 1-100, 5-100, 1-500, 50-750 µg (microgram) may preferably be used, e.g., per ml or per g composition wherein the agent(s) is comprised. Alternatively, the agent may be used in an amount of at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, 200, 300, 400, 500, 600, 700, 800, 900 mg, for example, per ml or per g of a composition wherein it is comprised. Alternatively or additionally, a total of between 0.1-10, 0.5-15, 1-20, 1-100, 5-100, 1-500, 50-750 µg (microgram) may preferably be used, e.g., per ml or per g composition wherein the agent is comprised. Alternatively or additionally, a total of between 0.1-10, 0.5-15, 1-20, 1-100, 5-100, 1-500, 50-750 mg may preferably be used, e.g., per ml or per g composition wherein the agent(s) is comprised. The administration may be oral administration, subcutaneous or intravenous administration. The total amount to be administered may depend on body weight of the subject to be treated, and can be determined by the skilled person. For example, a single dose may comprise between 10 microgram and 100 g, or between 10 mg and 50 g or between 50 mg and 10 g or between 100 mg and 5 g. The dose may be administered periodically as described elsewhere herein. Additionally or alternatively, the agent is preferably not comprised in fecal matter, or, if it is comprised in fecal matter (e.g., as an alternative to the above-mentioned composition), it is enriched, i.e., the amount of the agent is higher than in prior art fecal matter, i.e., at least 1, 2, 3, 4, 5, 6, 7, 8, 9, 10 wt. % higher in comparison to any fecal matter or fecal microbiota transplant to which the agent has not been added. According to the disclosure, the agent can be added to the fecal matter. If the agent is comprised in fecal matter, preferably at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, 200, 300, 400, 500, 600, 700, 800, 900 ng, or at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, 200, 300, 400, 500, 600, 700, 800, 900 µg (microgram), or at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100 mg of the agent is comprised in the fecal matter, for example, per ml or per g fecal matter. Preferably, the agent is the first, second, third, fourth, or fifth most dominant metabolite in the fecal matter, i.e., has the highest weight amount in comparison to other metabolites contained in the fecal matter, or is at least in the top 10, or top 5.

Additionally or alternatively, the agent according to the disclosure may be a mono or di fatty acid substituted glycerol phosphocholine (GPC), preferably wherein the fatty acid(s) are (independently) saturated or (mono or poly) unsaturated fatty acids.

There is a preference for unsaturated fatty acids such as myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid. There is a higher preference for a substituted glycerol phosphocholine (GPC) that contains one or more of myristoleic acid and arachidonic acid. There is a higher preference and good results have been obtained with 1-myristoyl-2-arachidonoyl-glycero-phosphocholine (MA-GPC) and 1-arachidonoyl-glycero-phosphocholine (A-GPC), or any derivative or functional equivalent of these. The agent may be used in an amount of at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, 200, 300, 400, 500, 600, 700, 800, 900 µg (microgram), for example, per ml or per g of a composition wherein it is comprised. Alternatively or additionally, a total of between 0.1-10, 0.5-15, 1-20, 1-100, 5-100, 1-500, 50-750 µg (microgram) may preferably be used, e.g., per ml or per g composition wherein the agent(s) is comprised. Alternatively, the agent may be used in an amount of at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, 200, 300, 400, 500, 600, 700, 800, 900 mg, for example, per ml or per g of a composition wherein it is comprised. Alternatively or additionally, a total of between 0.1-10, 0.5-15, 1-20, 1-100, 5-100, 1-500, 50-750 µg (microgram) may preferably be used, e.g., per ml or per g composition wherein the agent is comprised.

Alternatively or additionally, a total of between 0.1-10, 0.5-15, 1-20, 1-100, 5-100, 1-500, 50-750 mg may preferably be used, e.g., per ml or per g composition wherein the agent(s) is comprised. The administration may be oral administration, subcutaneous or intravenous administration. The total amount to be administered may depend on body weight of the subject to be treated, and can be determined by the skilled person. For example, a single dose may comprise between 10 microgram and 100 g, or between 10 mg and 50 g or between 50 mg and 10 g or between 100 mg and 5 g. Alternatively or additionally, administration may be such that a plasma concentration is achieved in the subject to be treated of preferably between 0.1-100, 0.2-50, 0.5-25, 0.5-20, 0.5-3, 1-15, 2-10, 2-5 nmol/ml or between 0.1-100, 0.2-50, 0.5-3, 0.5-25, 0.5-20, 1-15, 2-10, 2-5 µmol/ml, or 50% thereof in case of pediatric use. The dose may be administered periodically as described elsewhere herein. Additionally or alternatively, the agent is preferably not comprised in fecal matter, or, if it is comprised in fecal matter (e.g., as an alternative to the above-mentioned composition), it is enriched, i.e., the amount of the agent is higher than in prior art fecal matter, i.e., at least 1, 2, 3, 4, 5, 6, 7, 8, 9, 10 wt. % higher in comparison to any fecal matter or fecal microbiota transplant to which the agent has not been added. According to the disclosure, the agent can be added to the fecal matter. If the agent is comprised in fecal matter, preferably at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, 200, 300, 400, 500, 600, 700, 800, 900 ng, or at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, 200, 300, 400, 500, 600, 700, 800, 900 µg (microgram), or at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100 mg of the agent is comprised in the fecal matter, for example, per ml or per g fecal matter. Preferably, the agent is the first, second, third, fourth, or fifth most dominant metabolite in the fecal matter, i.e., has the highest weight amount in comparison to other metabolites contained in the fecal matter, or is at least in the top 10, or top 5.

The agent(s) according to the disclosure may be used in any combination in the prevention or treatment of an autoimmune disease as described herein. For example, the *Desulfovibrio* species may be combined with the chloro, fluoro or bromo-substituted tryptophan, e.g., 6-BT, and/or with the mono or di fatty acid substituted glycerol phosphocholine (GPC), e.g., with MA-GPC or with A-GPC. Alternatively, the chloro, fluoro or bromo-substituted tryptophan, e.g., 6-BT may be combined with the mono or di fatty acid substituted glycerol phosphocholine (GPC), e.g., with MA-GPC or with A-GPC. Or alternatively, MA-GPC may be combined with A-GPC.

The agent(s) according to the disclosure may modulate the immune system—by resetting B cell clone function and regulatory T-cells, which in turn may inhibit autoimmune response.

Preferably, the agent(s) according to the disclosure is not comprised or combined with fecal matter, although the agent(s) may be derived therefrom. Additionally or alternatively, the agent(s) may be comprised in a composition comprising not more than 100, 90, 80, 70, 60, 50, 40, 30, 20, 10, 9, 8, 7, 6, 5, 4, 3, 2, 1 bacterial species.

Preferably, the agent(s) according to the disclosure is comprised in a (pharmaceutical) composition in an amount of at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 40, 50, 60, 70, 80, 90, 100, or between 0.1-10, 0.5-15, 1-20, 1-100 mg, between 5-50 mg, or between 1-25 mg, for example, per g or per ml of the composition or carrier (e.g., an aqueous solution with 0.5-1.5 wt. % NaCl, e.g., 0.9 wt. % NaCl, particularly in case of intravenous administration).

The prevention and/or treatment according to the disclosure may involve administering the agent(s) orally, or to the small intestine, preferably the duodenum, of the subject. In this regard, the fecal matter may be administered by enteral, preferably by oral, nasal or rectal administration, and/or by duodenal administration such as by means of a (naso) duodenal tube. Also foreseen is intravenous administration and subcutaneous administration (e.g., by match stick size (4×44 mm) implant device subcutaneous delivery system for delivering and effective and consistent chronic dose for 3-6 months treatment (after which it is replaced again)), in particular, for any one of the agent(s) substituted amino acid according to the disclosure, and particularly for GPC according to the disclosure, e.g., MA-GPC and A-GPC.

The agent(s) according to the disclosure may be administered to the gastrointestinal tract of the subject, preferably the small intestine, most preferably the duodenum, of the subject. The duodenum is the first section of the small intestine in most higher vertebrates, including mammals. The duodenum precedes the jejunum and ileum and is the shortest part of the small intestine. In humans, the duodenum is a hollow tube of 25-38 cm that connects the stomach to the distal duodenum. It begins with the duodenal bulb and ends at the suspensory muscle of duodenum. Although it is also possible to administer the agent(s) to the colon (or cecum) of the subject, administration to the colon (or cecum) of the subject is preferably not encompassed by the disclosure.

The agent(s) according to the disclosure may be combined with bacteria, i.e., microbiota or intestinal microbial cells, wherein the phylum may be one (or a combination) chosen from the group consisting of:

Firmicutes, such as belonging to the genera *Eubacterium, Intestinimonas, Faecalibacterium, Christensenella, Anaerostipes*, Agathobacter, *Roseburia, Coprococcus, Clostridium, Subdoligranulum, Anaerotruncus*, Flavinobacter, *Ruminococcus, Butyricicoccus*, Butyrovibrio, *Sporobacter*, Papilibacter, Oscillobacter, Oscillospora, Veilonella, *Lactobacillus, Streptococcus;*

Proteobacteria such as belonging to the genera *Escherichia* or *Enterobacter;*

Actinobacteria such as belonging to the genera *Bifidobacterium* or Colinsella;

Bacteroidetes such as belonging to the genera *Bacteroides, Prevotella* or Alistipes; and/or Verrucomicrobia such as belonging to the genus *Akkermansia.*

The agent(s) may also be combined with microbiota or intestinal microbial cells chosen from Eukarya, Archaea, and Bacteria, preferably chosen from the group of $10^{57}$ species as disclosed by Rajilić-Stojanović and de Vos (2014 FEMS Microbiol. Rev. 38(5):996-$10^{47}$).

A total of between $10^4$ and $10^{16}$, $10^4$ and $10^{15}$, $10^4$ and $10^{14}$, $10^6$ and $10^{12}$, preferably between $10^8$ and $10^{10}$, of any of the above-mentioned microbial cells may preferably be used, e.g., per ml or per mg carrier.

The agent(s) may be applied in an effective amount, i.e., a quantity sufficient to achieve a desired therapeutic and/or prophylactic effect, e.g., an amount that results in the treatment and/or prevention of the respective condition. In the context of therapeutic or prophylactic applications, the amount to be administered to the subject may depend on the type and severity of the disease or condition and on the characteristics of the subject, such as general health, age, sex, body weight and tolerance to drugs. It may also depend on the degree, severity and type of disease or condition. The skilled artisan will be able to determine appropriate dosages depending on these and other factors.

In a preferred embodiment, the prevention and/or treatment according to the disclosure involves at least 1, 2, 3, 4, 5, 6, 7, 8, 9, 10, and/or at most 10, 20, 30, 40, 50 separate administrations of the agent(s), preferably with intervals of at least 1, 2, 3, 4, 5, 6, 7, 8, 10, and/or at most 10, 20, 30, 40, 50 weeks between the separate administrations. The prevention and/or treatment may also involve daily, weekly, monthly administrations, such as once or twice within every 1, 2, 3, 4, 5, 6, 7, 8, 9, 10 days/weeks/months and/or may be during a period of at least 1, 2, 3, 4, 5, 6, 7, 8, 9, 10, 20, 30, 40, 50 weeks (or months or even years).

The agent(s) may be comprised in liquid medium and/or are preferably not combined with (e.g., in a composition comprising) solids having a diameter of more than 1, 2, 3, 4, 5, 10, 15, 20, 25, 50, 75, 100, 200, 400, 600, 800, or 1000 μm. The liquid medium may be an aqueous solution with 0.5-1.5 wt. % NaCl, e.g., 0.9 wt. % NaCl. With the term "solids" is means discrete particles with at most 30, 20, 10, 5, 1 wt. % water.

It is further envisaged that the agent(s) according to the disclosure is comprised in a composition, preferably a pharmaceutical composition, more preferably a liquid or solid dosage form, most preferably a capsule, a tablet, or a powder.

For oral administration, the agent(s) may be administered in solid dosage forms, such as capsules, tablets, and powders, or in liquid dosage forms, such as elixirs, syrups, and suspensions. Also, a carrier can be applied, such as activated carbon.

The agent(s) may be used as medicament and/or accompanied by a physiologically acceptable carrier, which may be any inert carrier. For instance, non-limiting examples of suitable physiologically or pharmaceutically acceptable carriers include any well-known physiological or pharmaceutical carriers, buffers, diluents, and excipients. It will be appreciated that the choice for a suitable physiological carrier will depend upon the intended mode of administration of the composition as taught herein (e.g., oral) and the intended form of the composition (e.g., beverage, yogurt, powder, capsules, and the like). The skilled person knows how to select a physiologically acceptable carrier, which is suitable for or compatible with the compositions for use as taught herein.

It is particularly preferred that the agent(s) is comprised in and/or encapsulated by an (enteric) coating, preferable wherein the coating does not dissolute and/or disintegrate in the gastric environment of the subject. Such coating may help the agent(s) to reach the intended site for delivery, e.g., the duodenum, without suffering breakdown due to the acidic environment of the stomach. Preferred (enteric) coatings work by presenting a surface that is stable at the highly acidic pH found in the stomach, but breaking down more rapidly at a lower pH. For example, it will not dissolve in the gastric acids of the stomach (pH ~3), but it will dissolve in the alkaline (pH 7-9) environment present in the small intestine, or duodenum.

In an embodiment, the agent(s) according to the disclosure may be combined with, or comprised in a composition comprising, a mucosal binding agent. The term "mucosal binding agent" or "mucosal binding polypeptide" as used herein refers to an agent or a polypeptide that is capable of attaching itself to the gut mucosal surfaces of the gut mucosal barrier of a mammal (e.g., human). A variety of mucosal binding polypeptides have been disclosed in the art. Non-limiting examples of mucosal binding polypeptide include bacterial toxin membrane binding subunits including such as the B subunit of cholera toxin, the B subunit of the *E. coli* heat-labile enterotoxin, *Bordetella pertussis* toxin subunits S2, S3, S4 and/or S5, the B fragment of Diphtheria toxin and the membrane binding subunits of Shiga toxin or Shiga-like toxins. Other suitable mucosal binding polypeptides include bacterial fimbriae proteins such as including *E. coli* fimbriae (K88, K99, 987P, F41, FAIL, CFAIII ICES1, CS2 and/or CS3, CFAIIV ICS4, CS5 and/or CS6), P fimbriae, or the like. Other non-limiting examples of fimbriae include *Bordetella pertussis* filamentous hemagglutinin, *Vibrio cholerae* toxin-coregulate pilus (TCP), Mannose-sensitive hemagglutinin (MSHA), fucose-sensitive hemagglutinin (PSHA), and the like. Still other mucosal-binding agents include viral attachment proteins including influenza and sendai virus hemagglutinins and animal lectins or lectin-like molecules including immunoglobulin molecules or fragments thereof, calcium-dependent (C-type) lectins, selectins, collectins or *Helix pomatia* hemagglutinin, plant lectins with mucosa-binding subunits include concanavalin A, wheat-germ agglutinin, phytohemagglutinin, abrin, ricin and the like.

In an embodiment, a composition comprising the agent(s) for use as taught herein may be in liquid form, e.g., a stabilized suspension comprising one or more of the agent(s), in solid form, e.g., a powder of lyophilized agent(s) as taught herein. For example, a cryoprotectant such as lactose, trehalose or glycogen may be employed.

Optionally, the agent(s) according to the disclosure may be encapsulated in capsules such as gelatin capsules, possibly together with inactive ingredients and powder carriers, such as e.g., glucose, lactose, sucrose, mannitol, starch, cellulose or cellulose derivatives, magnesium stearate, stearic acid, sodium saccharin, talcum, magnesium carbonate and the like.

In an embodiment, the agent(s) according to the disclosure may comprise one or more ingredients, which are suitable for promoting survival and/or viability and/or maintaining the integrity of the agent(s) e.g., during storage and/or during exposure to bile and/or during passage through the gastrointestinal tract of a mammal (e.g., a human). Non-limiting examples of such ingredients include an enteric coating as described herein before, and/or controlled release agents allowing passage through the stomach. The skilled person knows how to select suitable ingredients for ensuring that the fecal matter reaches its intended destination, where it exerts its action.

In an embodiment, the compositions comprising the agent(s) for use as taught herein may further comprise ingredients selected from the group consisting of prebiotics, probiotics, carbohydrates, polypeptides, lipids, vitamins, minerals, medicinal agents, preservative agents, antibiotics, or any combination thereof.

In a particularly preferred embodiment, the agent(s) according to the disclosure is combined with bacteria from the genus *Eubacterium*, Intestinimonas, Bifidobacteria, Lactobacillales and/or *Akkermansia*, preferably chosen from the group consisting of *Bifidobacterium animalis* sub *lactis* or *Bifidobacterium breve, Lactobacillus plantarum. Lactobacillus rhamnosus, Lactobacillus acidophilus, Eubacterium hallii*, Intestinimonas butyriciproducens, and/or *Akkermansia muciniphila*. A total of between $10^4$ and $10^{14}$, $10^6$ and $10^{12}$, preferably between $10^8$ and $10^{10}$, of such bacterial cells may preferably be used (e.g., per ml or per mg). The above-mentioned combination may provide for synergistic effects. The agent(s) and the bacteria may be comprised in different compositions, or together within a single composition (such as in a capsule or other dosage form as described herein).

The agent(s) according to the disclosure may additionally or alternatively be combined with hormone suppletion (thyroid, hydrocortisone, insulin, etc.), tumor necrosis factor alpha (TNFα) inhibitor, and/or DMARDs (rheumatoid arthritis) preferably chosen from the group consisting of infliximab, adalimumab, certolizumab pegol, and golimumab. It is considered that treatment with a TNFα inhibitor may increase the response to treatment with agent(s) according to the disclosure, and/or vice versa that treatment with agent(s) according to the disclosure may increase the response to treatment with a TNFα inhibitor. Preferably, the TNFα inhibitor is administered in a different or the same composition as the agent(s) (such as in a capsule or other dosage form as described herein). The TNFα inhibitor may be administered at least (or at most) 1, 2, 3, 4 times weekly or daily and/or intravenously/orally in a dose of, for example, 1-10, 2-8, 3-7, 4-6, or 5 mg/kg.

It is further envisaged that the agent(s), particularly the *Desulfovibrio* species, for use according to the disclosure is present in lyophilized and/or microencapsulated form, e.g., a capsule comprising said. Preferably, said agent(s), e.g., *Desulfovibrio* species, is present in solid, lyophilized or dried form (i.e., containing less than 20, 10, 5, 2, 1, wt. % water), for example, in powder or granular form. For example, it may be present in microencapsulated form. The skilled person is capable of lyophilizing or microencapsulating the agent(s) based on well-known techniques, wherein oxygen-free conditions may be applied to preserve viability of any bacteria contained in the fecal matter.

The technique of microencapsulation is well-known in the art for preserving bacteria (e.g., as reviewed by Serna-Cock and Vallejo-Castillo, 2013, Afr. J. of Microbiol. Res., 7(40): 4743-4753). For example, any of the preservation techniques and preservation systems taught by Serna-Cock and Vallejo-Castillo may be employed in the disclosure.

Lyophilization methods include, without limitation, slow, gradual freezing to −40° C. before drying, rapid freezing by placing at −80° C. before drying, or ultra-rapid freezing by dripping cells with cryoprotectant in liquid nitrogen before drying. Cryoprotectants are often employed to protect compositions during lyophilization and to enhance shelf-life. Without limitation, a cryoprotectant selected from the group consisting of sucrose, maltose, maltodextrin, trehalose, mannitol, sorbitol, inulin, glycerol, DMSO, ethylene glycol, propylene glycol, 2-methyl-2,4-pentanediol, polyethylene glycol, polyvinylpyrrolidone, polyvinyl alcohol, polyglycerol, skim milk powder, milk protein, whey protein, UHT milk, betaine, adonitol, sucrose, glucose, lactose or any combination thereof, may be employed.

Prebiotics such as starch and wheat bran may further be added to the agent(s) of the disclosure, e.g., before lyophilization to enhance the efficacy thereof. Addition of antioxidants such as riboflavin, riboflavin phosphate or a physiologically acceptable salt thereof, glutathione, ascorbate, glutathion and cysteine to the lyophilization mixture may further enhance the viability of any bacteria contained.

The agent(s), particularly the *Desulfovibrio* species can be stored for long time (e.g., at least 10, 20, 40 52 weeks or at least 1, 2, 3 years) after addition of a cryoprotectant as disclosed herein, for example, glycerol and/or freezing at −80° C. In addition, or alternatively, freeze drying stabilizes the agent(s) over such period. Finally, one may also inoculate the *Desulfovibrio* species as described by de Vos (2013 Microb. Biotechnol. 2013 July; 6(4):316-25).

In an embodiment, the agent(s) for use as taught herein may be, or may be comprised in, a food or food supplement composition. Such food or food supplement composition may include a dairy product, more preferably a fermented dairy product, preferably a yogurt or a yogurt drink.

In an embodiment, the agent(s), or compositions comprising the, for use as taught herein may further comprise one or more ingredients, which further enhance the nutritional value and/or the therapeutic value of the fecal matter as taught herein. For instance, it may be advantageous to add one or more ingredients (e.g., nutritional ingredients, veterinary or medicinal agents, etc.) selected from proteins, amino acids, enzymes, mineral salts, vitamins (e.g., thiamine HCl, riboflavin, pyridoxine HCl, niacin, inositol, choline chloride, calcium pantothenate, biotin, folic acid, ascorbic acid, vitamin B12, p-aminobenzoic acid, vitamin A acetate, vitamin K, vitamin D, vitamin E, and the like), sugars and complex carbohydrates (e.g., water-soluble and water-insoluble monosaccharides, disaccharides, and polysaccharides), medicinal compounds (e.g., antibiotics), antioxidants, trace element ingredients (e.g., compounds of cobalt, copper, manganese, iron, zinc, tin, nickel, chromium, molybdenum, iodine, chlorine, silicon, vanadium, selenium, calcium, magnesium, sodium and potassium and the like). The skilled person is familiar with methods and ingredients that are suitable to enhance the nutritional and/or therapeutic/medicinal value.

The disclosure also provides for a method for predicting an autoimmune disease patient's response to therapy by agent(s) according to the disclosure (or by autologous fecal matter), the method comprising:

measuring level of abundance in the patient's fecal microbiota of at least one *bacterium* chosen from the group consisting of *Bacteroides* caccae and *Coprococcus catus,* wherein a measured level higher than a reference level indicates that the autoimmune disease patient is responsive to the therapy. The reference level may, for example, be a level of between 50-150%, preferably between 75-125, more preferably between 90-120, 95-110, 98-10$^5$% of the level of abundance in healthy control subject(s) fecal microbiota of the at least one *bacterium* chosen from the group consisting of *Bacteroides* caccae and *Coprococcus catus.*

In the context of the disclosure, the subject receiving the treatment is preferably an animal, more preferably a mammal, most preferably a human. As will be clear, the present treatment is preferably not performed as control or placebo treatment and/or within a clinical trial, i.e., a study in which participants are assigned to groups that either receive one or more intervention/treatment, one or more control or placebo intervention/treatment, or no intervention, so that researchers can evaluate the effects of the interventions on biomedical or health-related outcomes.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one."

"Sequence identity" can be determined by alignment of two peptide or two nucleotide sequences using alignment algorithms (when optimally aligned by, for example, the programs GAP or BESTFIT using default parameters). GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or EmbossWin version 2.10.0 (using the program "needle"). Alternatively, percent similarity or identity may be determined by searching against databases, using algorithms such as FASTA, BLAST, etc. As an illustration, by a polynucleotide having a nucleotide sequence having at least, for example, 95% "identity" to a reference nucleotide sequence encoding a polypeptide of a certain sequence, it is intended that the nucleotide sequence of the polynucleotide is identical to the reference sequence except that the polynucleotide sequence may include up to five point mutations (which may be (conservative) substitutions, deletions and/or insertions) per each 100 nucleotides of the reference polypeptide sequence. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence. Similarly, by a polypeptide having an amino acid sequence having at least, for example, 95% "identity" to a reference amino acid sequence of SEQ ID NO:1 is intended that the amino acid sequence of the polypeptide is identical to the reference sequence except that the polypeptide sequence may include up to five amino acid alterations per each 100 amino acids of the reference amino acid of SEQ ID NO:1. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence. Sequence identity can be determined over the entire length of the sequence(s) to be considered.

BRIEF DESCRIPTION OF THE DRAWINGS

FIG. 2A: Top 10 metabolites that best predicted treatment group allocation (XGBoost predictive modeling algorithm). Percentages are scaled toward the largest, which is set at 100%. Top 3 metabolites stand out with higher relative importance in the analysis.

FIGS. 2B-2D: Relative abundance of top 3 metabolites plotted against time for each treatment group (in each graph, the line that is predominantly the upper line represents the autologous FMT group; the line that is predominantly the bottom line represents the allogenic FMT group). Medians+-IQR are reported. P-values were calculated using Mann-Whitney U test between groups at 12 months. 1-myristoyl-2-arachidonoyl-GPC is different between groups at 12 months, p-value=0.020. 1-arachidonoyl-GPC is different between groups at 12 months, p-value=0.020. FIG. 2E: Spearman correlation between change in fasting C-peptide and change in 1-myristoyl-2-arachidonoyl-GPC. FIG. 2F: Abundance of fecal *D. piger* over time. P-values were calculated using Mann-Whitney U test. At 6 months p-value=0.024, at 12 months p-value=0.023. FIG. 2G: Relative abundance in *D. piger* between the groups. The delta p-value was calculated using Mann-Whitney U test on the delta's between 0 and 12 months for each group, p-value=0.006. FIG. 2H: Fold change in *D. piger* between the groups (the predominant upper line represents the autologous FMT group). The delta p-value was calculated by doing Mann-Whitney U test on the delta's between 0 and 12 months of each group, p-value=0.006. FIG. 2I: Spearman correlation plot of delta (0-12 months) fecal *D. piger* and delta (0-12 months) of fasting C-peptide. FIG. 2J: Correlation plot of fecal *D. piger* and 1-arachidonoyl-GPC. FIG. 2K: Correlation plot of fecal *D. piger* and small intestinal *Prevotella* 1. FIG. 2L: Correlation plot of fecal *D. piger* and small intestinal *Prevotella* 2.

FIG. 4A: Shows the number of responders at 6 months and at 12 months and how many subjects were in each treatment group. Response was defined as <10% decline in C-peptide AUC compared to baseline. The 12 months responders were used for all analyses. FIG. 4B: Shows individual subject lines of C-peptide AUC over time. FIGS. 4C and 4D: show the abundance of *B. caccae* and *C. catus* over time, respectively. In both graphs, the upper line represents responders. P-values were calculated using Mann-Whitney U test between groups at each time point. For *B. caccae* at baseline the p-value=0.0099, for *C. catus* at baseline the p-value=0.00049. FIG. 4E: shows the correlation between delta *C. catus* (0-12 months) and delta C-peptide AUC (0-12 months). Spearman's rho (r) is shown and the p-value was calculated using Spearman's Rank.

in FIGS. 6C and 6E, the upper line represents non responders, the other line responders). Strains that were different between responders and non-responders at baseline or during the course of the study were chosen to display. P-values were calculated using Mann-Whitney U test at each time point. A: *Paraprevotella* spp., p=0.019, B: *Eubacterium ramulus*, p=0.043, C: *Collinsella aerofaciens*, p=0.043, D: *Bacteroides eggerthii*, p=0.006, E:

*Ruminococcus callidus*, p=0.026. *Faecalibacterium prausnitzii* (10th from the top 10), was not significantly different at baseline (p=0.063).

Figure 7:
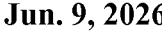
Figure 7:
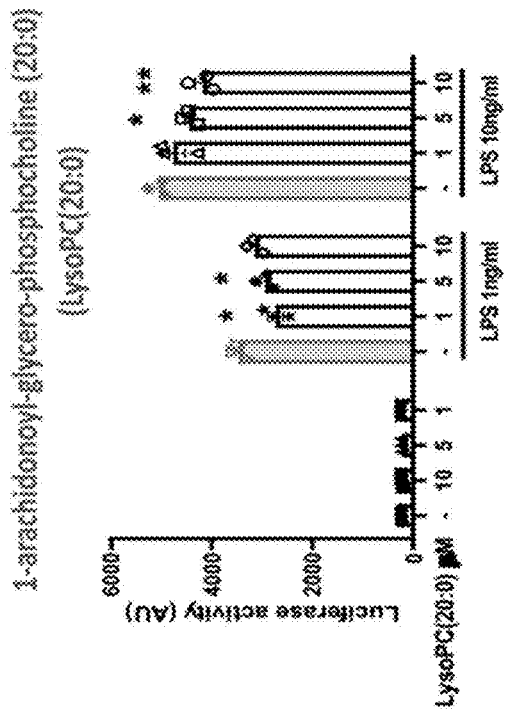
Figure 7:
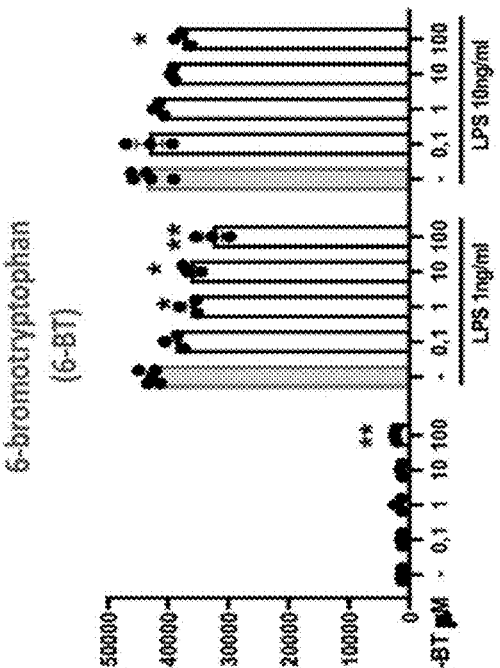

FIG. 7: Effect of 6-bromotryptophan (6-BT), 1-arachidonoyl-glycero-phosphocholine (20:0) (A-GPC), 1-palmitoyl-2-linoleoyl-sn-glycero-3-phosphoethanolamine (16:0-18:2 PE), 1-myristoyl-2-arachidonoyl-glycero-phosphocholine (MA-GPC) on NFκB pathway activation at different doses.

Figure 8:
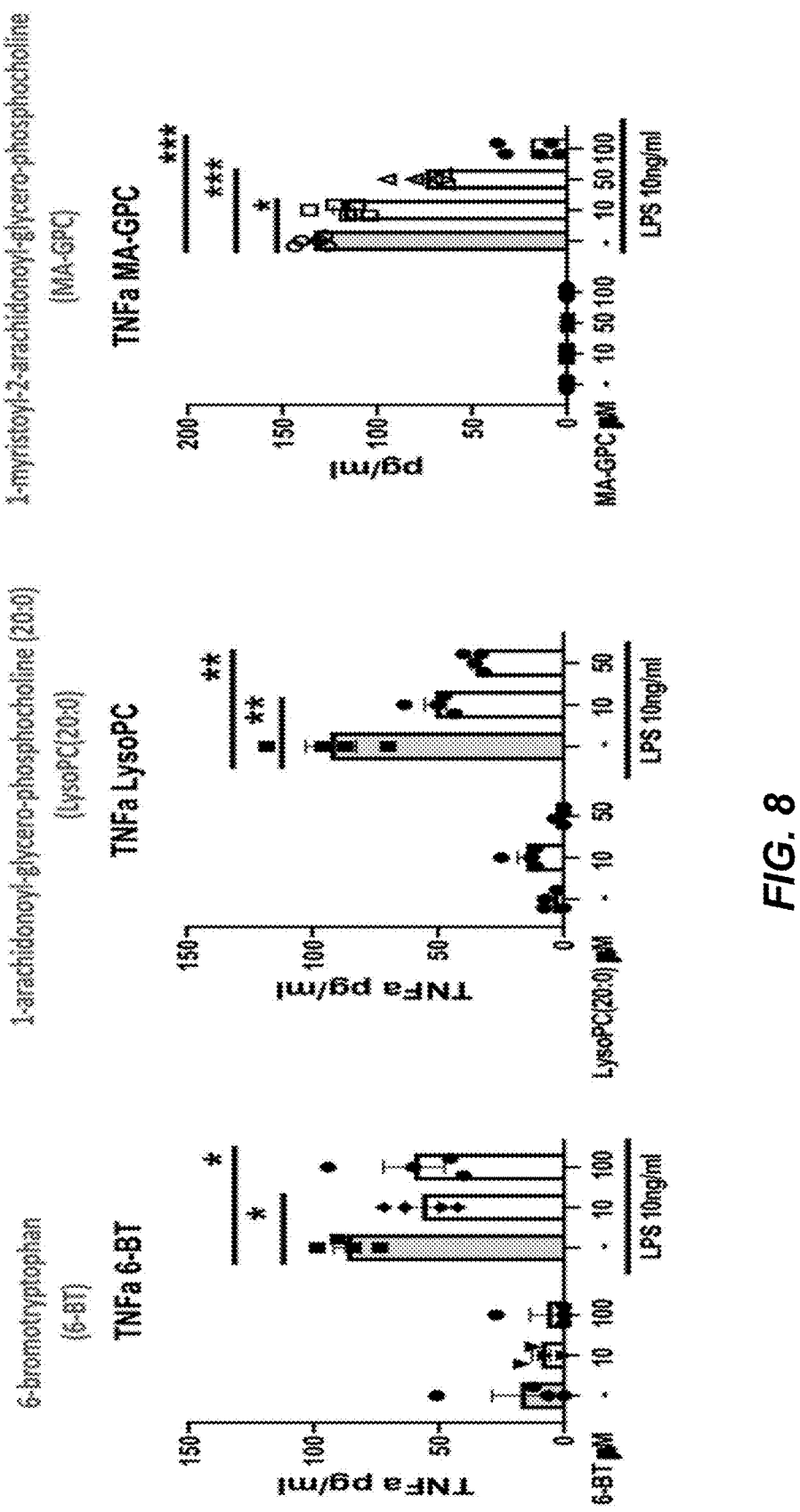

FIG. 8: Effect of 6-BT, MA-GPC, A-GPC on myeloid cells: murine monocytes CD11b+ activated with LPS (10 μg/ml) for 24 hours—TLR4 stimulation.

Figure 9:
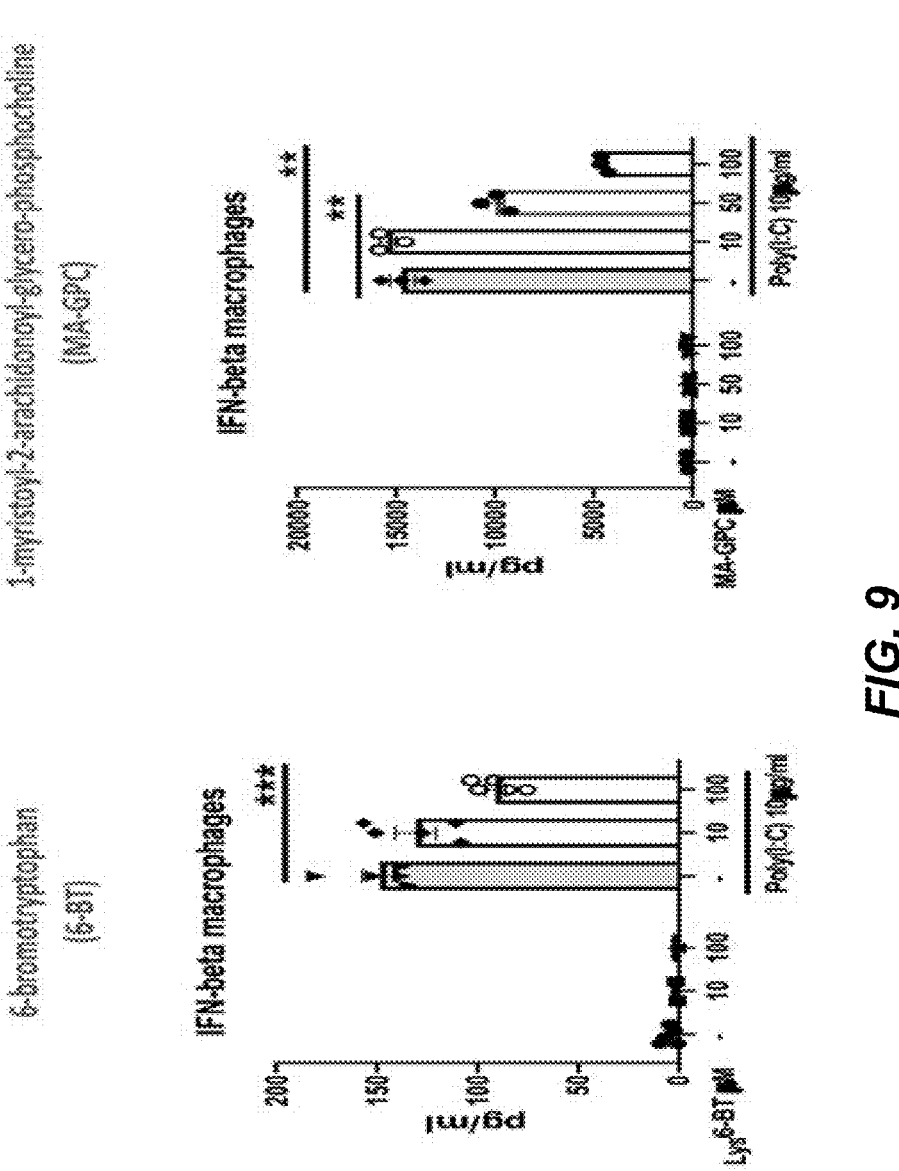

FIG. 9: Effect of 6-BT, MA-GPC, A-GPC on myeloid cells: murine monocytes CD11b+ activated with PolyI:C, analog of dsRNA, for 24 hours—TLR3 stimulation.

Figure 10:
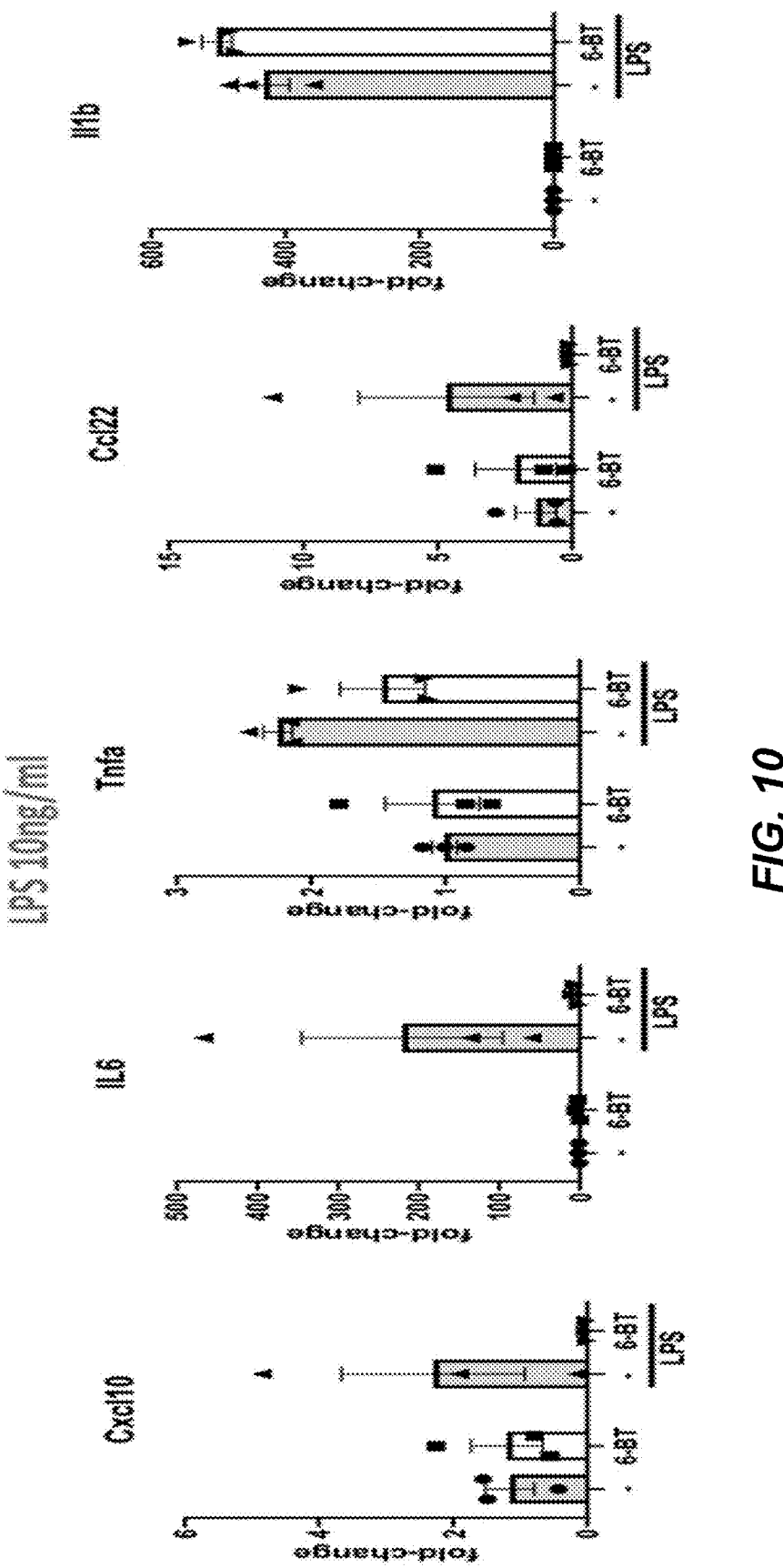

FIG. 10: Effect of 6-BT on human monocytes in LPS stimulation.

Figure 11:
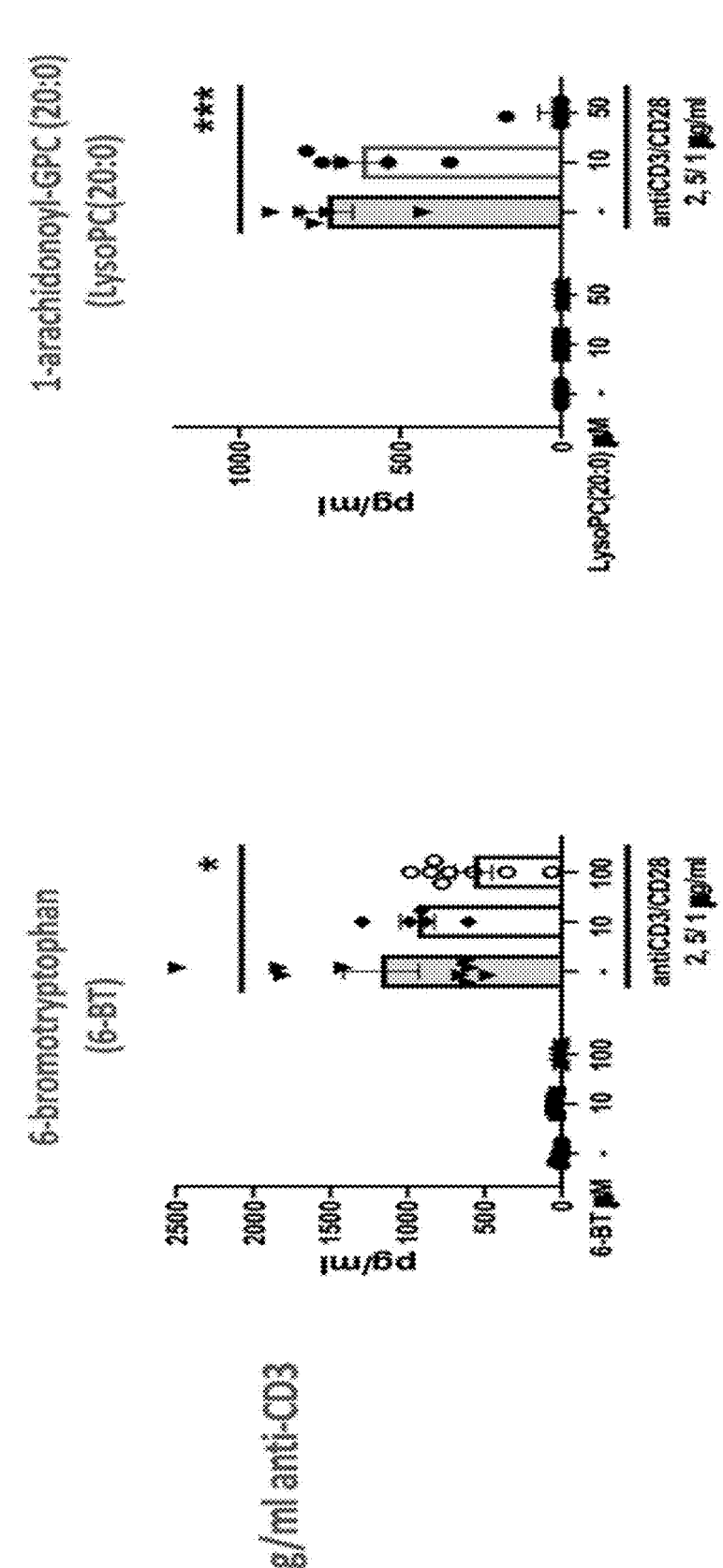

FIG. 11: Effect of 6-BT, A-GPC, MA-GPC on T lymphocytes: murine CD4+ T cells activated with anti-CD3 & anti-CD28 mAbs.

Figure 12:
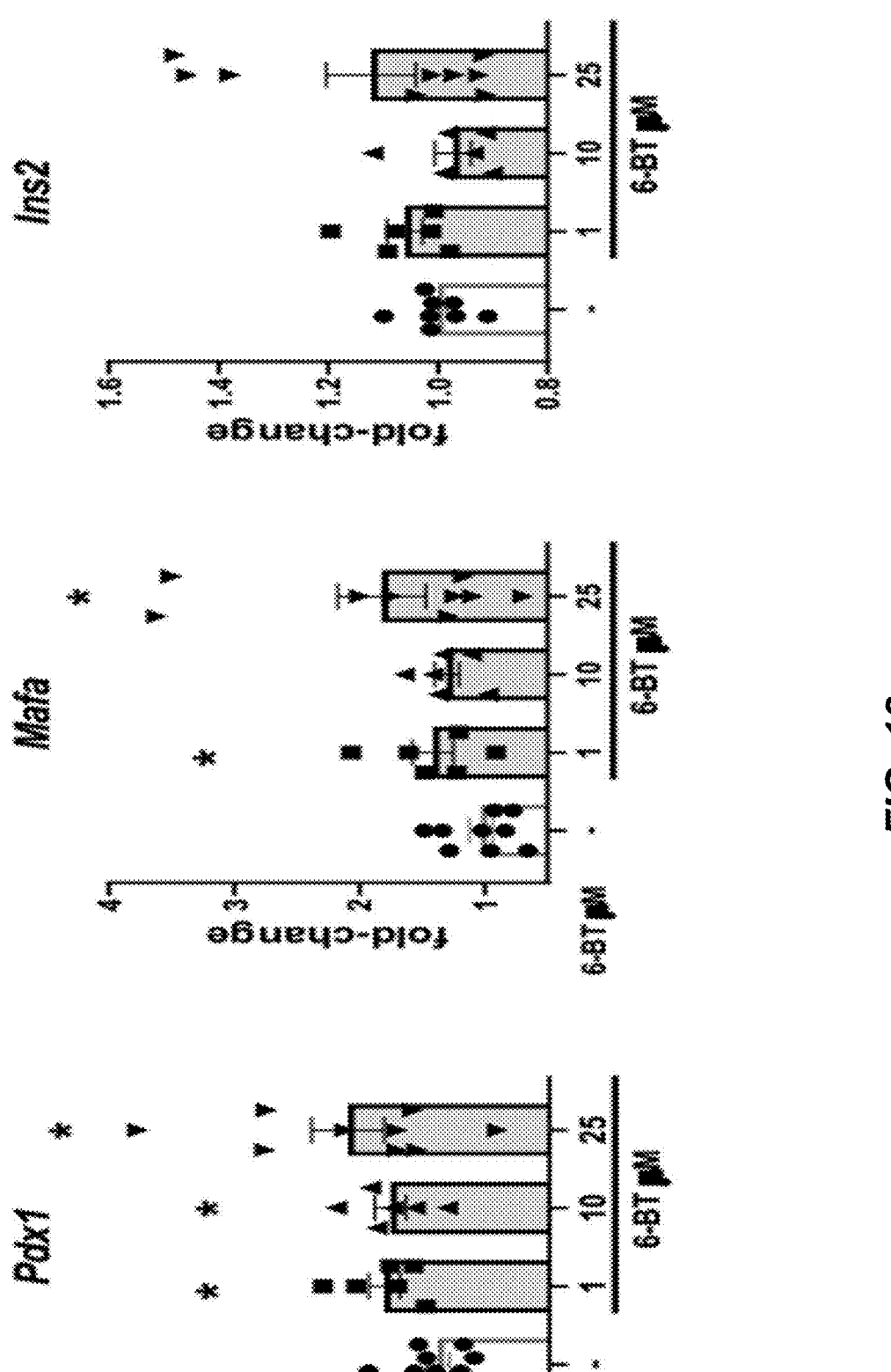

FIG. 12: INS1e beta-cells treated for 24 hours with 6-BT: gene expression of beta cell differentiation markers.

Figure 13:
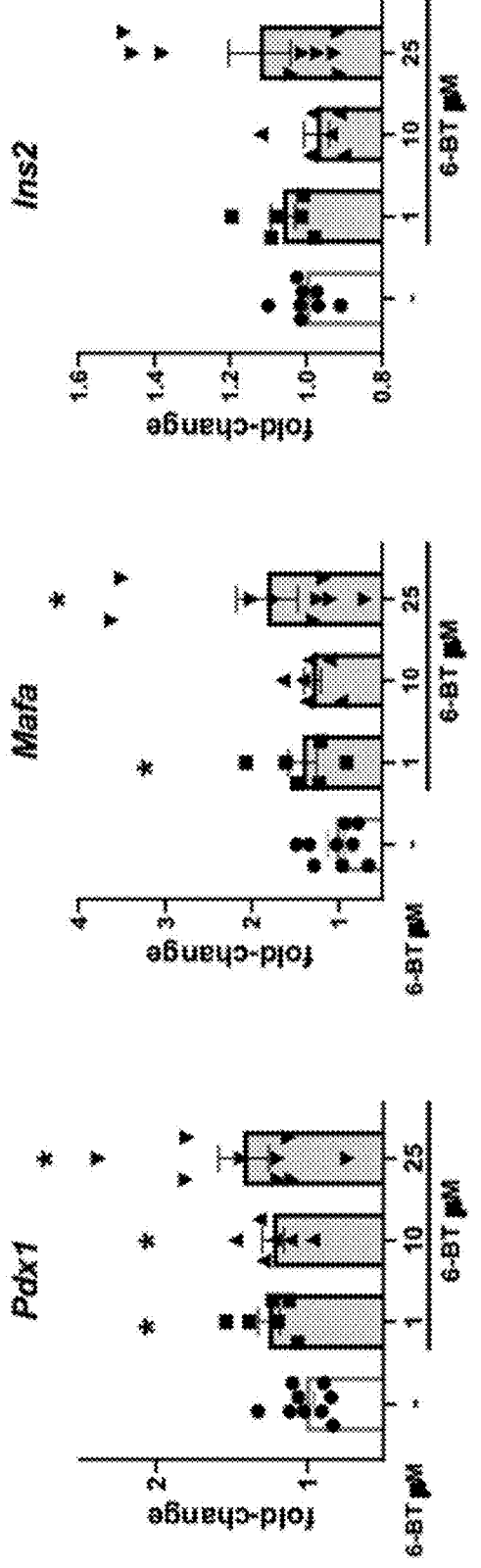
Figure 13:
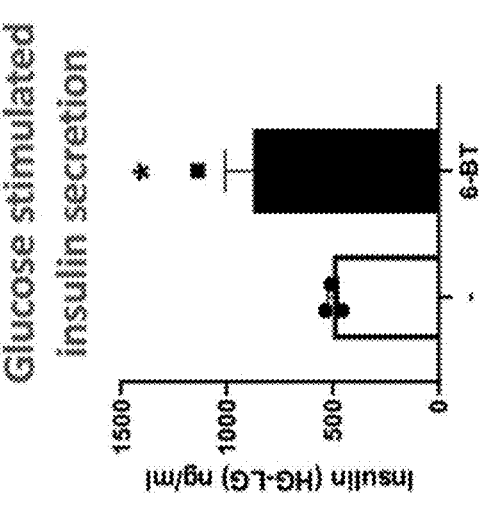
Figure 13:
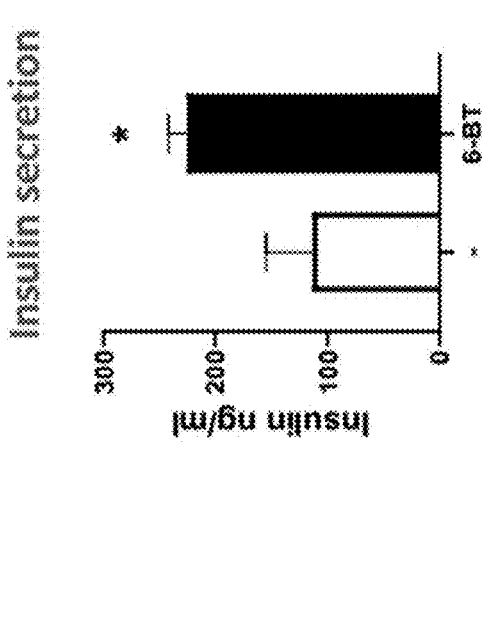

FIG. 13: INS1e beta-cells treated for 24 hours with 6-BT: gene expression of beta cell differentiation markers.

Figure 14:
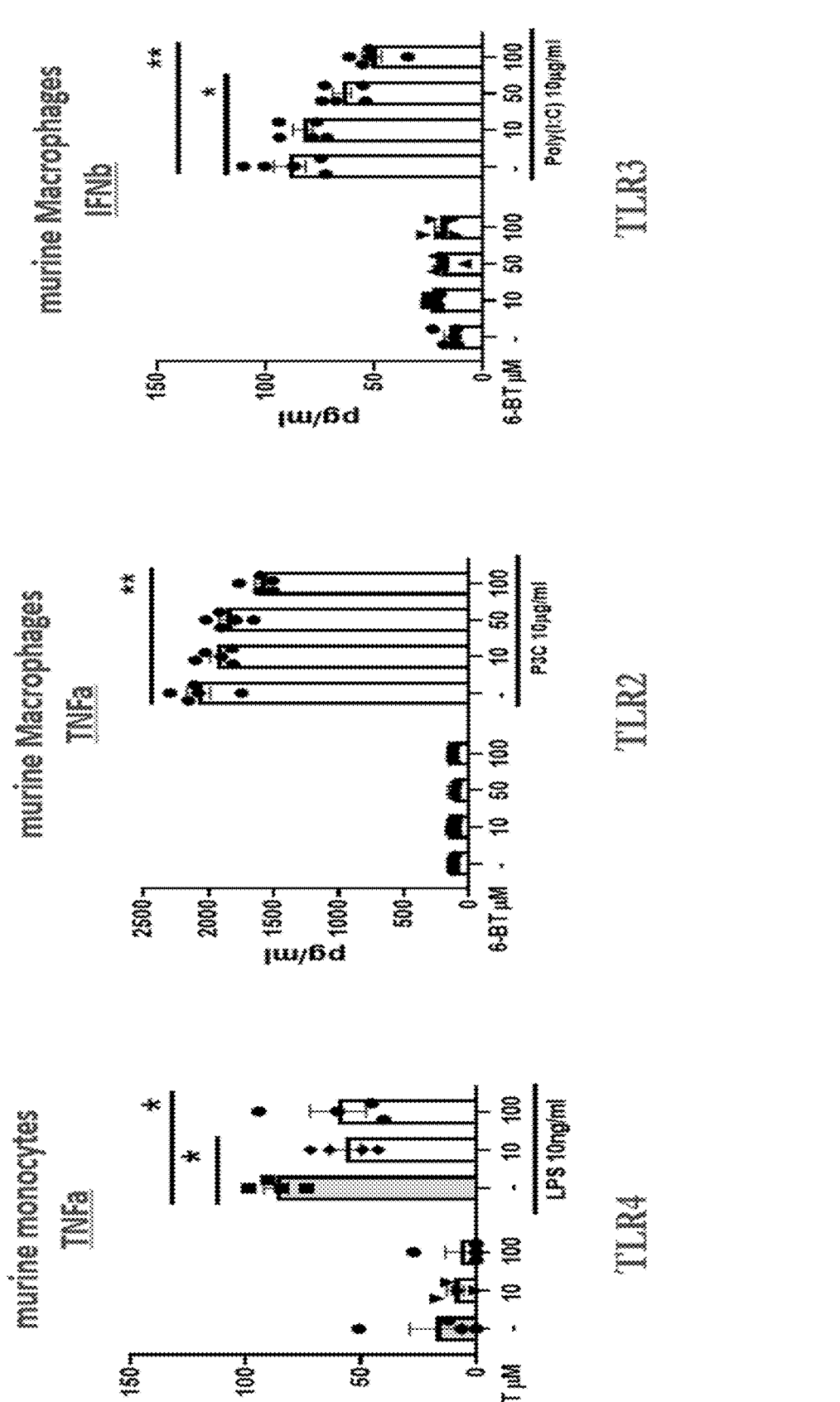

FIG. 14: Murine bone marrow-isolated monocytes (Christ A., Cell 2018) or bone marrow-derived macrophages (Swansen, JEM 2017) were exposed for 24 hours to the indicated concentrations of 6-BT (10-100 μM) in presence or not of 10 μg/ml LPS, 10 μg/ml P3C or 10 μg/ml poly(I:C). By means of ELISA assays, it was found that 6-BT can inhibits the secretion of pro-inflammatory cytokine TNFα upon TLR4 and TLR2 engagements and of IFNbeta upon TLR3 activation.

Figure 15:
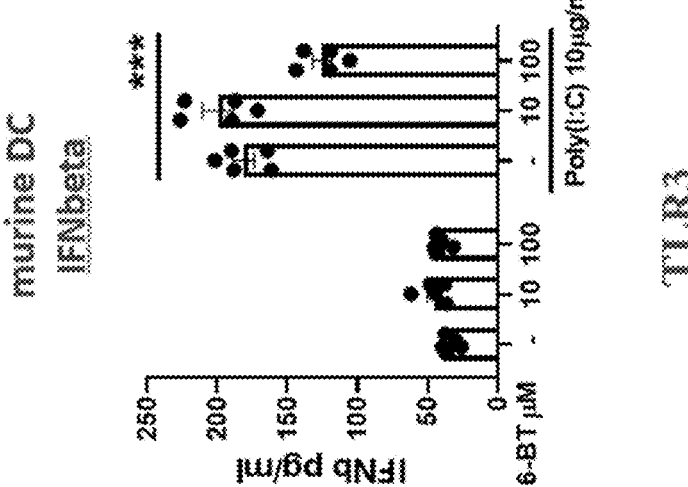
Figure 15:
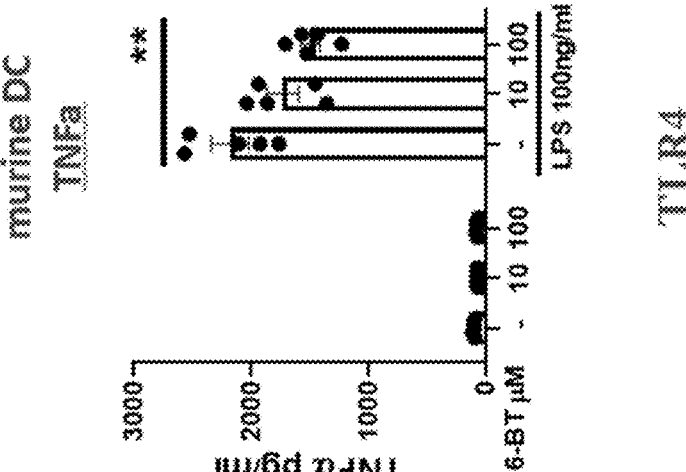

FIG. 15: The effect of 6-BT on murine DC was investigated, differentiated with GM-CSF (40 μg/ml) by bone marrow cells. As for the monocytes/macrophages, 6-BT inhibits the secretion of the pro-inflammatory cytokines TNFα and IFNbeta by DC after activation of, respectively, TLR4 (with 100 μg/ml LPS) or TLR3 (10 μg/ml poly(I:C)).

Figure 16:
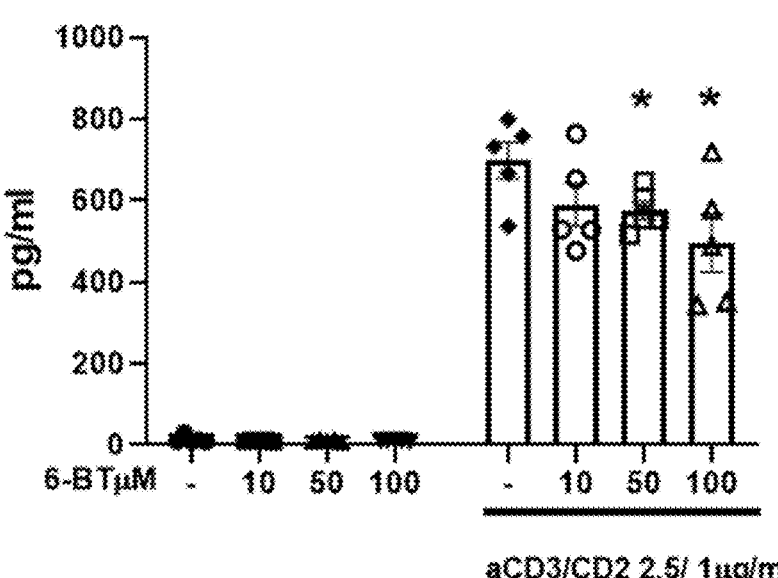

FIG. 16: Further studied was the impact of 6-BT on CD4 T cells. To mimic antigen presentation, murine CD4 T cells (isolated from spleens; Uchimura T., Immunity 2019) were activated by monoclonal antibodies against CD3 and CD28 (2.5 and 1 μg/ml, respectively). In line with the findings on myeloid cells, 6-BT significantly reduced the production of the Th1 cytokine IFNgamma.

Figure 17:
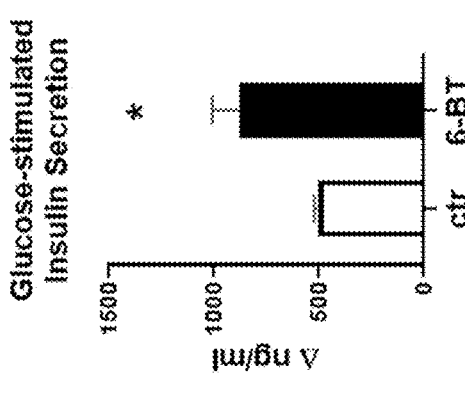
Figure 17:
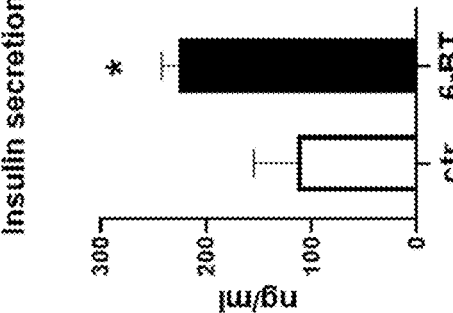
Figure 17:
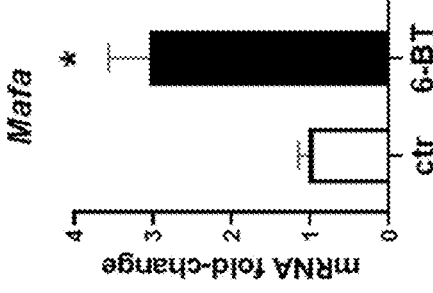
Figure 17:
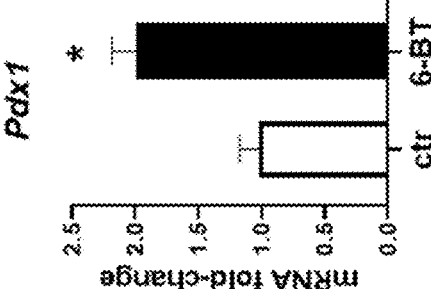

FIG. 17: It was investigated whether 6-BT can exert a direct effect on beta cells. Indeed, here it is seen that 6-BT induces, in IS1E beta cells, the gene expression of the transcription factors PDX1 and MAFA, which are important for beta cell maturation and functionality. In agreement, 6-BT also promoted insulin secretion at steady-state and during glucose-stimulated insulin secretion (data shown as the difference between insulin release at starving condition [1 mM glucose] and at hyperglycemic state [22 mM]), (Paula S., FASEB J. 2015).

Figure 18:
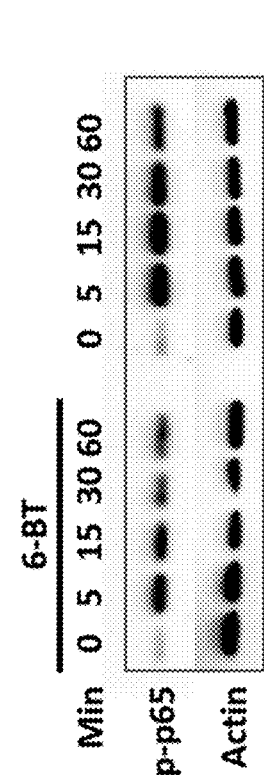
Figure 18:
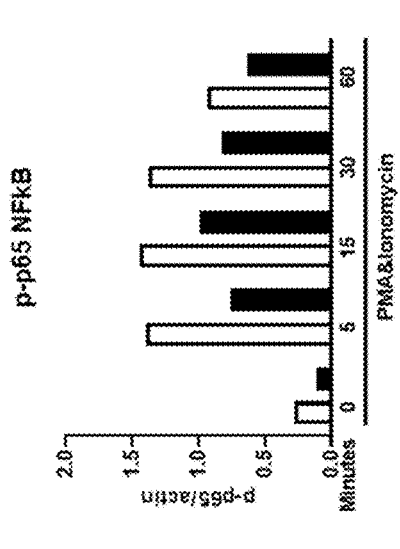

FIG. 18: 6-BT impact on the activation of the NF-kB pathway, a central pathway in all inflammatory diseases (beyond autoimmunity) was checked. Hence, the expression of the phosphorylated form of the p65 subunit was quantified, regarded as a marker of NFkB activation. Upon T cell activation with PMA (50 μg/ml) and ionomycin (1 μg/ml), 6-BT could inhibit, at very early time-points (5-10 minutes after activation), the NF-kB signaling. This effect was found in both murine and human (Jurkat cells) CD4 T cells.

Figure 19:
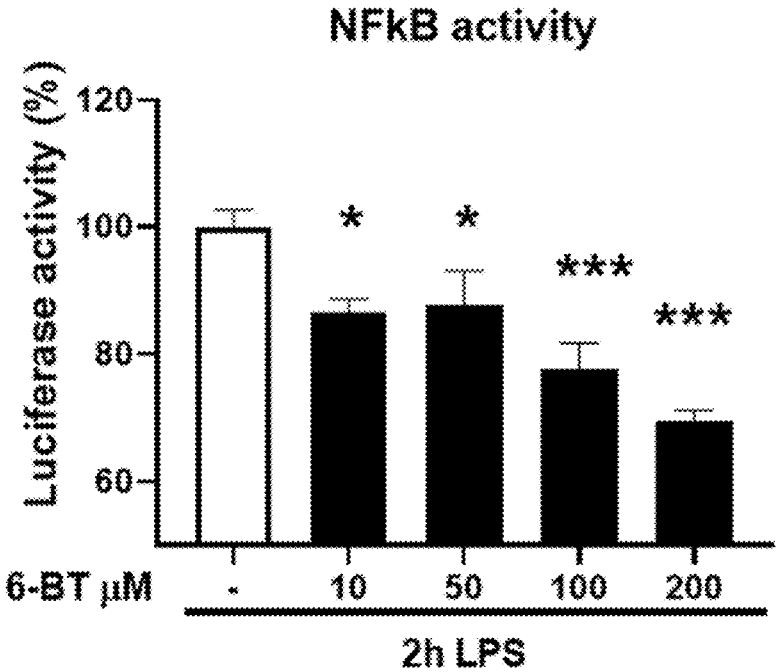

FIG. 19: Using the RAW264.7 murine macrophage cell line stably expressing an NFkB luciferase reporter (Groeneweg M., J. Lipid Res. 2006), overnight exposure of macrophages to 6-BT (10-200 µM) inhibits the transcriptional activity of the NFkB complex in a dose-dependent manner upon 2 hours stimulation with LPS (10 µg/ml).

Figure 20:
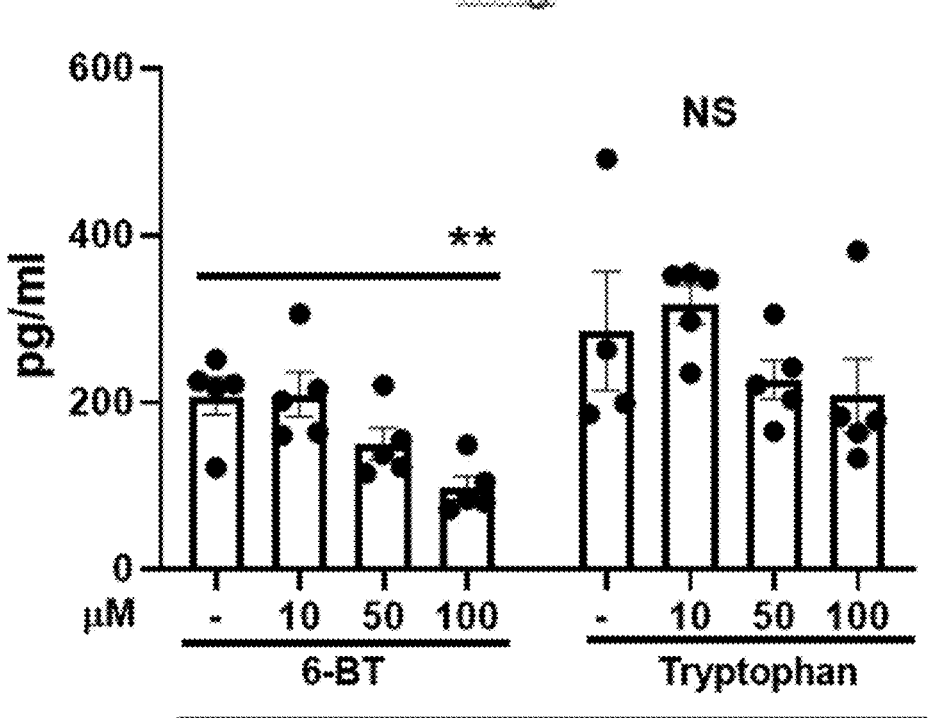
Figure 21:
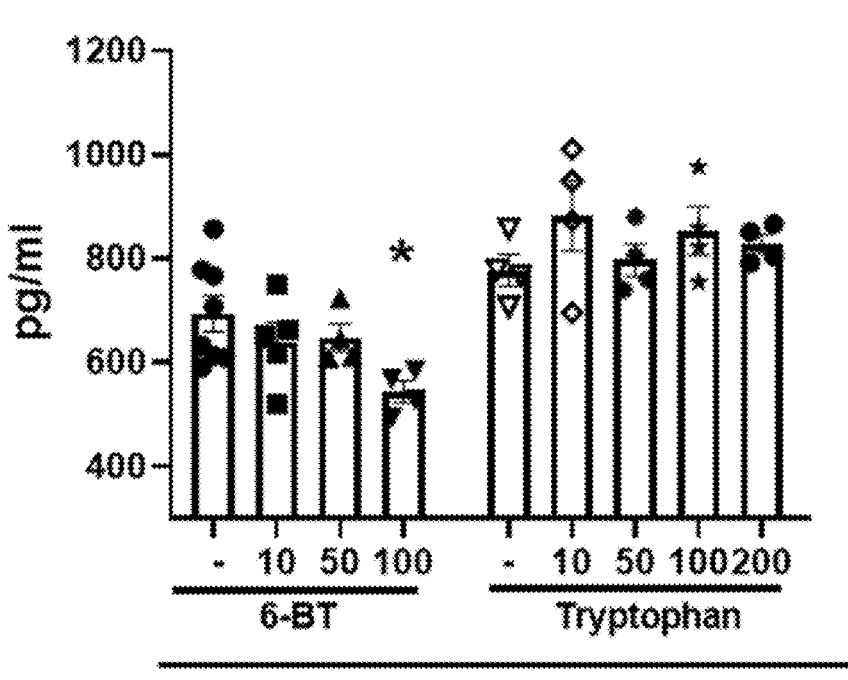

FIG. 20: In murine CD4 T lymphocytes (isolated from murine spleens; Uchimura T., Immunity 2019), 6-BT, but not tryptophan, exerted inhibitory effect on IFNgamma production upon CD3/CD28 engagement. This indicates that 6-BT and tryptophan elicit distinct biological activities.

Figure 2A:
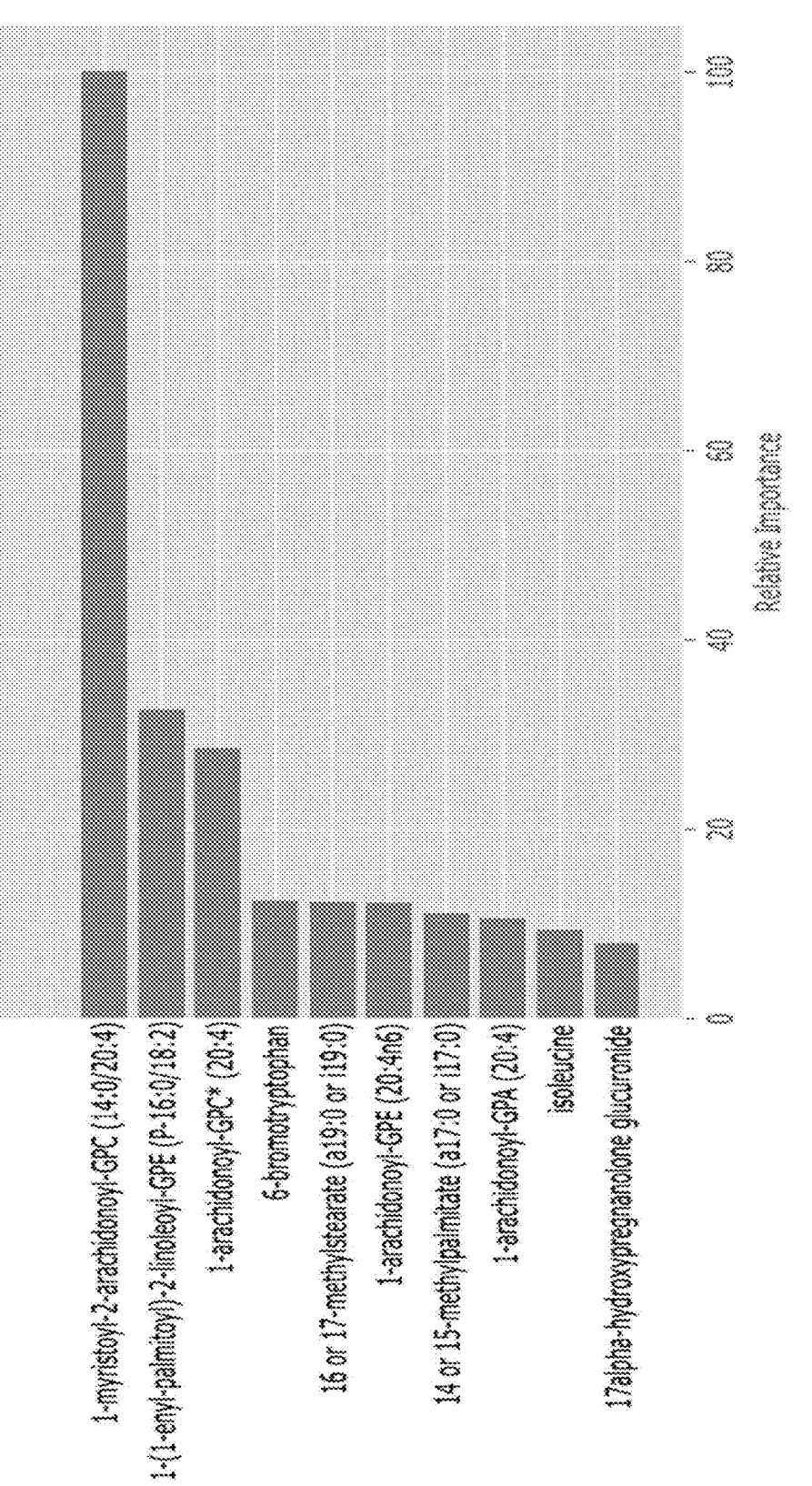
FIGS. 2A-2L.
Figures 2B, 2C, 2D:
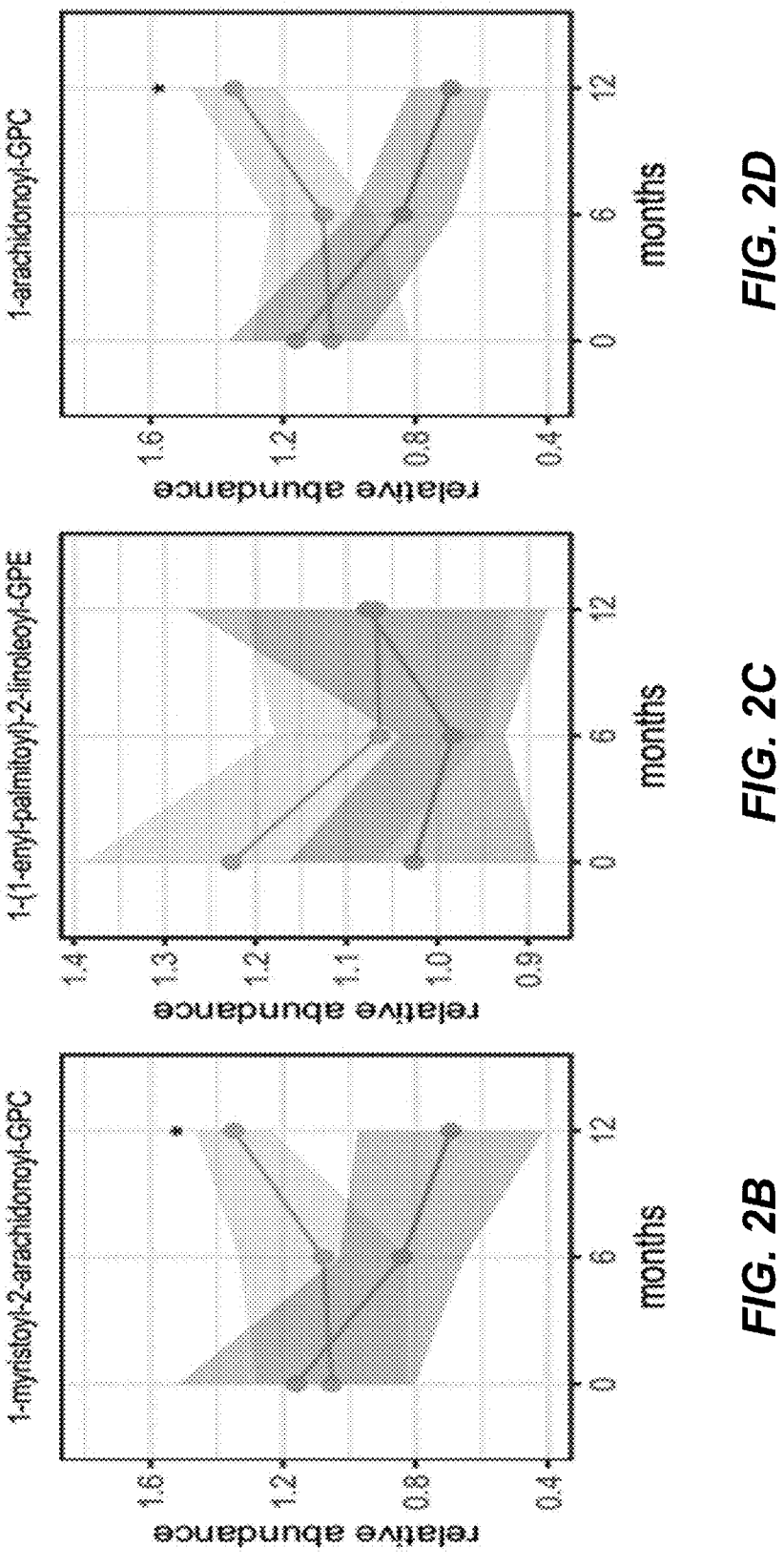
Figures 2E, 2F:
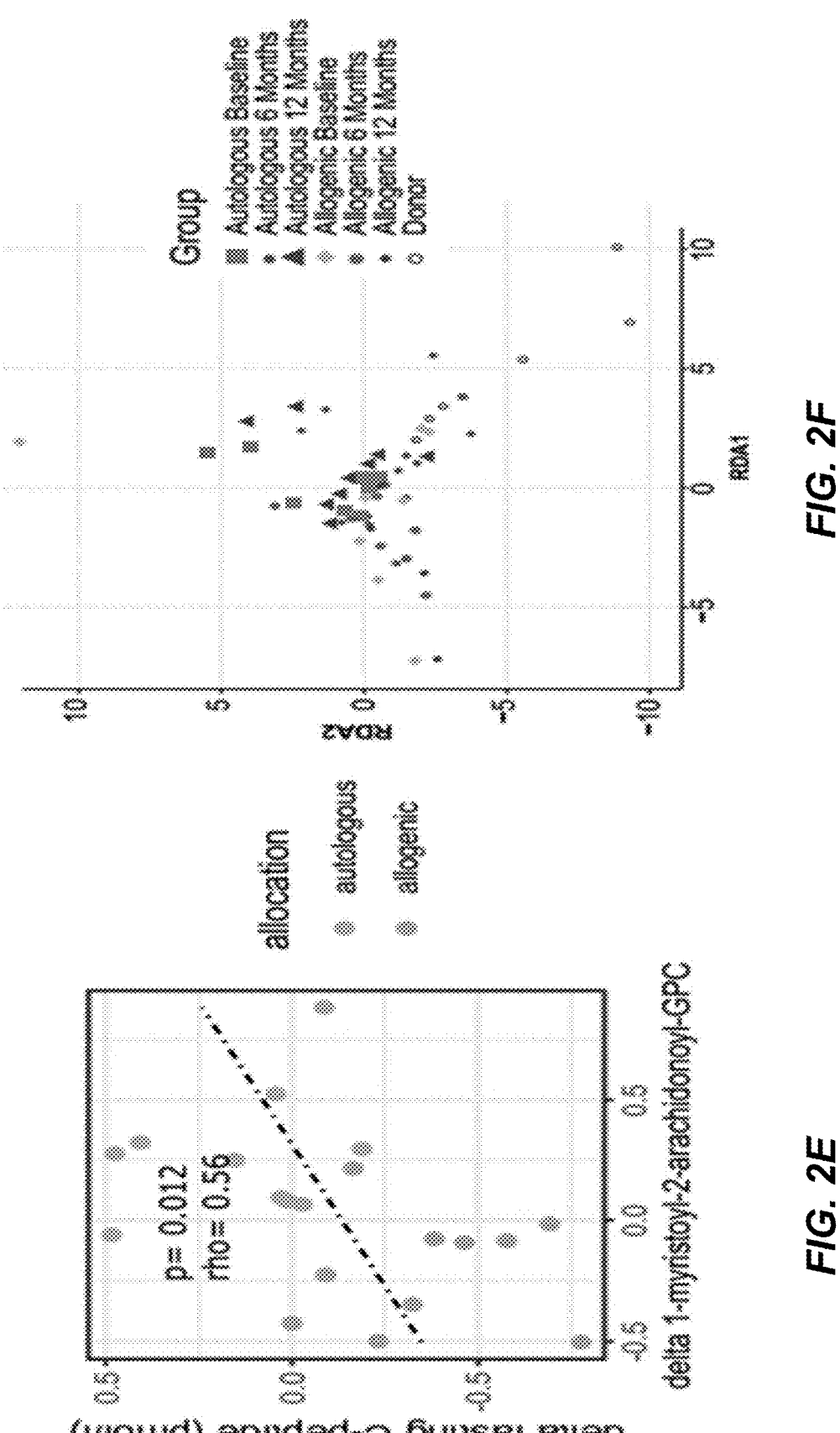
Figures 2G, 2H, 2I, 2J, 2K, 2L:
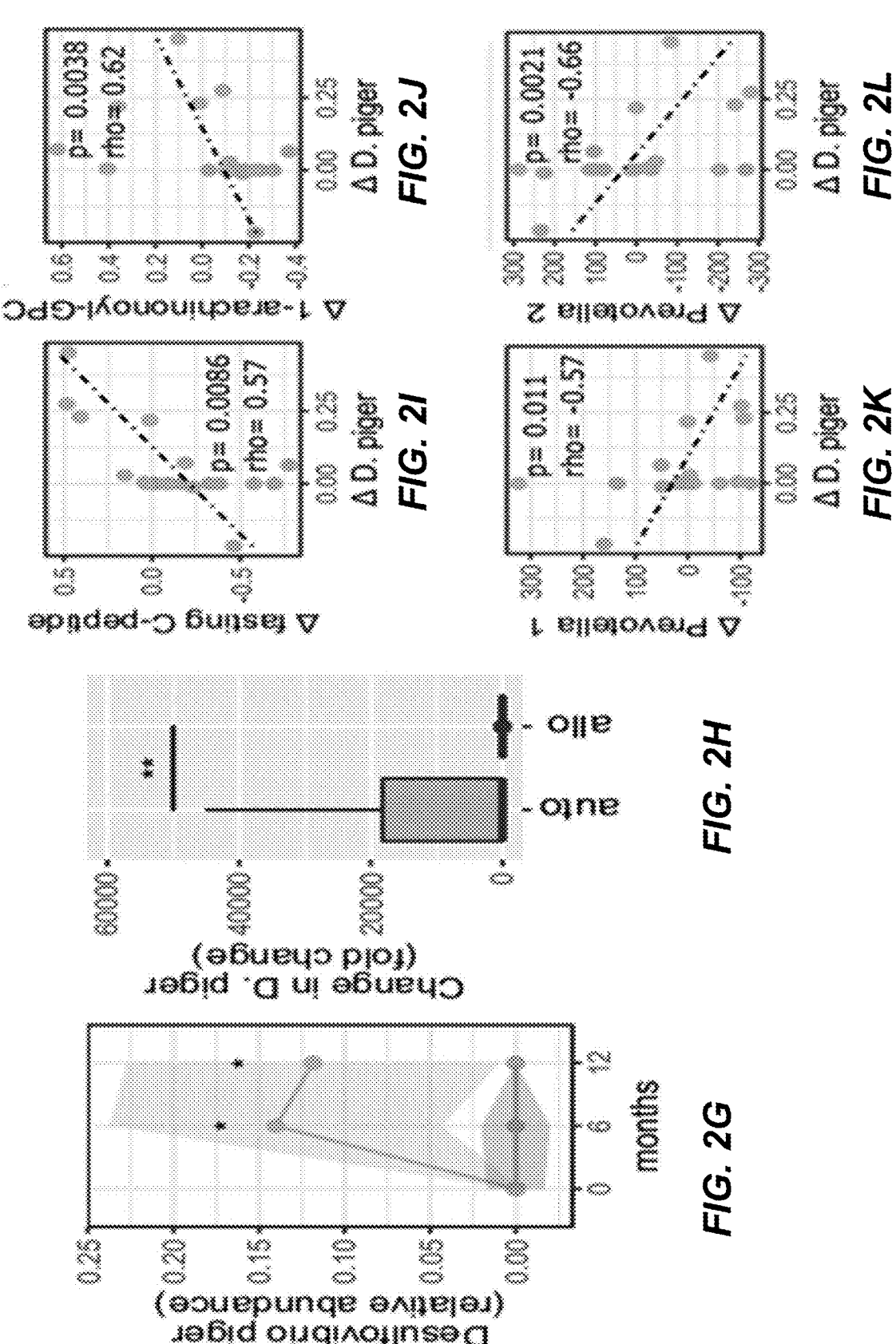

FIG. 2I: Exposure of monocytes (isolated from murine bone marrow; Christ A., Cell 2018) to 6-BT or tryptophan, shows that the anti-inflammatory effects are specific for the 6-bromotryptophan molecule and not for tryptophan.

Figure 22:
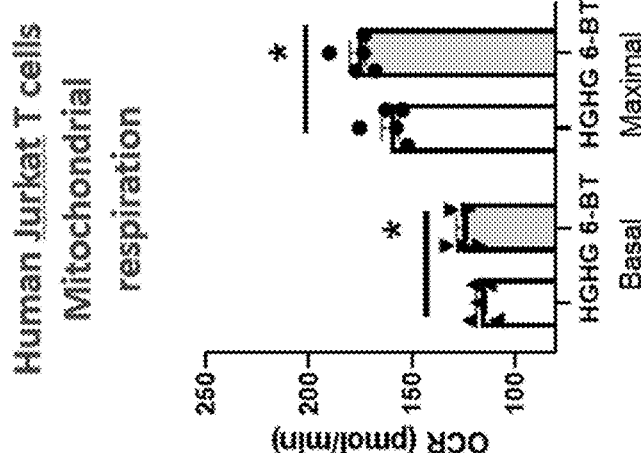
Figure 22:
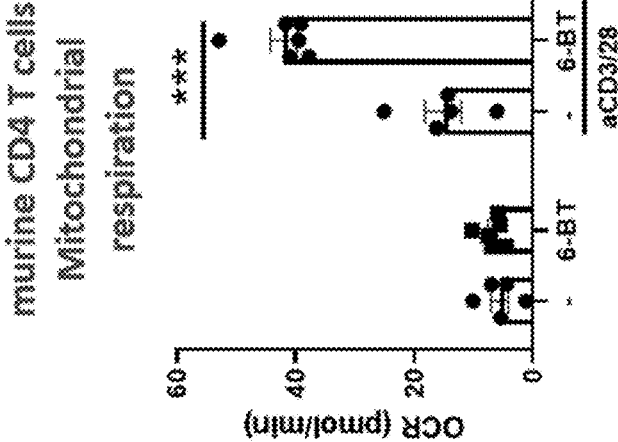

FIG. 22: It was found that 6-BT (100 µM) promoted the mitochondrial metabolism in murine and human (Jurkat) CD4 T cells. OCR=oxygen consumption rate, used as a proxy of cellular utilization of mitochondrial oxidative phosphorylation. OCR was measured using a Seahorse XF Analyzer Uchimura T., Immunity 2019; Chou, Nature 2021.

Figure 23:
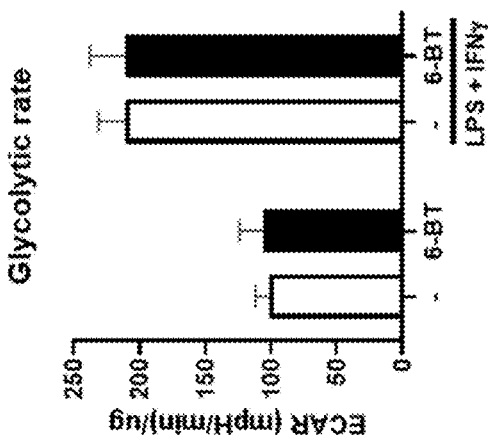
Figure 23:
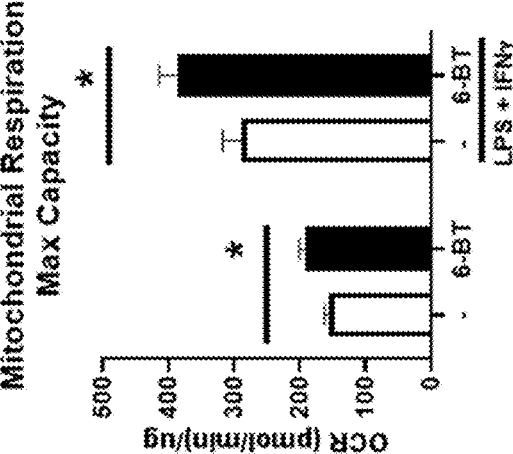
Figure 23:
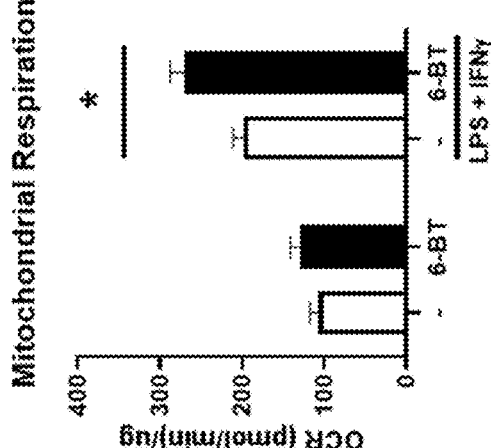

FIG. 23: 6-BT exposure could enhance the mitochondrial metabolism of pro-inflammatory M1 macrophages (differentiated in presence of LPS and IFNgamma; Cheng N., JCI Insight 2018), without affecting the glycolytic flux. Intracellular metabolism measured using a Seahorse XF Analyzer Uchimura T., Immunity 2019; Chou, Nature 2021.

Figure 24:
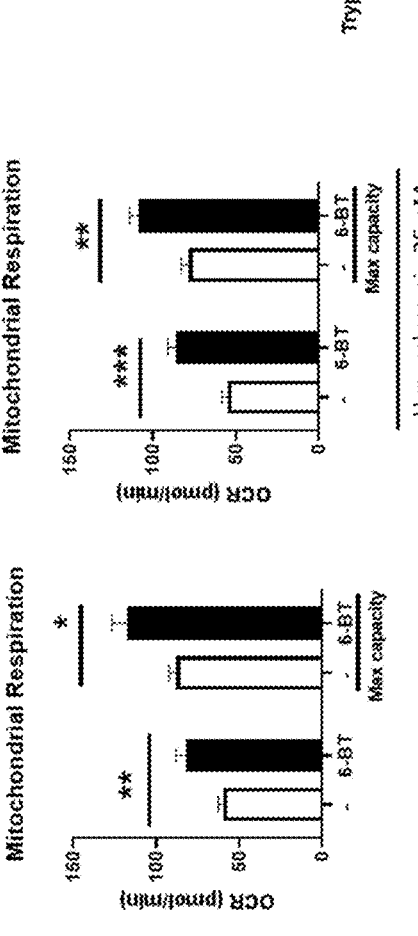
Figure 24:
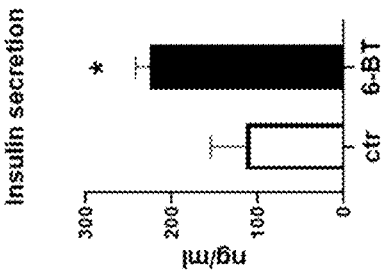

FIG. 24: It was investigated whether 6-BT may influence the mitochondrial metabolism of beta cells, which rely on ATP and mitochondrial metabolite production for insulin exocytosis. 6-BT increased mitochondria metabolism both at steady-state and under hyperglycemia (25 mM glucose) in beta cells (INS1E beta cells). In addition, the effect of tryptophan on intracellular metabolism was tested and it was found that, as for the inflammatory markers, it exerted a different effect than 6-BT. Intracellular metabolism measured using a Seahorse XF Analyzer Uchimura T., Immunity 2019; Chou, Nature 2021.

Figure 25:
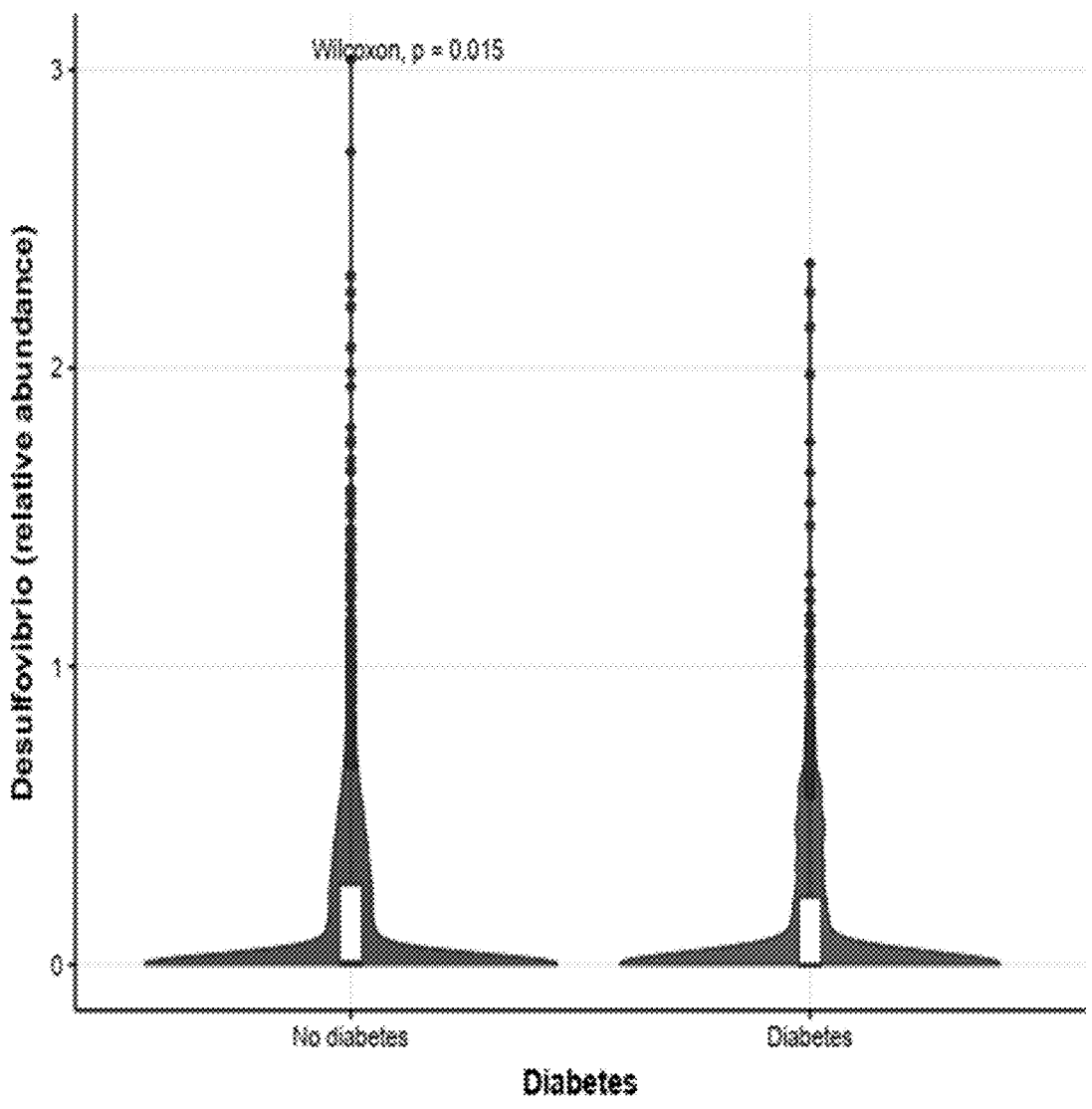

FIG. 25: Relative fecal *Desulfovibrio* abundance in Diabetes vs non-Diabetes subjects.

Figure 26:
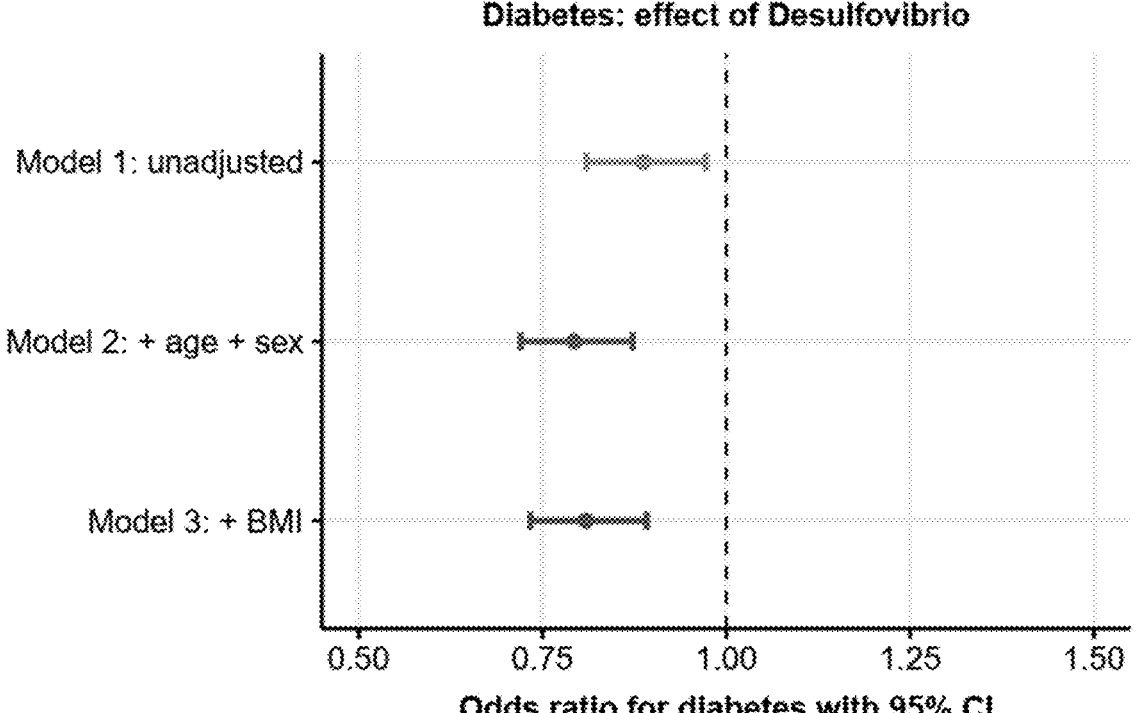

FIG. 26: Diabetes: Effect of *Desulfovibrio* genus. Odds ratio for Diabetes.

Figure 27:
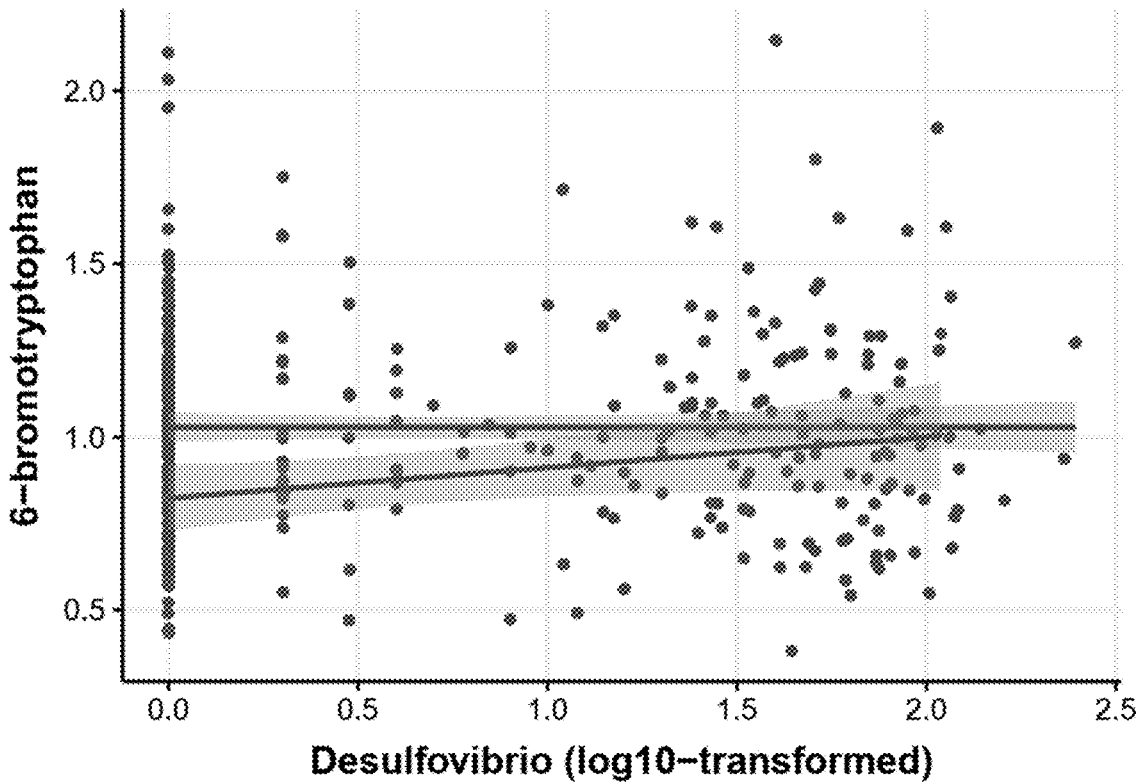

FIG. 27: Relationship between plasma 6BT levels and fecal *Desulfovibrio* genus relative abundance in (1) non Diabetes subjects (upper line) and (2) Diabetes patients (lower line).

DETAILED DESCRIPTION

Example 1

Patients with conditions as indicated below are treated with:

1. Oral administration, daily for 2 years, of an empty enteric coated capsule.

2. Oral administration, daily for 2 years, of an enteric coated capsule comprising ~1*10^8 cells of an *Desulfovibrio* species (*Desulfovibrio piger*, *Desulfovibrio desulfuricans*, or *Desulfovibrio fairfieldensis*)

3. Oral administration, daily for 2 years, of an enteric coated capsule comprising 50 mg chloro-, fluoro-, or bromo-substituted tryptophan (6-bromotryptophan (6-BT) or 6-fluorotryptophan (6-FT)).

4. Oral administration, daily for 2 years, of an enteric coated capsule comprising 50 mg mono- or di-fatty acid substituted glycerol phosphocholine (GPC) (1-myristoyl-2-arachidonoyl-glycero-phosphocholine (MA-GPC) or 1-arachidonoyl-glycero-phosphocholine (A-GPC)).

TABLE 1

| Condition | Effect treatment 1 (patient 1) | Effect treatment 2 (patient 2) | Effect treatment 3 (patient 3) | Effect treatment 4 (patient 4) |
|---|---|---|---|---|
| Type 1 Diabetes | No effect | (*Desulfovibrio piger*) residual beta cell reserve is stabilized over time, beneficial changes in T and B cell function | (6-BT) residual beta cell reserve is stabilized over time, beneficial changes in T and B cell function | (MA-GPC) residual beta cell reserve is stabilized over time, beneficial changes in T and B cell function |
| Type 2 Diabetes | No effect | (*Desulfovibrio piger*) Reduced polyuria, reduced polydipsia, less need of exogenous hormone supplementation, beneficial changes in T and B cell function, less perceived fatigability | (6-BT) Reduced polyuria, reduced polydipsia, less need of exogenous hormone supplementation, beneficial changes in T and B cell function, less perceived fatigability | (A-GPC) Reduced polyuria, reduced polydipsia, less need of exogenous hormone supplementation, beneficial changes in T and B cell function, less perceived fatigability |
| Hashimoto's disease | No effect | (*Desulfovibrio piger*) Slowed down progression of disease, less need of exogenous hormone supplementation, beneficial changes in T and B cell function, less perceived fatigability | (6-BT) Slowed down progression of disease, less need of exogenous hormone supplementation, beneficial changes in T and B cell function, less perceived fatigability | (MA-GPC) Slowed down progression of disease, less need of exogenous hormone supplementation, beneficial changes in T and B cell function, less perceived fatigability |
| Graves' disease | No effect | (*Desulfovibrio desulfuricans*) Slowed down progression of the disease, reduced enlargement of thyroid gland, less risk of remission and radioactive iodine treatment need, beneficial changes in T and B cell function | (6-FT) Slowed down progression of the disease, reduced enlargement of thyroid gland, less risk of remission and radioactive iodine treatment need, beneficial changes in T and B cell function | (A-GPC) Slowed down progression of the disease, reduced enlargement of thyroid gland, less risk of remission and radioactive iodine treatment need, beneficial changes in T and B cell function |
| Addison's disease | No effect | (*Desulfovibrio piger*) Slowed down progression of disease, less need of exogenous hormone supplementation, beneficial | (6-BT) Slowed down progression of disease, less need of exogenous hormone supplementation, beneficial changes in | (MA-GPC) Slowed down progression of disease, less need of exogenous hormone supplementation, beneficial changes in |

TABLE 1-continued

| Condition | Effect treatment 1 (patient 1) | Effect treatment 2 (patient 2) | Effect treatment 3 (patient 3) | Effect treatment 4 (patient 4) |
|---|---|---|---|---|
| | | changes in T and B cell function, reduced hyper-pigmentation | T and B cell function, reduced hyper-pigmentation | T and B cell function, reduced hyper-pigmentation |
| Psoriasis | No effect | (Desulfovibrio fairfieldensis) Slowed down progression of disease, somewhat reduced red inflamed areas, beneficial changes in T and B cell function | (6-FT) Slowed down progression of disease, somewhat reduced red inflamed areas, beneficial changes in T and B cell function | (A-GPC) Slowed down progression of disease, somewhat reduced red inflamed areas, beneficial changes in T and B cell function |
| Vitiligo | No effect | (Desulfovibrio piger) Slowed down progression of disease, some white patches on the skin disappear, beneficial changes in T and B cell function | (6-FT) Slowed down progression of disease, some white patches on the skin disappear, beneficial changes in T and B cell function | (A-GPC) Slowed down progression of disease, some white patches on the skin disappear, beneficial changes in T and B cell function |
| Rheumatoid arthritis | No effect | (Desulfovibrio piger) Reduced progression of disease symptoms, and less pain around joints, less need of exogenous medication including DMARDS, beneficial changes in T and B cell function | (6-BT) Reduced progression of disease symptoms, and less pain around joints, less need of exogenous medication including DMARDS, beneficial changes in T and B cell function | (MA-GPC) Reduced progression of disease symptoms, and less pain around joints, less need of exogenous medication including DMARDS, beneficial changes in T and B cell function |
| Bechterew's disease | No effect | (Desulfovibrio fairfieldensis) Slowed down progression of disease, less perceived lower back pain, less need of exogenous medication including DMARDS, beneficial changes in T and B cell function | (6-BT) Slowed down progression of disease, less perceived lower back pain, less need of exogenous medication including DMARDS, beneficial changes in T and B cell function | (MA-GPC) Slowed down progression of disease, less perceived lower back pain, less need of exogenous medication including DMARDS, beneficial changes in T and B cell function |
| Celiac disease | Ingestion of small amount of gluten leads to upset stomach, stomach | (Desulfovibrio piger) Ingestion of small amount of gluten leads to less upset | (6-BT) Ingestion of small amount of gluten leads to less upset stomach | (MA-GPC) Ingestion of small amount of gluten leads to less upset stomach |

TABLE 1-continued

| Condition | Effect treatment 1 (patient 1) | Effect treatment 2 (patient 2) | Effect treatment 3 (patient 3) | Effect treatment 4 (patient 4) |
|---|---|---|---|---|
| | pain, inflammation, diarrhea, gas | stomach but no pain, less diarrhea, less gas, less osteoporosis, beneficial changes in T and B cell function | but no pain, less diarrhea, less gas, less osteoporosis, beneficial changes in T and B cell function | but no pain, less diarrhea, less gas, less osteoporosis, beneficial changes in T and B cell function |
| Asthma | No effect | (Desulfovibrio piger) Slowed down disease progression, less episodes of coughing, shortness of breath (improved reversibility of FEVI upon broncho-dilators), less need of exogenous medication including synergy with broncho-dilators, beneficial changes in T and B cell function | (6-BT) Slowed down disease progression, less episodes of coughing, shortness of breath (improved reversibility of FEVI upon broncho-dilators), less need of exogenous medication including synergy with broncho-dilators, beneficial changes in T and B cell function | (MA-GPC) Slowed down disease progression, less episodes of coughing, shortness of breath (improved reversibility of FEVI upon broncho-dilators), less need of exogenous medication including synergy with broncho-dilators, beneficial changes in T and B cell function |
| Emphysema (COPD) | No effect | (Desulfovibrio piger) Slowed down disease progression, less episodes of coughing, shortness of breath (improved reversibility of FEVI upon broncho-dilators), less need of exogenous medication including synergy with broncho-dilators, beneficial changes in T and B cell function | (6-BT) Slowed down disease progression, less episodes of coughing, shortness of breath (improved reversibility of FEVI upon broncho-dilators), less need of exogenous medication including synergy with broncho-dilators, beneficial changes in T and B cell function | (MA-GPC) Slowed down disease progression, less episodes of coughing, shortness of breath (improved reversibility of FEVI upon broncho-dilators), less need of exogenous medication including synergy with broncho-dilators, beneficial changes in T and B cell function |
| Vasculitis | No effect | (Desulfovibrio piger) Slowed down progression of the disease, perceived severity of symptoms is reduced, | (6-FT) Slowed down progression of the disease, perceived severity of symptoms is reduced, i.e., less | (A-GPC) Slowed down progression of the disease, perceived severity of symptoms is reduced, i.e., less |

TABLE 1-continued

| Condition | Effect treatment 1 (patient 1) | Effect treatment 2 (patient 2) | Effect treatment 3 (patient 3) | Effect treatment 4 (patient 4) |
|---|---|---|---|---|
| | | i.e., less fever, fatigue, weakness, weight loss, general aches and pains, numbness, beneficial changes in T and B cell function | fever, fatigue, weakness, weight loss, general aches and pains, numbness, beneficial changes in T and B cell function | fever, fatigue, weakness, weight loss, general aches and pains, numbness, beneficial changes in T and B cell function |
| Systemic lupus erythematosus (SLE) | No effect | (Desulfovibrio desulfuricans) Slowed down progression of the disease, less painful and swollen joints, fever, chest pain, hair loss, mouth ulcers, swollen lymph nodes, and perceived fatigue, beneficial changes in T and B cell function | (6-BT) Slowed down progression of the disease, less painful and swollen joints, fever, chest pain, hair loss, mouth ulcers, swollen lymph nodes, and perceived fatigue, beneficial changes in T and B cell function | (MA-GPC) Slowed down progression of the disease, less painful and swollen joints, fever, chest pain, hair loss, mouth ulcers, swollen lymph nodes, and perceived fatigue, beneficial changes in T and B cell function |
| Guillain-Barre syndrome (GBS) | No effect | (Desulfovibrio piger) Slowed down progression of the disease, less perceived muscle weakness, beneficial changes in T and B cell function | (6-BT) Slowed down progression of the disease, less perceived muscle weakness, beneficial changes in T and B cell function | (MA-GPC) Slowed down progression of the disease, less perceived muscle weakness, beneficial changes in T and B cell function |
| Chronic inflammatory demyelinating polyneuropathy (CDIP) | No effect | (Desulfovibrio piger) Slowed down progression of the disease, less perceived muscle weakness, beneficial changes in T and B cell function | (6-FT) Slowed down progression of the disease, less perceived muscle weakness, beneficial changes in T and B cell function | (A-GPC) Slowed down progression of the disease, less perceived muscle weakness, beneficial changes in T and B cell function |
| Multiple sclerosis (MS) | No effect | (Desulfovibrio piger) Slowed down progression of the disease, less perceived muscle weakness, less trouble with sensation and coordination, beneficial | (6-BT) Slowed down progression of the disease, less perceived muscle weakness, less trouble with sensation and coordination, beneficial changes in | (MA-GPC) Slowed down progression of the disease, less perceived muscle weakness, less trouble with sensation and coordination, beneficial changes in |

TABLE 1-continued

| Condition | Effect treatment 1 (patient 1) | Effect treatment 2 (patient 2) | Effect treatment 3 (patient 3) | Effect treatment 4 (patient 4) |
|---|---|---|---|---|
| Athero-sclerosis | No effect | changes in T and B cell function (Desulfovibrio piger) Reduced risk of coronary artery disease, reduced levels of inflammation markers (TNFalfa) | T and B cell function (6-BT) Reduced risk of coronary artery disease, reduced levels of inflammation markers (TNFalfa | T and B cell function (A-GPC) Reduced risk of coronary artery disease, reduced levels of inflammation markers (TNFalfa |

It is expected that results similar to the putative effects as shown in the Table 1 above can be obtained with larger patient cohorts.

Example 2

Recent-onset (<6 weeks) T1D patients were randomized in two groups to receive three autologous or allogenic (healthy donor) fecal microbiota transplantations (FMTs) over a period of 4 months.

It was found that several (microbiota derived) plasma metabolites and (small) intestinal bacterial strains are linked with improved residual beta cell function in Type 1 Diabetes.

Materials and Methods

A double-blind randomized controlled trial was performed in new onset T1D subjects using computerized randomization. The effects were studied of allogenic (healthy donor) compared to autologous (own) gut microbiota infusion on residual beta cell function and autoimmune T cell response in relation to changes in (small) intestinal microbiota during 1 year after treatment.

Patient Recruitment

New onset T1D patients were recruited from outpatient clinics in the Amsterdam region. Inclusion criteria for patients were males/females, age 18-35, normal BMI (18.5-25 kg/m$^2$), and a diagnosis of T1D within a maximum period of six weeks before inclusion, with residual beta cell function (as indicated by plasma C-peptide >0.2 mmol/l and/or >1.2 ng/mL after MMT). Exclusion criteria were a diagnosis or symptoms of another autoimmune disease (eg hypo- or hyperthyroidism, celiac disease, rheumatoid arthritis or inflammatory bowel), (expected) prolonged compromised immunity (due to recent cytotoxic chemotherapy or HIV infection with a CD4 count <240) as well as antibiotic use in the last 3 months, use of proton pump inhibitors and any other kind of systemic medication barring insulin.

Donor Recruitment

Lean (BMI <25 kg/m$^2$), omnivorous, healthy Caucasian male and females were recruited to serve as fecal donors. They completed questionnaires regarding dietary and bowel habits, travel history, comorbidity including family history of diabetes mellitus and medication use. Donors were screened for the presence of infectious diseases as described previously (van Nood et al., 2013). Blood was screened for human immunodeficiency virus; human T-lymphotropic virus; Hepatitis A, B, and C; cytomegalovirus (CMV); Epstein-Barr virus (EBV); *strongyloides*; amoebiasis, and lues. Presence of infection resulted in exclusion, although previous and non-active infections with EBV and CMV were allowed. Donors were also excluded if screening of their feces revealed the presence of pathogenic parasites (e.g., *blastocystis hominis, dientamoeba fragilis, giardia lamblia*), multiresistant bacteria (*Shigella, Campylobacter, Yersinia*, MRSA, ESBL, *Salmonella*, enteropathogenic *E. Coli* and *Clostridium difficile*) or viruses (noro-, rota-, astro-, adeno (40/41/52)-, entero-, parecho- and sapovirus) as previously recommended.

Study Visits

Participants were asked to fill out an online nutritional diary for the duration of one week before every study visit to monitor caloric intake including the amount of dietary carbohydrates, fats, proteins and fibers. During the study visit, blood pressure, length, weight and daily insulin use were documented. Fasting blood samples were taken at each visit and upon centrifugation stored at −80° C. for later analyses. Whole blood sodium heparin tubes were kept on room temperature and processed within 24 hours for immunological analyses.

Three fecal transplantations using freshly produced feces were performed at 0, 2 and 4 months. Mixed-meal tests (for residual beta cell function), intestinal microbiota analyses were performed at 0, 2, 6, 9, and 12 months. Plasma metabolites were measured at 0, 6, and 12 months. Biometric measurements and fasting plasma to monitor safety parameters were performed on all time points.

Description Per Study Visit

All visits took place after an overnight fast with subjects taking no long acting insulin the night before. At each visit, blood sampling, fecal and urine sampling and biometric measurements took place. At baseline/0 months, positioning of a nasoduodenal tube was performed. After placement of the tube, when the patient was properly awake, a standardized 2-hour mixed meal test (Nestlé sustacal BOOST®) was performed as previously described (Moran et al., 2013) to study residual beta cell function. At 2, 9, and 12 months, patients again underwent a mixed-meal test for residual beta cell C-peptide secretion. Then, a duodenal tube was placed by means of CORTRAK enteral access and the fecal transplant procedures were repeated.

At 6 months, the mixed-meal test was performed.

Fecal Transplant Procedure

Subjects were allocated randomly to receive three autologous or allogenic fecal transplantations. All patients and investigators were masked to treatment assignment. After admission, a duodenal tube was placed by gastroscopy or CORTRAK enteral access system. Each patient then underwent complete colon lavage with 2-4 L of KLEAN-PREP® (macrogol) by duodenal tube until the researcher judged that the bowel was properly lavaged (i.e., no solid excrement, but clear fluid) for approximately 3 hours. Then, between 200 and 300 grams of donor feces was processed by dilution in 500 ml of 0.9% saline solution and filtered through unfolded cotton gauzes. The filtrate was used for transplantation two hours after the last administration of KLEAN-PREP® by duodenal tube in around 30 minutes using 50 cc syringes. After a short observation period the patient was sent home.

Mixed Meal Test

Starting the evening before each mixed meal test, T1D patients paused their long-acting insulin injections. After an overnight fast and without taking their short-acting morning insulin dose, a mixed meal test was performed with Boost High Protein (Nestlé Nutrition, Vervey, Switzerland) at 6 ml/kg body weight with a maximum of 360 ml per person. Subsequent blood sampling for stimulated C-peptide were taken at −10, 0, 15, 30, 45, 60, 90 and 120 minutes. AUC (area under the curve) values were derived according to the trapezoidal rule.

Plasma Metabolites

Fasting plasma metabolite measurements were done by Metabolon (Durham, NC), using ultra high performance liquid chromatography coupled to tandem mass spectrometry (UPLC-MS/MS). Raw data was normalized to account for inter-day differences. Then, the levels of each metabolite were rescaled to set the median equal to 1 across all samples. Missing values, generally due to the sample measurement falling below the limit of detection, were then imputed with the minimum observed value for the respective metabolite.

Biochemistry

Glucose and C-reactive protein (CRP, Roche, Switzerland) were determined in fasted plasma samples. C-peptide was measured by radioimmunoassay (Millipore). Total cholesterol, high density lipoprotein cholesterol (HDLc), and triglycerides (TG) were determined in EDTA-containing plasma using commercially available enzymatic assays (Randox, Antrim, UK and DiaSys, Germany). All analyses were performed using a Selectra autoanalyzer (Sopachem, The Netherlands). Low density lipoprotein cholesterol (LDLc) was calculated using the Friedewald formula. Calprotectin was determined in feces using a commercial ELISA (Bühlmann, Switzerland).

Fecal Sample Shotgun Sequencing and Metagenomic Pipeline

Fecal microbiota were analyzed using shotgun sequencing on donor fecal samples and fecal samples taken at 0, 6 and 12 months after initiation of study. DNA extraction from fecal samples for shotgun metagenomics was performed. Subsequently, shotgun metagenomic sequencing was performed (Clinical Microbiomics, Copenhagen, Denmark.). Before sequencing, the quality of the DNA samples was evaluated using agarose gel electrophoresis, NanoDrop 2000 spectrophotometry and Qubit 2.0 fluorometer quantitation. The genomic DNA was randomly sheared into fragments of around 350 bp. The fragmented DNA was used for library construction using NEBNext Ultra Library Prep Kit for Illumina (New England Biolabs). The prepared DNA libraries were evaluated using Qubit 2.0 fluorometer quantitation and Agilent 2100 Bioanalyzer for the fragment size distribution. Quantitative real-time PCR (qPCR) was used to determine the concentration of the final library before sequencing. The library was sequenced on a Illumina HiSeq platform to produce 2×150 bp paired-end reads. Raw reads were quality filtered using Trimmomatic (v0.38), removing adapters, trimming the first 5 bp, and then quality trimming reads using a sliding window of 4 bp and a minimum Q-score of 15. Reads that were shorter than 70 bp after trimming were discarded. Surviving paired reads were mapped against the human genome (GRCh37_hg19) with bowtie2 (v2.3.4.3) in order to remove human reads. Finally, the remaining quality filtered, non-human reads were subsampled to 20 million reads per sample and processed using Metaphlan2 (v2.7.7) to infer metagenomic microbial species composition and Humann2 (v0.11.2) to extract gene counts and functional pathways. In brief, reads were mapped using bowtie2 against microbial pangenomes; unmapped reads were translated and mapped against the full Uniref90 protein database using diamond (v0.8.38). Pathway collection was performed using the MetaCyc database.

Small Intestinal Microbiota Analyses

Biopsies were added to a bead-beating tube with 300 µl Stool Transport and Recovery (STAR) buffer, 0.25 g of sterilized zirconia beads (0.1 mm). Six ul of Proteinase K (20 mg/ml; QIAGEN, Venlo, The Netherlands) was added and incubated for 1 hour at 55° C. The biopsies were then homogenized by bead-beating three times (60 s×5.5 ms) followed by incubation for 15 min at 95° C. at 1000 rpm. Samples were then centrifuged for 5 min at 4° C. and 14,000 g and supernatants transferred to sterile tubes. Pellets were re-processed using 200 µl STAR buffer and both supernatants were pooled. DNA purification was performed with a customized kit (AS1220; Promega) using 250 µl of the final supernatant pool. DNA was eluted in 50 µl of DNAse-RNAse-free water and its concentration measured using a DS-11 FX+ Spectrophotometer/Fluorometer (DeNovix Inc., Wilmington, USA) with the Qubit™ dsDNA BR Assay kit (Thermo Scientific, Landsmeer, The Netherlands). The V5-V6 region of 16S ribosomal RNA (rRNA) gene was amplified in duplicate PCR reactions for each sample in a total reaction volume of 50 µl. A first step PCR using the 27F and the 1369R primer were used for primary enrichment. One ul of 10 µM primer, 1 µl dNTPs mixture, 0.5 µl Phusion Green Hot Start II High-Fidelity DNA Polymerase (2 U/µl; Thermo Scientific, Landsmeer, The Netherlands), 10 µl 5× Phusion Green HF Buffer, and 36.5 µl DNAse- RNAse-free water. The amplification program included 30 s of initial denaturation step at 98° C., followed by 5 cycles of denaturation at 98° C. for 30 s, annealing at 52° C. for 40 s, elongation at 72° C. for 90 s, and a final extension step at 72° C. for 7 min. On the PCR product a nested PCR was performed using the master mix containing 1 µl of a unique barcoded primer, 784F-n and 1064R-n (10 µM each per reaction), 1 µl dNTPs mixture, 0.5 µl Phusion Green Hot Start II High-Fidelity DNA Polymerase (2 U/µl; Thermo Scientific, Landsmeer, The Netherlands), 10 µl 5× Phusion Green HF Buffer, and 36.5 µl DNAse- RNAse-free water. The amplification program included 30 s of initial denaturation step at 98° C., followed by 5 cycles of denaturation at 98° C. for 10 s, annealing at 42° C. for 10 s, elongation at 72° C. for 10 s, and a final extension step at 72° C. for 7 min. The PCR product was visualized in 1% agarose gel (~280 bp) and purified with CleanPCR kit (CleanNA, Alphen aan den Rijn, The Netherlands). The concentration of the purified PCR product was measured with Qubit dsDNA BR Assay Kit (Invitrogen, California, USA) and 200 ng of microbial DNA from each sample were pooled for the creation of the final amplicon library, which was sequenced (150 bp, paired-end) on the Illumina HiSeq. 2500 platform (GATC Biotech, Constance, Germany).

Raw reads were demultiplexed using the Je software suite (v2.0.) allowing no mismatches in the barcodes. After removing the barcodes, linker and primers, reads were mapped against the human genome using bowtie2 in order to remove human reads. Surviving microbial forward and reverse reads were pipelined separately using DADA2(Callahan et al., 2016) (v1.12.1). Amplicon Sequence Variants (AVSs) inferred from the reverse reads were reverse-complemented and matched against ASVs inferred from the forwards reads. Only non-chimeric forward reads ASVs that matched reverse-complemented reverse reads ASVs were kept. ASV sample counts were inferred from the forward reads. ASV taxonomy was assigned using DADA2 and the SILVA (v132) database. The resulting ASV table and taxonomy assignments were integrated using the phyloseq R package (v1.28.0) and rarefied to 60000 counts per sample.

Power Calculation and Statistics

A sample size of 17 patients in each group (34 patients in total) was needed to provide 80% power to detect a 50% difference in the C-peptide AUC (360 mmol/l/min vs 180 mmol/l/min with a standard deviation of 170) between treatment groups at 12 months, with a two-sided test at $\alpha=0\cdot05$ and 10% dropout. All analyses were based on the pre-specified intention-to-treat cohorts with known measurements (complete case analysis); missing values were assumed to be missing at random. Primary endpoint of the trial was the preservation of residual (MMT stimulated) beta cell function at 6 and 12 months compared to baseline (0 months). Other secondary endpoints were changes during these 12 months in whole blood leukocyte subsets for immunologic markers of autoimmunity, parameters of glycemic control as well as fasting plasma metabolites. Finally, changes between baseline and 6 months after start of the FMT in small intestinal epithelial genes were determined. Analyses were done by intention to treat.

For baseline differences between groups unpaired Student t-test or the Mann-Whitney U test were used dependent on the distribution of the data. Accordingly, data are expressed as mean±the standard deviation or the median with inter-quartile range. Post-prandial results (e.g., c-peptide) are described as area under the curves (AUC) for the 2 hour post-prandial follow-up, calculated by using the trapezoidal method. For correlation analyses, Spearman's Rank test was used (as all parameters were non-parametric). For comparison of the primary end point a linear mixed model (LMM) was used (lme4 package in R), where "allocation" and "timepoint" were fixed effects and "patient entry number" was a random effect. The p value for the interaction between "allocation" and "timepoint" was reported. Additionally, parameters were compared between groups at various time points using Mann-Whitney U test. A p-value <0.05 was considered statistically significant. The study was conducted at the Academic Medical Center (Amsterdam), in accordance with the Declaration of Helsinki (updated version 2013). All participants provided written informed consent and all study procedures were approved by the IRB (ethics committee) of the Academic Medical Center. The study was prospectively registered at the Dutch Trial registry (NTR3697).

Machine Learning and Follow-Up Statistical Analyses

Extreme Gradient Boosting (XGBoost) machine learning classification algorithm was applied, in combination with a stability selection procedure to identify which parameters (either as values at baseline, or as relative changes) best predicted treatment groups and responders versus non-responders. This technique was used on duodenal microbial composition (16S rRNA sequencing on biopsies), on fecal microbiota composition and metabolic pathway abundance, and on plasma metabolite levels. To predict treatment groups, the relative change (delta) of each parameter between 0 and 12 months was used. For duodenal microbes delta 0 vs 6 months was used. For prediction of responders vs non-responders, baseline values, delta 0 vs 6 months and delta 0 vs 12 months were used. Each analysis produced a ranked list of the top 30 of most discriminative features. The top parameters were selected from each analysis that accurately (i.e., ROC AUC of 0.8 or higher) or moderately (ROC AUC >0.7) predicted group allocation for closer study, using an arbitrary but reasonable cut off. This cut off was generally a relative importance of around 30% or higher. Then, the change in time was visualized of the selected parameters (Wilcoxon's signed rank tests) and between-group differences were studies (Mann-Whitney U tests) at each time point using and finally, using Spearman's rank test, these parameters were correlated with the primary end point and with other key parameters that were identified in this way.

Results

Patients were randomly assigned to donor FMT (n=11 subjects) or autologous FMT (n=10 subjects). One participant retracted consent after the first study visit. Due to lack of funding, the trial was stopped after 20 subjects were enrolled and completed the study. Seven healthy lean donors (of whom 3 were used twice) donated for the allogenic gut microbiota transfer to 10 new onset DM1 patients, and the same donor was used for the three consecutive FMT's in each DM1 patient. There were no differences at baseline between both groups and also throughout the follow-up period, there were no serious adverse events or adverse changes in plasma biochemistry in both treatment groups.

Autologous FMT Preserves (Stimulated)C-Peptide Levels Better than Allogenic FMT

Mean fasting plasma C-peptide at baseline was similar between groups (327 pmol/1+/−89 in the allogenic group vs 319+/−118 in the autologous group; p=0.86, Student's T-test), but deteriorated in the allogenic FMT group compared to the autologous FMT group at 12 months (202+/−85 vs 348 pmol/1+/−115, Student's T-test p-value=0.0049; LMM p=0.00019). A similar effect was seen in stimulated C-peptide response AUC, which was similar between groups at baseline (361+/−154 mmol/1-min in the allogenic group vs 355+/−97 in the autologous group; p=0.92, Student's T-test), but residual betacell function was significantly more preserved at 12 months after autologous FMT (392+/−124 vs 248+/−153 mmol/1-min, Student's T-test p-value=p=0.033, LMM p-value=0.000067). As expected, exogenous insulin treatment lowered HbA1c levels in both groups at 12 months. Despite similar amounts of daily exogenous insulin needs between the allogenic (0.45+/−SD IU/kg/day) and the autologous FMT group (0.47 IU/kg/day), and although not significant improved glycemic control was suggested in the autologous FMT compared to the allogenic FMT group (HbA1c 46 vs 53.5 mmol/mol, MWU p=0.19, LMM p-value=0.12). Glucometabolic parameters at 0, 6 and 12 months were determined. Finally, BMI, fecal calprotectin, microalbuminuria, lipid profiles, and dietary intake (separate assessment of total calories, fat, saturated fat, protein, carbohydrates, and fiber) were not different at baseline nor during the course of the study.

Treatment success of autologous FMT can be predicted by changes in plasma metabolites as well as microbiota composition.

Small Intestinal Microbiota Differences Between FMT Treatment Groups

Figure 1:
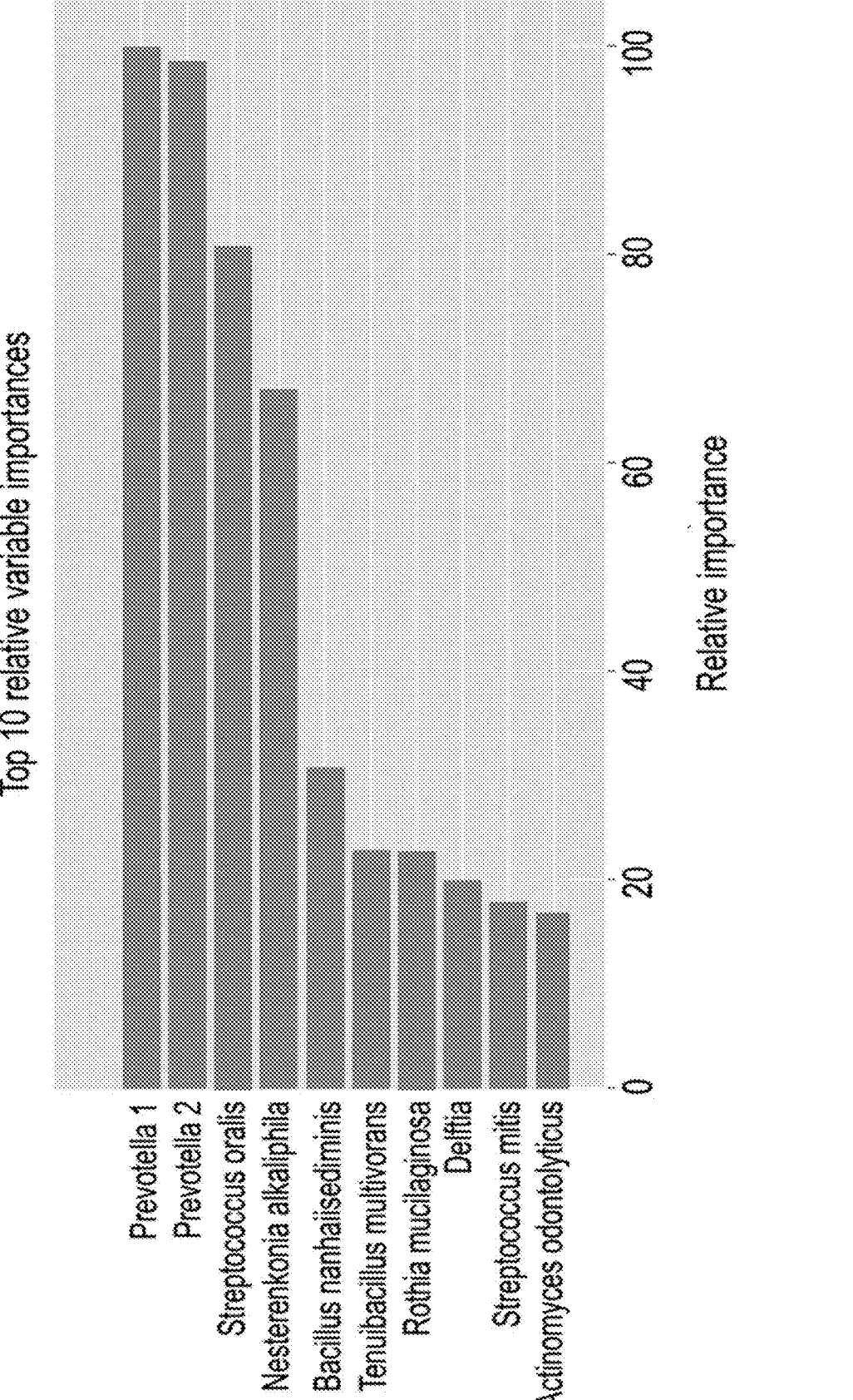
FIG. 1: Top 10 small intestinal microbiota with relative importance that best predicted treatment group allocation (XGBoost predictive modeling algorithm). Percentages are scaled toward the largest, which is set at 100%. The top 4 microbiota stand out with higher relative importance.

Alpha diversity of the small intestinal microbiota was not significantly different between treatment groups at baseline, but at 6 months there was a significant difference between autologous and allogenic FMT group (p=0.054), which was in line with a significant increase in diversity in the allogenic FMT group (p=0.009). When plotted along ordination axes in a redundancy analysis (RDA-plot), small intestinal microbiota compositions clustered differently at baseline between groups and also changed differentially between treatment groups. FMT treatment group allocation could be predicted reliably by change in specific small intestinal bacterial strains (AUC ROC 0.89±0.18) including two species of *Prevotella* and *Streptococcus oralis* (FIG. 1). However, changes on the phylum, family, genus, and species level showed no major shifts in small intestinal microbiota composition. Relative abundances of all these species decreased after autologous fecal transplantation, but increased after allogenic fecal transplantation. Of note, the relative abundance of *Prevotella* 1 showed a baseline difference between groups (p=0.033). The delta was significantly different between groups for *Prevotella* 2 (p=0.048), but not for *Prevotella* 1 (p=0.069) or *S. oralis*. Furthermore, a significant inverse correlation was observed between *Prevotella* 1 relative abundance and stimulated C-peptide AUC (Spearman p=0.015, rho=−0.55).

Fasting Plasma Metabolite Changes Upon FMT

Fasting plasma metabolite levels were different between DM1 and donors and were altered upon FMT. Treatment group allocation was reliably predicted by change in fasting plasma metabolites between 0 and 12 months (ROC AUC 0.79±0.23). The relative importance of the ten most predictive metabolites are shown in FIG. 2A. From the top 3 metabolites 1-myristoyl-2-arachidonoyl-GPC (MA-GPC) (p=0.02) and 1-arachidonoyl-GPC (A-GPC)(p=0.02, Mann-Whitney U test), but not 1-(1-enyl-palmitoyl)-2-linoleoyl-GPE (EPL-GPE), were different between groups at 12 months (FIGS. 2B-2D). Also, changes in plasma MA-GPC levels correlated significantly with changes in fasting C-peptide (p=0.012, Mann-Whitney U test, FIG. 2E).

Fecal Microbiota Changes Upon FMT

Figure 3:
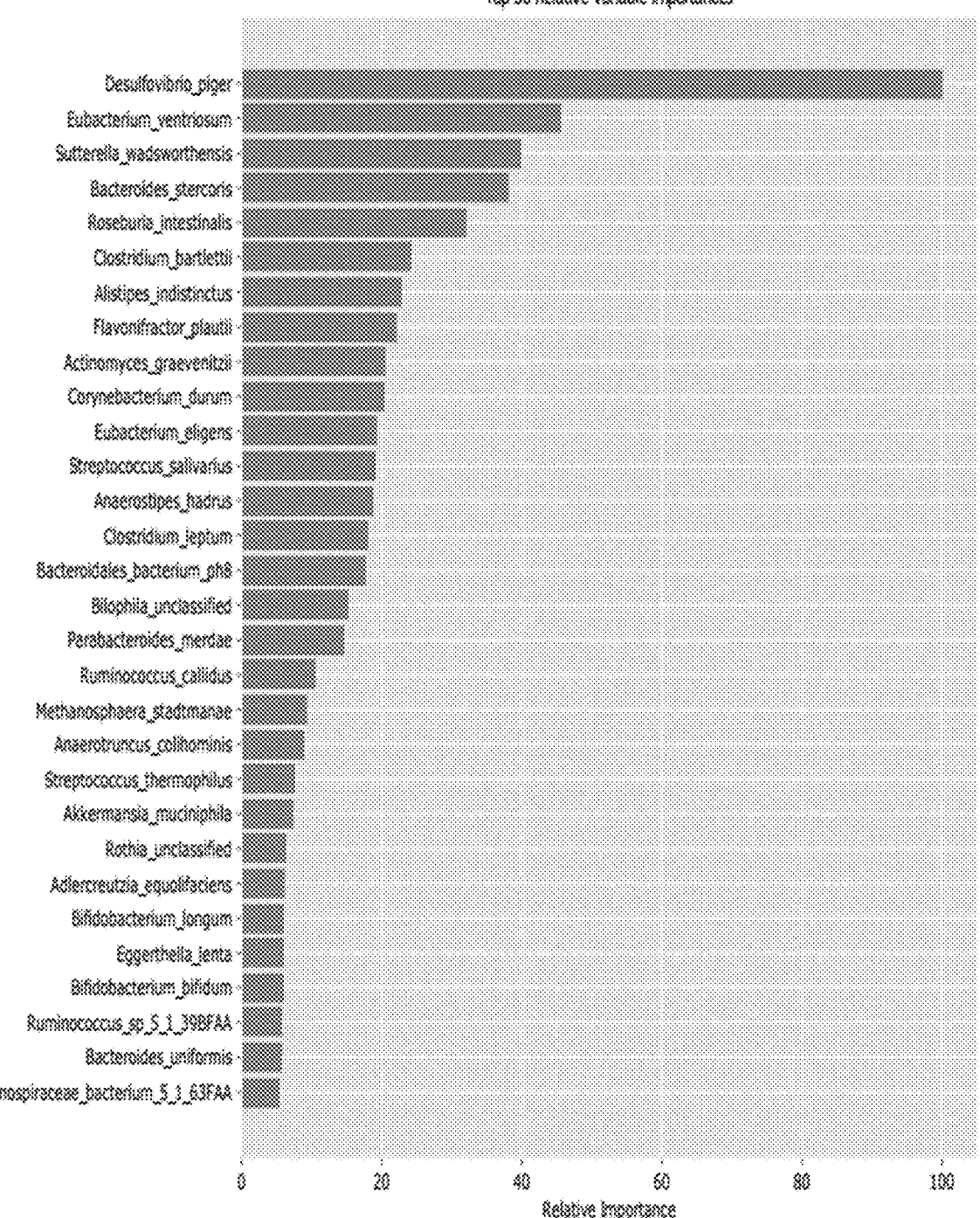
FIG. 3: Predictive modeling output showing top 30 differentially changed fecal microbiota between treatment groups.

Fecal microbiota composition was different between Dm1 and healthy donors at baseline and also changed differentially between treatment groups. However, alpha diversity did not differ significantly between FMT treatment groups at baseline, 6 or 12 months nor between donors and recipients. Some shifts were seen on phylum, family, genus and species level between groups. Group allocation prediction based on fecal microbiota taxonomic changes between 0 and 12 months showed a moderate ROC AUC of 0.72±0.24. *Desulfovibrio piger* stood out as the most differentiating bacterial strain between treatment groups (FIG. 3). Treatment group prediction based on metabolic pathways showed a relatively poor ROC AUC of 0.68±0.27. Interestingly, abundance of *D. piger* changed differentially between treatment groups at 6 (p=0.024, MWU) and 12 (p=0.023) months follow-up (FIGS. 2G and 2H). Furthermore, change in *D. piger* correlates positively with change in fasting C-peptide (p=0.009, FIG. 2I) and with plasma 1-arachidonoyl-GPC levels (p=0.004, FIG. 2J). Moreover, a change in relative abundance of *D. piger* was inversely correlated with changes in relative abundance of both *Prevotella* 1 (FIG. 2K) and *Prevotella* 2 (FIG. 2L). Furthermore, change in *D. piger* correlates positively with change in fasting C-peptide (p=0.009, FIG. 2I) and with plasma 1-arachidonoyl-GPC levels (p=0.004, FIG. 2J). Moreover, change in relative abundance of *D. piger* was inversely correlated with change in relative abundance of both *Prevotella* 1 (FIG. 2K) and *Prevotella* 2 (FIG. 2L).

Baseline Fecal Microbiota Composition Predicts FMT Response.

Figures 4A, 4B:
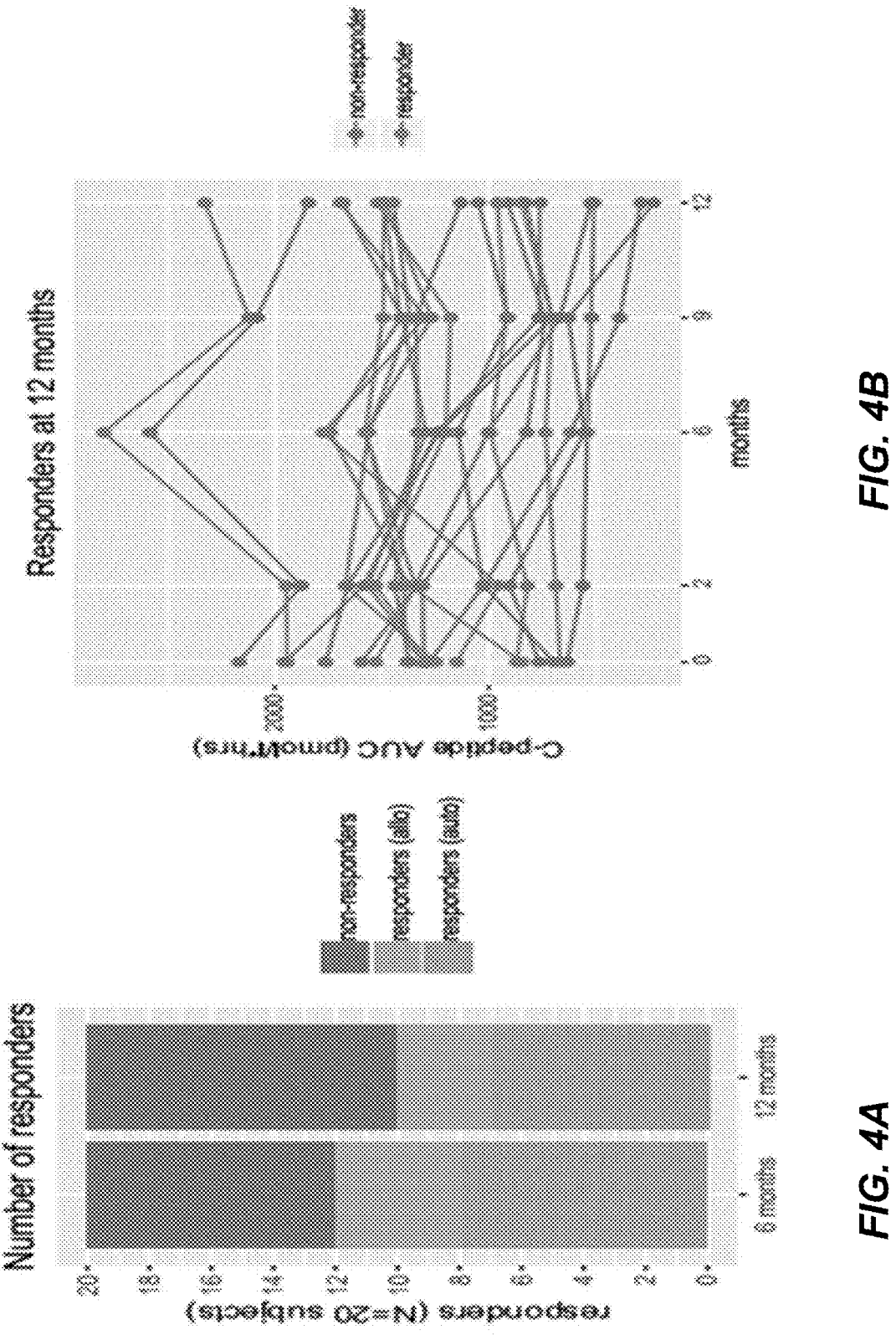
FIGS. 4A-4E.

As gut microbiota composition was different between healthy and T1D subjects in various age groups, it was also reasoned that FMT per se is an intervention in autoimmune diseases, as FMT introduces fecal material in the small intestine. Thus, a post hoc analysis was performed studying responders compared to non-responders to FMT, irrespective of treatment group. It was thus investigated whether baseline characteristics of T1D patients can predict response to FMT therapy at 12 months follow-up and which bacterial strains and plasma metabolites were associated with this response. Clinical response was defined as <10% decline in beta cell function compared to baseline at 12 months follow-up, which is significantly less than the expected natural 1-year decline of 20% in beta cell function. At 6 months follow-up, 2 months after the final FMT, 12/20 subjects were responders. At 12 months follow-up, clinical response sustained in 10 subjects of whom 3 had received allogenic and 7 had received autologous FMT (FIGS. 4A and 4B). Responders at 12 months were thus chosen for the analyses because the primary end point (MMT stimulated C-peptide) was significantly different at 12 (but not at 6) months and because interference by the honeymoon phase is less at the 12 vs 6 months time point. Predictive modeling was next used to determine which baseline parameters (either their baseline values or delta 0-12 month values) were predictors of clinical response to FMT.

Baseline Fecal Microbiota Composition Best Predicts Clinical Response Upon FMT

Figures 4C, 4D, 4E:
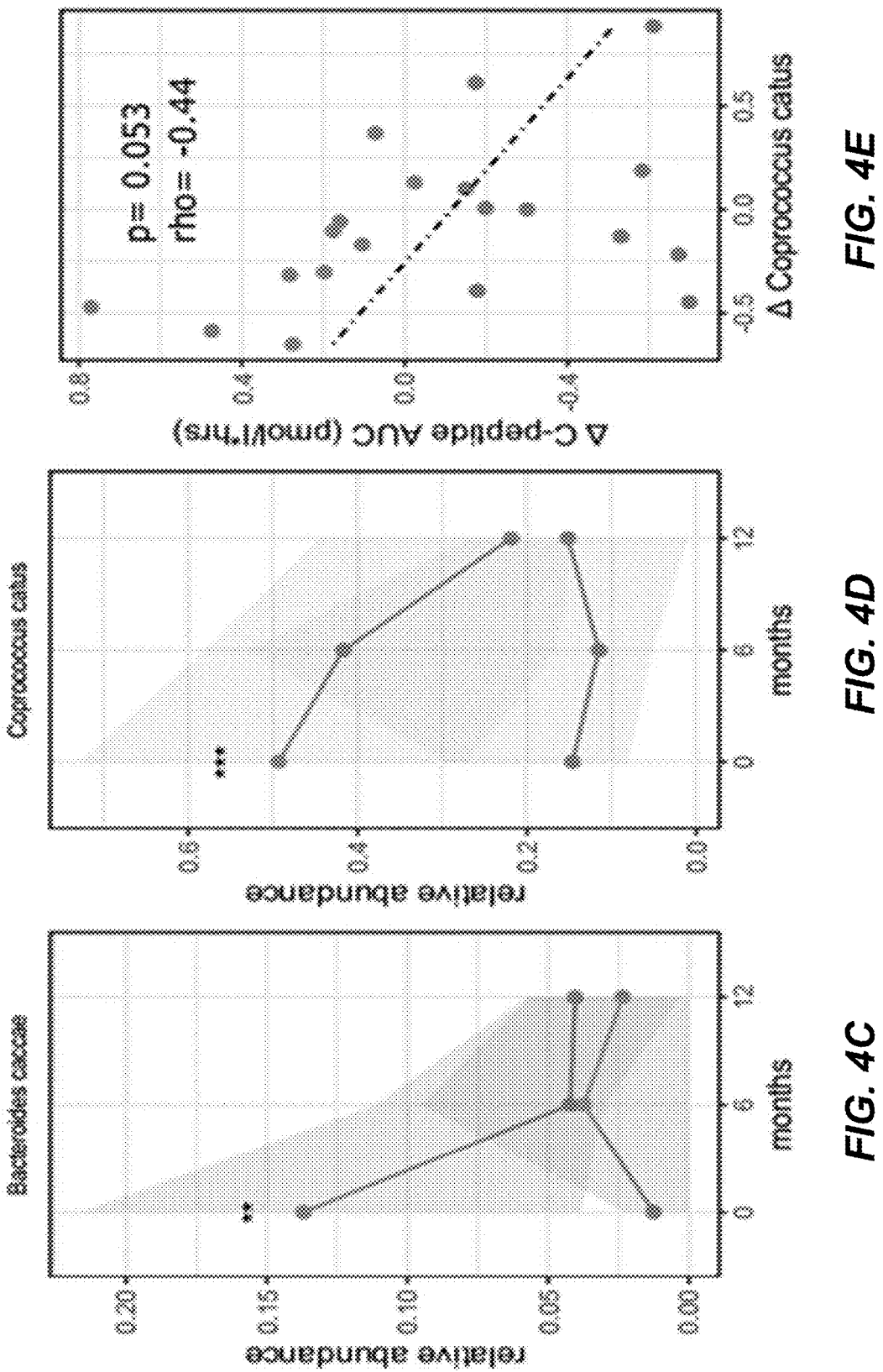
Figure 5:
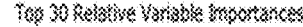
FIG. 5: Predictive modeling output showing top 30 differentially changed fecal microbiota between treatment groups.
Figures 6A, 6B, 6C:
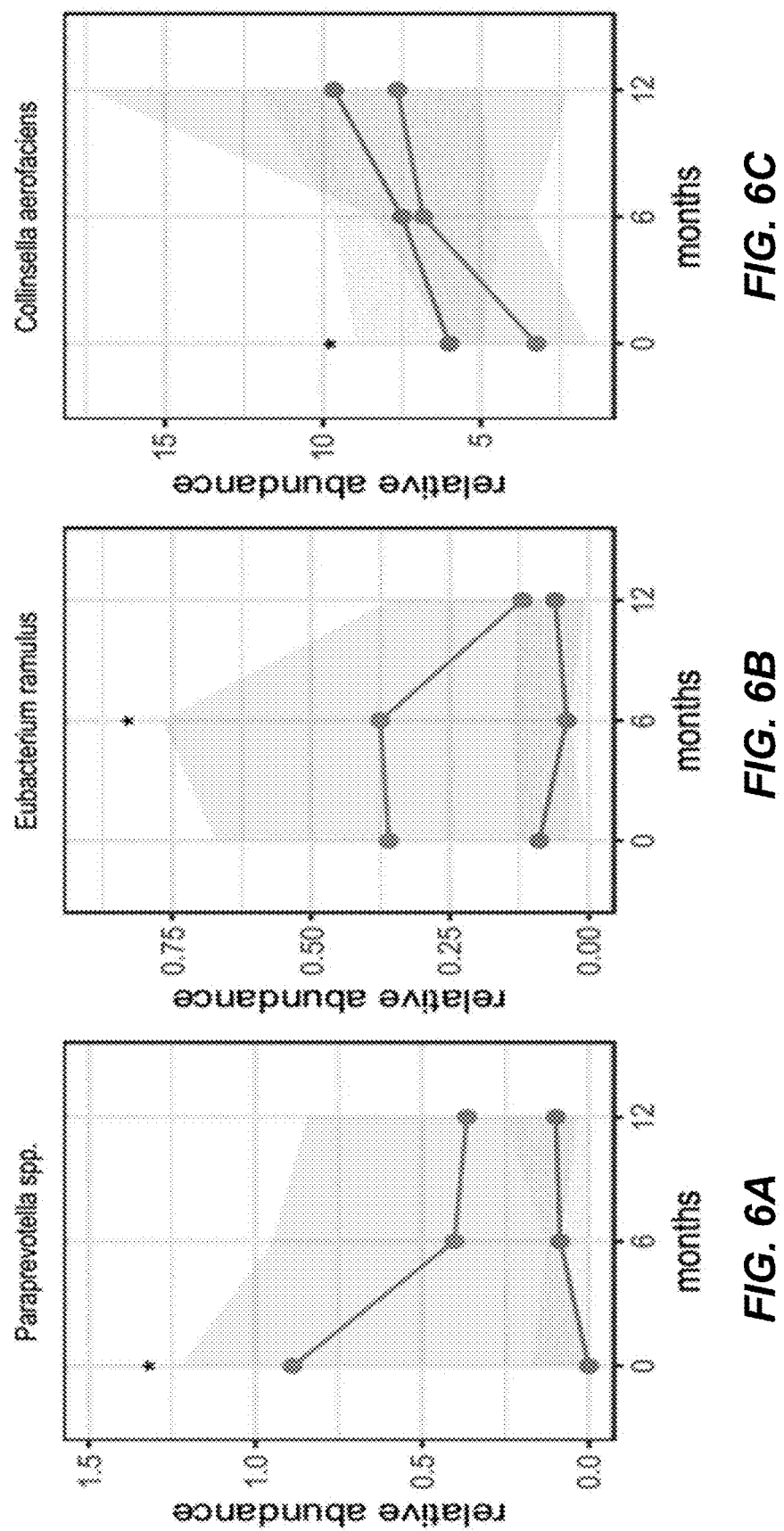
FIGS. 6A-6E: Abundance over time of five fecal microbiota from the top 10 (see FIG. 3) that at baseline best differentiated between responders and non-responders (in FIGS. 6A, 6B, and 6D, the upper line represents responders, the other line non-responders.
Figures 6D, 6E:
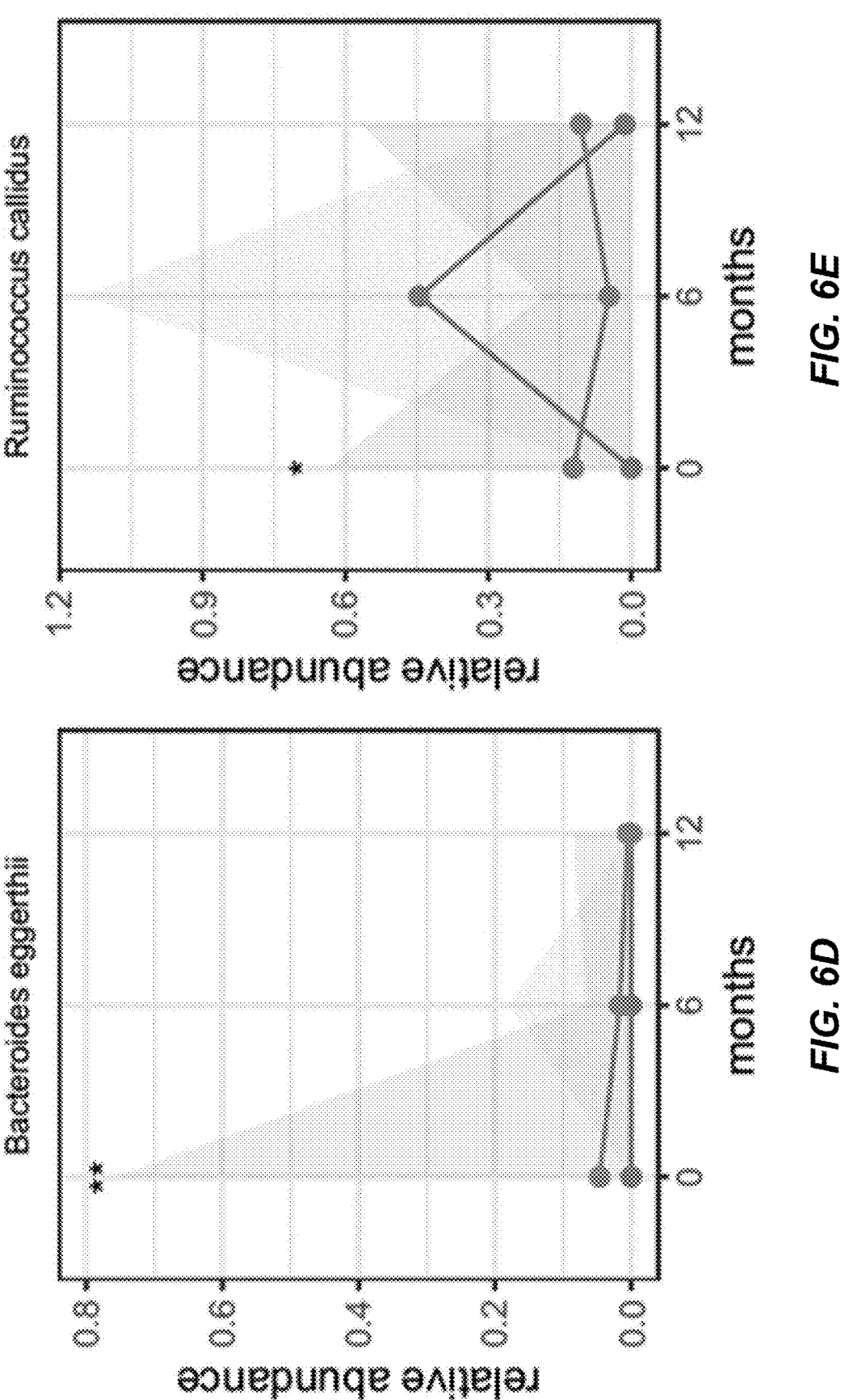

Baseline fecal microbiota composition predicted clinical response upon FMT very accurately (AUC ROC 0.93±0.14). In this regard, intestinal levels of *Bacteroides* caccae and *Coprococcus catus* stood out as most differentiating microbes (FIG. 5), both of which were significantly more abundant at baseline in responders than in non-responders (FIGS. 4C and 4D). From the top 10 most differentiating intestinal bacterial strains, *Paraprevotella* spp, *Collinsella aerofaciens, Bacteroides eggerthii* and *Ruminococcus callidus* were also significantly different at baseline between responders and non-responders (FIGS. 6A-6E). A significant (negative) correlation was observed between change in *C. catus* abundance and stimulated C-peptide AUC (p=0.053, r=−0.44, FIG. 4E). Response was predicted less accurately by change in fecal microbiota composition (AUC ROC 0.76±0.23) than by baseline composition suggesting that at T1D diagnosis gut microbiota composition can predict gut microbiota based treatment efficacy. The most differentiating species were Bacteroidales *bacterium* ph8, *Actinomyces viscosus, Bacteroides thetaoitaomicron, Streptococcus salivarius, Ruminococcus* bromii and *Clostridium leptum*, of which B. *bacterium* ph8 (p=0.015, Mann-Whitney U test) and *R. bromii* (p=0.013) become less abundant in responders vs non-responders, *S. salivarius* (p=0.045) becomes more abundant in responders vs non-responders and *B. thetaiotaomicron* is significantly different at baseline and shows a downward trend in responders.

Integration of Multiomics Analyses Upon FMT

Correlations between parameters that were found to be significantly affected by FMT were explored. Since responders were found in both treatment groups, correlations were first explored in the pooled dataset (n=20) and then within treatment groups separately and in clinical responders upon FMT. In the pooled dataset an intertwined cluster of notable parameters was found, which positively and negatively associated with markers of glucose regulation (i.e., C-peptide AUC, fasting C-peptide and HbA1c). On one hand, the highly correlated plasma metabolites MA-GPC and A-GPC accurately predicting preservation of insulin secretion, correlate positively to *D. piger*, which correlates positively to fasting C-peptide. On the other hand, *Prevotella* 1, *Prevotella* 2 and *S. oralis* correlate negatively to glucose regulation and with metabolites MC-GPC and A-GPC. Analyzing treatment groups separately, preserved beta cell function (high C-peptide) in the autologous group was characterized at baseline by high *Coprococcus catus*, as well as a subsequent decrease in *Ruminococcus* bromii. In the allogenic group, preserved beta cell function was characterized by a decrease in fecal *Roseburia intestinalis* (which incidentally correlates positively with *Prevotella* 1 and 2). Finally, in clinical responders, preserved beta cell function was characterized by decreases in duodenal *Prevotella* 1, *Prevotella* 2, fecal *Coprococcus catus*, metabolite EPL-GPE, whereas *D. piger* increased.

Analysis

It is reported here for the first time that FMT can have an effect on residual beta cell function in new onset T1D patients. This accords with recent observational studies supporting a role for the intestinal microbiota in T1D subjects. Contrary to expectations, autologous FMT performed better than healthy donor FMT, while even in the allogenic group the decline in residual beta cell function appeared less than expected without treatment. An appealing explanation would be that beneficial immunological effects of FMT are more pronounced and durable, when the FMT donor microbiota better matches the immunological tone of the host. This to the extent that beneficial effects of healthy donor stool may be dampened by (immuno)incompatibility. Other observations also point toward an immunological regulatory role of specific plasma metabolites that are derived from diet and converted by intestinal microbiota. While the overall clinical effects of FMT were modest and show a wide variety between new onset T1D subjects, the intervention was safe and had no side effects. It is proposed that changes in plasma metabolites, predominantly fatty acids and tryptophan derivatives, as a consequence of the altered intestinal microbiota composition, may explain the observed beneficial effects of FMT on residual beta cell function in patients with new onset T1D.

Preservation of beta cell function is associated with changes in specific gut microbiota strains.

*D. piger* may dampens autoimmunity in T1D via plasma 1-arachidonoyl-GPC. Predictive modeling showed that baseline fecal microbiota taxonomy and metabolic pathways accurately predicted response at 12 months. However, the identified microbes (e.g., *B. caccae* and *C. catus*) did not correlate with any of the relevant immune parameters, small intestinal genes or plasma metabolites. This suggests that fecal microbiota composition is consequence rather than cause of the host immunological characteristics that associate with response. The exception to this was *D. piger*, a sulfate-reducing bacterial strain. Its beneficial effects may be mediated by its production of hydrogen sulfide. Moreover, *D. piger* was identified as outstanding fecal microbial predictor of FMT treatment group allocation. Interestingly, this small intestinal bacterial strain was also beneficially associated with change in stimulated C-peptide responses upon FMT and its abundance increased in the autologous group and in the overall responders. Interestingly, *D. piger* correlated positively with levels of plasma 1-arachidonoyl-GPC (FIG. 2J), one of the key metabolites that also associated with improved C-peptide production. In conclusion, *D. piger* could be a strong candidate to dampen autoimmunity through production of A-GPC, e.g., through uptake by protruding dendrites of immune cells into the intestinal lumen. Interestingly, *D. piger* was recently cultured from the human intestinal tract, enabling testing this bacterial strain in human T1D (Chen et al. 2019, Letters in Applied Microbiology 68(6) 553-561). Other bacterial species in the duodenum that best differentiated between treatment groups were two unnamed *Prevotella* spp. and *Streptococcus oralis*. The explorative integration of multiomics analyses subsequently show that these *Prevotella* spp. and *S. oralis* are negatively associated with the key beneficial metabolite MA-GPC, a glycerophospholipid. *B. stercoris* correlated positively with *D. piger* and A-GPC and negatively with *S. oralis*, but did not correlate positively with C-peptide. Finally, changes in *Ruminococcus* bromii (autologous FMT group) and *Roseburia intestinalis* (allogenic FMT group) were negatively associated with changes in C-peptide, although both strains are generally regarded as beneficial microbes that thrive during fiber-rich diets, produce SCFA's and promote intestinal integrity.

CONCLUSIONS

Fecal transplantation of colon-derived microbiome into the host small and large intestine in T1D patients effectively prolongs residual beta cell function and thus honeymoon phase. Moreover, several novel bacterial strains including fecal *D. piger* and *B. stercoris* as well as duodenal *Prevotella* spp. and *S. oralis* were identified with therapeutic potential. Accordingly, increases in plasma metabolites such as 1-myristoyl-2-arachidonoyl-GPC, 1-arachidonoyl-GPC, and 6-bromotryptophan upon FMT associated with beneficial changes.

Example 3

In this Example, the effects of the following compounds were assessed in cell-based assays:

6-bromotryptophan (6-BT)

1-arachidonoyl-glycero-phosphocholine (20:0) (A-GPC)

1-palmitoyl-2-linoleoyl-sn-glycero-3-phosphoethanolamine (16:0-18:2 PE)

1-myristoyl-2-arachidonoyl-glycero-phosphocholine (MA-GPC)

Materials and Methods

Metabolite Preparation and Cell Culture 6-bromotryptophan (6-BT) (Alichem) was purchased as powder and dissolved in DMSO at 50 mM.

1-arachidonoyl-glycero-phosphocholine (20:0) LysoPC (20:0) (Avanti Polar) was purchased as powder and was dissolved in PBS at 0.9 mM.

1-palmitoyl-2-linoleoyl-sn-glycero-3-phosphoethanolamine (16:0-18:2 PE) (Avanti Polar) was purchased in chloroform at 10 mg/ml; 200 µl (equivalent to 2 mg) were transferred to a glass tube and chloroform was evaporated under nitrogen flow to obtain a transparent film, which was afterwards dissolved in PBS at 1 mM.

1-myristoyl-2-arachidonoyl-glycero-phosphocholine (MA-GPC) (Syncom, custom made synthesized) was purchased as powder and dissolved in DMSO at 10 mM.

All cell-types were cultured at 37° C. in a 5% CO2 atmosphere and treated with the metabolites for no longer than 24 hours, in control condition the appropriate vehicle (DMSO or PBS) was added in the medium.

NF-κB Reporter Macrophage and Luciferase Assay

NF-κB signaling activation was assessed by luciferase activity assay. RAW264.7 cells stably transfected with the 3×-κB-luc plasmid (DNA construct containing three NF-κB sites from the Ig κ light chain promoter coupled to the gene encoding firefly luciferase) were grown in DMEM medium supplemented with 10% heat-inactivated fetal bovine serum, penicillin (100 U/ml), streptomycin (100 µg/ml), L-glutamine (2 mM). Cells were seeded in F-bottom 96-well plates at a density of 0.5×10⁵ per well and the following day stimulated with LPS (10/100 ng/ml) for 2 hours with/ without addition of metabolites at different concentrations (6-BT 0,1-100 µM, LysoPC(20:0) 1-10 µM, 16:0-18:2 PE 1-50 µM, MA-GPC 1-100 µM). Afterwards, cells were lysed with 25 µl/well 1×passive lysis buffer and firefly luciferase activity was measured by LUCIFERASE® Assay System (Promega, E1500) on a GLOMAX @-Multi Detection System (Promega).

In Vitro Stimulation of Primary Monocytes

Naïve bone marrow monocytes were isolated from BM cells. Briefly, hind legs were removed from 3 mice, cleaned from surrounding muscles. The femur and tibia bones were trimmed at their extremities, the BM content was flushed out with cold PBS using a 10 ml syringe and a 25G needle and filtered through a 40 µm strainer. Red blood cells (RBC) were lysed with 1× RBC lysis buffer (Biolegend) for 5 min. on ice. CD11b+ monocytes were further purified by positive selection using a cocktail of CD11 b magnetic beads (Miltenyi Biotec, #130-049-601) and magnetizing MS columns (Miltenyi Biote) according to the manufacturer's instructions. Subsequently, monocytes were seeded in F-bottom 96-well plates at 1×10⁵ cells per well in RPMI1640 supplemented with 10% heat-inactivated fetal bovine serum, penicillin (100 U/ml), streptomycin (100 µg/ml), L-glutamine (2 mM) and activated with 10 µg/ml poly(I:C). Monocytes were activated with 10 µg/ml LPS (Sigma-Aldrich) and subjected to treatment with 6-BT (10/100 µM), LysoPC(20: 0) (10/50 µM), MA-GPC (10/50/100 µM), or appropriate vehicle. Cells were kept in a final volume of 200 µl/well for 24 hours, after which supernatant was harvested and stored at −80° C.

In Vitro Stimulation of Murine Macrophages/Dendritic Cells (DC)

Bone marrow-derived macrophages (BMDM) and DC (BMDC) were obtained by differentiating freshly isolated BM cells from femur and tibia bones (as above described) of C57/B16 mice (N=3 per experiment). For BMDM, BM cells were seeded at 3×10⁶ cells per 10 cm dish and cultured for 7 days in 12 ml RPMI1640 medium with 20% fetal bovine serum, 30% L-929 cell conditioned media, as source of murine macrophage colony-stimulating factor (M-CSF). For BMDC, BM cells were seeded at 0.5×10⁶/ml cells in 25 ml in 10 cm dishes and cultured for 7 days in presence of GM-CSF in 5% FBS-RPMI1640 medium. After differentiation, BMDM/DCs were harvested, counted and seeded at a density of 1×10⁵ cells per well in a F-bottom 96-well plate and left to adhere for 20 hours before experiments were performed. Macrophages were activated with 10 µg/ml polyinosinic-polycytidylic acid poly(I.C) (InvivoGen) for 24 hours in presence or not of 6-BT (10/100 µM), LysoPC (20:0) (10/50 µM), or MA-GPC (10/50/100 µM) in a final volume of 200 µl/well. At the end of the assay, supernatant was harvested and stored at −80° C.

In Vitro CD4+ T Cell Activation Assay

Primary CD4+ T cells were freshly isolated by negative selection from spleens of C57/B16 mice (N=3 per experiment). Briefly, spleens were smashed in a culture dish and passed twice through a strainer (70 µm and 40 µm, respectively) to obtain a single-cell suspension. After red blood cell lysis (10 min. on ice) with 1× RBC lysis buffer (Biolegend), cells were counted, stained with a cocktail of biotin-conjugated antibodies against CD8a, CD11b, CD11c, CD19, CD45R (B220), CD49b (DX5), CD105, Anti-MHC-class II, Ter-119 and TCRγ/δ and subsequently stained with magnetically labeled with Anti-Biotin MicroBeads.

Using the negative selection (CD4+ T Cell Isolation kit, Miltenyi Biotec, #130-10-454). Non-CD4 T cells were depleted by retaining them in LS magnetizing column (Miltenyi Biotec).

Isolated CD4 T cells were cultured in 96-well plates (1×10⁵ per well) in RPMI1640 medium supplemented with 10% fetal bovine serum, 100 U/ml penicillin, 100 µg/ml streptomycin, 2 mM L-glutamine. Treatment with the metabolites 6-BT (1/10 µM), LysoPC(20:0) (10/50 µM) or MA-GPC (10/50/100 µM) and activation with 2.5 µg/ml soluble anti-CD3 (145-2C11, eBioscience) and 1 µg/ml soluble anti-CD28 (37.51, eBioscience) antibodies started immediately after seeding in 200 i/well complete RPMI1640 media for a 24-hour period, at the end of which supernatant was harvested and stored at −80° C.

In Vitro Stimulation of Human Monocytes

The mononuclear cell fraction was isolated from the blood of healthy volunteers (Sanquin Bloodbank, Amsterdam, The Netherlands) by density centrifugation using Lymphoprep™ (Axis-Shield) and isolated using human CD14 magnetic beads and MACS® cell separation columns (Miltenyi Biotec) according to the manufacturer's instructions. Isolated primary human monocytes were counted and seeded at $1>10^6$ cells/mL in 24-well plates with 1 ml medium supplemented with 10% fetal bovine serum, 100 U/ml penicillin, 100 μg/ml streptomycin, 2 mM L-glutamine. After seeding, cells were stimulated with 10 ng/ml LPS or 25 mM D-glucose (both Sigma-Aldrich) for 24 hours with/without 100 μM 6-BT. Afterwards, cells were lysed with Tripure isolation reagent (Roche) and stored at −80° C. until RNA isolation.

In Vitro Stimulation of Pancreatic Beta Cells

INS1E cells (rat pancreatic beta-cell line) were maintained in complete RPMI1640 supplemented with 5% Fetal Bovine Serum, 2 mM L-glutamine, 5 μM beta-mercaptoethanol, 1 mM sodium pyruvate, 10 mM HEPES, 100 units/ml of penicillin and 100 μg/ml streptomycin. INS1E cells were seeded in 48-well plates at a density of $1 \times 10^5$ cells per well and left resting for one day. Subsequently, medium was replaced with 0.5 ml/well of INS1E complete RPMI1640 medium containing vehicle or the metabolites: 6-BT (1/10/25 μM), LysoPC(20:0) (5/10/50 μM), or MA-GPC (10/50/100 μM). After 24 hours, cells and supernatant were harvested for further analysis (gene expression and insulin secretion, respectively) and stored at −80° C. Cells were lysed in Tripure isolation reagent (Roche) before storage.

For glucose-stimulated insulin secretion (GSIS) assay, cells were preincubated in a Krebs-Ringer bicarbonate buffer (KRB) [115 mM NaCl, 5 mM KCl, 2.56 mM $CaCl_2$), 1 mM $MgCl_2$, 10 mM $NaHCO_3$, 15 mM HEPES, and 0.3% of BSA (pH 7.4)] for 30 min at 37° C., following by stimulation with 1 mM glucose in KRB for 1 hour (0.5 ml/well) and stimulation with 22 mM glucose in KRB for another hour (0.5 ml/well) at 37° C. Supernatant was recovered after treatment with 1 mM glucose (Sigma-Aldrich) and 22 mM glucose and cells stored at −80° C. GSIS was performed on beta cells after treatment for 24-hour treatment with 10 μM 6-BT.

ELISA

Specific ELISAs (R&D Systems) were utilized to measure the concentration of TNFα, IFNβ, and IFNγ in cell supernatant of murine monocytes, macrophages ad T cells, respectively, according to the manufacturer's instructions. The concentration of insulin after 24-hour treatment with metabolites or after GSIS were determined using Rat insulin ELISA (Mercodia) according to the manufacturer's instructions. GSIS was calculated by subtracting the concentration of insulin at 1 mM glucose to the insulin rate at 22 mM glucose.

Gene Expression Analysis

Total RNA was extracted from Tripure isolation reagent cell lysates. RNA was converted to cDNA by with iScript kit (BioRad). Quantitative polymerase chain reaction (qPCR) was performed using SYBR Green-SensiMix (Bioline) on a CFX384 Touch Real-Time PCR Detection System (Bio- Rad). The delta delta Ct method was used to calculate gene expression as fold-change compared to control (unstimulated conditions).

Statistics

Statistical analysis was performed using Student t tests for two group comparison and One-Way ANOVA and Dunnett's tests for multiple group comparison. Data are presented as mean and standard error of the mean (SEM). P<0.05 was considered to be significant.

Results

The results are shown in FIGS. 7-13:

6-BT, A-GPC, and MA-GPC can inhibit NFκB pathway activation in macrophages at different doses (FIG. 7).

6-BT, A-GPC, and MA-GPC halt cytokine secretion by monocytes (FIG. 8);

6-BT and MA-GPC impair type 1 IFN secretion (FIG. 9);

6-BT reduces cytokine production by human monocytes (FIG. 10);

6-BT and A-GPC dampen Th1 responses in CD4 T cells (FIG. 11);

6-BT enhances pancreatic beta-cell function (FIGS. 12 and 13);

Of specific interest is 6-bromotryptophan, which thus inhibits NFκB pathway activation, hampers immune responses in monocytes/macrophages and CD4 T cells, and improves pancreatic beta cell function. MA-GPC inhibits NFκB pathway activation, hampers immune responses in monocytes/macrophages and CD4 T cells.

Example 4

Plasma 6-Bromotryptophan Levels Inversely Correlate with Presence of Type 2 Diabetes Mellitus and Glycemic Control in Cross-Sectional Cohort (n=369 Subjects)

In a 369-subject cohort, evidence was found that 6-bromotryptophan may protect against the onset and progression of Type 2 Diabetes mellitus. More specifically, it was found that plasma 6-bromotryptophan levels inversely correlate with presence of Type 2 Diabetes mellitus and glycemic control. This suggests that 6-BT may contribute to Type 2 Diabetes prevention and treatment and thus improved (micro and macrovascular) cardiovascular complications in Type 2 Diabetes. 6-BT may help to reduce macrovascular disease (i.e., cardiovascular disease) and microvascular complications also in non Type 2 Diabetes patients.

Materials and Methods

Fasting plasma targeted metabolite measurements were done by Metabolon (Durham, NC), using ultra high performance liquid chromatography coupled to tandem mass spectrometry (UPLC-MS/MS), as previously described [Koh A, Molinaro A, Stahlman M, et al. Microbially Produced Imidazole Propionate Impairs Insulin Signaling through mTORC1. *Cell* 2018; 175:947-961.e17. doi:10.1016/j.cell.2018.09.055].

Results

Results are shown in Tables 2 and 3.

TABLE 2

| Baseline characteristics | | | | | |
| --- | --- | --- | --- | --- | --- |
|  | Total | CKD− T2DM | CKD+ T2DM | Controls | p |
| n | 369 | 124 | 45 | 200 |  |
| Age | 51.72 | 52.13 | 60.24 | 49.55 | <0.001 |
| (mean (SD)) | (11.27) | (10.98) | (6.04) | (11.44) |  |
| Sex = 2 (%) | 196 | 68 | 19 | 109 | 0.294 |
|  | (53.1) | (54.8) | (42.2) | (54.5) |  |

TABLE 2-continued

Baseline characteristics

| | Total | CKD−T2DM | CKD+T2DM | Controls | p |
|---|---|---|---|---|---|
| Ethnicity (%) | | | | | <0.001 |
| Dutch | 84 (22.8) | 34 (27.4) | 0 (0.0) | 50 (25.0) | |
| South Asian | 101 | 24 | 27 | 50 | |
| Surinamese | (27.4) | (19.4) | (60.0) | (25.0) | |
| African | 105 | 37 | 18 | 50 | |
| Surinamese | (28.5) | (29.8) | (40.0) | (25.0) | |
| Ghanaian | 79 (21.4) | 29 (23.4) | 0 (0.0) | 50 (25.0) | |
| BMI | 27.48 | 28.56 | 30.06 | 26.22 | <0.001 |
| (mean (SD)) | (5.18) | (5.66) | (5.15) | (4.48) | |
| WHR | 0.93 | 0.94 | 1.00 | 0.91 | <0.001 |
| (mean (SD)) | (0.09) | (0.08) | (0.08) | (0.08) | |
| SBP | 136.22 | 141.75 | 148.43 | 130.04 | <0.001 |
| (mean (SD)) | (21.15) | (22.56) | (22.16) | (17.69) | |
| DBP | 83.23 | 86.54 | 83.90 | 81.03 | <0.001 |
| (mean (SD)) | (11.52) | (13.29) | (9.42) | (10.24) | |
| HT (%) | 215 | 87 | 39 | 89 | <0.001 |
| | (58.3) | (70.2) | (86.7) | (44.5) | |
| AntiHT (%) | 107 | 39 | 28 | 40 | <0.001 |
| | (29.0) | (31.5) | (62.2) | (20.0) | |
| MDRD | 96.03 | 94.19 | 89.81 | 98.58 | 0.024 |
| (mean (SD)) | (21.56) | (21.34) | (28.91) | (19.38) | |
| CKDEPI | 94.99 | 93.29 | 84.31 | 98.46 | <0.001 |
| (mean (SD)) | (19.49) | (20.02) | (23.43) | (17.13) | |
| Microalb | 0.44 | 0.92 | 0.96 | 0.02 | <0.001 |
| (mean (SD)) | (0.50) | (0.27) | (0.21) | (0.16) | |
| HbA1C | 40.73 | 39.52 | 58.16 | 37.56 | <0.001 |
| (mean (SD)) | (9.58) | (4.64) | (15.74) | (4.62) | |
| Kreat | 78.67 | 80.17 | 86.82 | 75.90 | 0.006 |
| (mean (SD)) | (21.61) | (22.23) | (36.63) | (15.42) | |

TABLE 3

Correlations between compounds and presence of
Diabetes, BMI value, Glucose value, HbA1c value

| | Diabetes | BMI | Glucose | HbA1c | Scale |
|---|---|---|---|---|---|
| 3-indoxyl sulfate | 0.078 | 0.062 | 0.020 | −0.015 | −0.4 |
| 6-bromotryptophan | −0.177 * | −0.069 | −0.062 | −0.179 * | −0.3 |
| C-glycosyltryptophan | 0.336 | 0.177 | 0.192 | 0.28 | −0.2 |
| indoleacetate | 0.061 | −0.033 | −0.019 | 0.024 | −0.1 |
| indolelactate | 0.194 | 0.028 | 0.182 | 0.166 | 0 |
| indolepropionate | −0.141 | −0.157 | −0.117 | −0.125 | 0.1 |
| kynurenate | 0.17 | 0.123 | 0.13 | 0.154 | 0.2 |
| kynurenine | 0.123 | 0.096 | 0.048 | 0.099 | 0.3 |
| tryptophan | −0.100 | 0.011 | −0.016 | −0.052 | 0.4 |
| tryptophan betaine | 0.065 | −0.115 | 0.017 | 0.002 | |
| indoleacetoylcarnitine * | 0.052 | 0.011 | −0.041 | −0.021 | |
| N-acetyltryptophan | 0.124 | 0.030 | 0.127 | 0.101 | |
| serotonin | 0.009 | −0.067 | −0.023 | −0.018 | |
| xanthurenate | 0.113 | 0.146 | 0.138 | 0.114 | |

* Correlation is significant at the 0.05 level (2-tailed).

6-bromotryptophan halts inflammatory responses in myeloid cells

6-BT is a bromoindole derivative of tryptophan, which is known to be metabolized by indigenous gut microbes of the colon as well as of small intestine. So far, the physiological role of 6-BT is completely unknown. Clinical findings suggest a protective function against inflammation and diabetes.

With a series of in vitro/ex vivo experiments, some of 6-BT functions on immune cells as well as on insulin-producing pancreatic beta cells were elucidated.

6-BT can inhibit the secretion of proinflammatory cytokine TNFα upon TLR4 and TLR2 engagements and of IFNbeta upon TLR3 activation Here, murine bone marrow-isolated monocytes (Christ A., Western Diet Triggers NLRP3-Dependent Innate Immune Reprogramming. Cell 2018) or bone marrow-derived macrophages (Swanson K V, A noncanonical function of cGAMP in inflammasome priming and activation. JEM 2017) were exposed for 24 hours to the indicated concentrations of 6-BT (10-100 μM) in presence or not of 10 μg/ml LPS, 10 μg/ml P3C or 10 μg/ml poly(I.C). By means of ELISA assays, it has been found that 6-BT can inhibit the secretion of proinflammatory cytokine TNFα upon TLR4 and TLR2 engagements and of IFNbeta upon TLR3 activation. See FIG. 14.

The inhibition of TLR signaling induced cytokine secretion is particularly important for therapeutic approaches against inflammatory and infectious diseases in which the damage is driven by an excessive inflammatory repose (such as sepsis and systemic inflammatory response syndrome, SIRS).

6-BT Inhibits the Secretion of the Proinflammatory Cytokines TNFα and IFNbeta

As dendritic cells (DC) are the major antigen-presenting cells crucial in the activation of T cells, next investigated was the effect of 6-BT on murine DC, differentiated with GM-CSF (40 μg/ml) by bone marrow cells. As for the monocytes/macrophages, 6-BT inhibits the secretion of the proinflammatory cytokines TNFα and IFNbeta by DC after activation of, respectively, TLR4 (with 100 μg/ml LPS) or TLR3 (10 μg/ml poly(I.C)). See FIG. 15.

6-BT Significantly Reduced the Production of the Th1 Cytokine IFNgamma

Particularly in the context of autoimmune diabetes, the activity of T cells is driving disease onset and progression.

Hence, the impact of 6-BT on CD4 T cells was further studied. To mimic antigen presentation, murine CD4 T cells (isolated from spleens; Uchimura T., The Innate Immune Sensor NLRC3 Acts as a Rheostat that Fine-Tunes T Cell Responses in Infection and Autoimmunity. Immunity 2019) were activated by monoclonal antibodies against CD3 and CD28 (2.5 and 1 μg/ml, respectively). In line with the findings on myeloid cells, 6-BT significantly reduced the production of the Th1 cytokine IFNgamma. See FIG. 16.

6-BT Stimulates β-Cells Differentiation & Insulin Production

Given the positive association between plasma 6-BT levels and C-peptide concentrations (found in the clinical study), it was then questioned whether 6-BT can exert a direct effect on beta cells. Indeed, it is seen here that 6-BT induces, in IS1E beta cells, the gene expression of the transcription factors PDX1 and MAFA, which are important for beta cell maturation and functionality. In agreement, 6-BT also promotes insulin secretion at steady-state and during glucose-stimulated insulin secretion (data shown as the difference between insulin release at starving condition [1 mM glucose] and at hyperglycemic state [22 mM]), (Paula S., Exercise increases pancreatic 3-cell viability in a model of type 1 diabetes through IL-6 signaling. FASEB J 2015). See FIG. 17.

Mechanism(s) of Action of 6-Bromotryptophan

Seeking for the molecular mechanism(s) underlying 6-BT actions, 6-BT impact on the activation of the NF-kB pathway, a central pathway in all inflammatory diseases (beyond autoimmunity) was checked first. Hence, the expression of the phosphorylated form of the p65 subunit, regarded as a marker of NFkB activation has been quantified. Upon T cell activation with PMA (50 µg/ml) and ionomycin (1 µg/ml), 6-BT could inhibit, at very early time-points (5-10 minutes after activation), the NF-kB signaling. This effect was found in both murine and human (Jurkat cells) CD4 T cells. See FIG. 18.

6-BT Inhibits the Activation of NFkB in Macrophages

Similarly to what was observed in lymphocytes, 6-BT inhibits the activation of NFkB in macrophages. Using the RAW264.7 murine macrophage cell line stably expressing an NFkB luciferase reporter (Groeneweg M, Lipopolysaccharide-induced gene expression in murine macrophages is enhanced by prior exposure to oxLDL. J. Lipid Res., 2006), it was disclosed that overnight exposure of macrophages to 6-BT (10-200 µM) inhibits the transcriptional activity of the NFkB complex in a dose-dependent manner upon 2 hours stimulation with LPS (10 µg/ml). See FIG. 19.

6-BT and Tryptophan Elicit Distinct Biological Activities

Next, it was questioned whether the effect of 6-BT are specific or can be exerted by tryptophan as well. In murine CD4 T lymphocytes (isolated from murine spleens; Uchimura T., The Innate Immune Sensor NLRC3 Acts as a Rheostat that Fine-Tunes T Cell Responses in Infection and Autoimmunity. Immunity 2019), 6-BT, but not tryptophan, exerted inhibitory effect on IFNgamma production upon CD3/CD28 engagement. This indicates that 6-BT and tryptophan elicit distinct biological activities. See FIG. 20.

In agreement with the results on DC, exposure of monocytes (isolated from murine bone marrow; Christ A., Western Diet Triggers NLRP3-Dependent Innate Immune Reprogramming. Cell 2018) to 6-BT or tryptophan, shows that the anti-inflammatory effects are specific for the 6-bromotryptophan molecule and not for tryptophan. See FIG. 2I.

6-BT Impacts the Intracellular Metabolism

Finally, it was uncovered that 6-BT also impacts the intracellular metabolism. Particularly it was found that 6-BT (100 uM) promotes the mitochondrial metabolism in murine and human (Jurkat) CD4 T cells. See FIG. 22.

OCR=oxygen consumption rate, used as a proxy of cellular utilization of mitochondrial oxidative phosphorylation. OCR was measured using a Seahorse XF Analyzer Uchimura T., The Innate Immune Sensor NLRC3 Acts as a Rheostat that Fine-Tunes T Cell Responses in Infection and Autoimmunity. Immunity 2019; Chou, AIM2 in regulatory T cells restrains autoimmune diseases, Nature 2021.

6-BT Enhances Mitochondrial Metabolism

Similarly, 6-BT exposure could enhance the mitochondrial metabolism of pro-inflammatory M1 macrophages (differentiated in presence of LPS and IFNgamma; Cheng et al., JCI Insight. 2018; 3(22):e120638), without affecting the glycolytic flux. Intracellular metabolism measured using a Seahorse XF Analyzer, Uchimura T., The Innate Immune Sensor NLRC3 Acts as a Rheostat that Fine-Tunes T Cell Responses in Infection and Autoimmunity. Immunity 2019; Chou, AIM2 in regulatory T cells restrains autoimmune diseases, nature 2021. See FIG. 23.

6-BT could Rescue Beta Cell Dysfunctionality in Both Type 1 and Type 2 Diabetes

Lastly, it was investigated whether 6-BT may influence the mitochondrial metabolism of beta cells, which rely on ATP and mitochondrial metabolite production for insulin exocytosis. 6-BT increased mitochondria metabolism both at steady-state and under hyperglycemia (25 mM glucose) in beta cells (INS1E beta cells). In addition, the effect of tryptophan on intracellular metabolism was tested and it was found that, as for the inflammatory markers, it exerted a different effect than 6-BT. Intracellular metabolism measured using a Seahorse XF Analyzer Uchimura T., The Innate Immune Sensor NLRC3 Acts as a Rheostat that Fine-Tunes T Cell Responses in Infection and Autoimmunity. Immunity 2019; Chou, AIM2 in regulatory T cells restrains autoimmune diseases, nature 2021.

Of importance, defects in mitochondria and oxidative metabolism have been reported in T2D (Haythorne, Nature Communications volume 10, Article number: 2474 (2019)), suggesting that 6-BT could rescue beta cell dysfunctionality in both type 1 and type 2 diabetes. Moreover, increase utilization of mitochondria metabolism may counteract ectopic intracellular lipid accumulation and hence counteract obesity.

In conclusion:

6-BT exerts pleiotropic effect on multiple cell-types

It has anti-inflammatory effect on myeloid and lymphoid cells

It promotes insulin secretion by beta cells

Mechanistically, its biological actions are distinct from the ones of tryptophan.

6-BT does not act through activation of AhR, but it does inhibit NFkB activation and enhance mitochondrial metabolism. The latter is typically used by cells harboring an anti-inflammatory phenotype.

Applications

Because of its broad effects on multiple cell types, its inhibitory action on NFkB signaling and its promotion of mitochondrial metabolism and fitness, 6-BT may be a novel therapeutic not only in the context of type 1 and type 2 diabetes but also in many other inflammation related disorders such as sepsis, Systemic Inflammatory Response Syndrome (SIRS), and cardiovascular diseases.

Example 5

*Desulfovibrio* genus levels inversely correlate with presence of Type 2 Diabetes mellitus and glycemic control in cross-sectional cohort (n=369 subjects)

In the same 369-subject cohort as discussed herein previously, evidence was found that bacteria belonging to the *Desulfovibrio* genus (e.g., *Desulfovibrio piger*) may protect against the onset and progression of Type 2 Diabetes mellitus. More specifically, it was found that the relative abundance of fecal bacteria belonging to the *Desulfovibrio* genus inversely correlates with presence of Type 2 Diabetes mellitus and glycemic control. This suggests that administration of *Desulfovibrio* genus may contribute to Type 2 Diabetes prevention and treatment and thus improved (micro and macrovascular) cardiovascular complications in Type 2 Diabetes. *Desulfovibrio* genus may help to reduce macrovascular disease (i.e., cardiovascular disease) and microvascular complications also in non-Type 2 Diabetes patients.

Materials and Methods

Fasting plasma targeted metabolite measurements were done by Metabolon (Durham, NC), using ultra high performance liquid chromatography coupled to tandem mass spectrometry (UPLC-MS/MS), as previously described [Koh A., Molinaro A., Stahlman M., et al., Microbially Produced Imidazole Propionate Impairs Insulin Signaling through mTORC1. *Cell* 2018; 175:947-961.e17. doi:10.1016/j.cell.2018.09.055].

Results

Results are shown in Table 4 and in FIGS. 25 and 26.

TABLE 4

| Correlations between fecal *Desulfovibrio* genus relative abundance and presence of Diabetes, BMI value, Glucose value, HbA1c value | | | | |
| --- | --- | --- | --- | --- |
| | Diabetes | BMI | Glucose | HbA1c |
| *Desulfovibrio* genus | −0.03* | −0.03* | 0.02 | −0.02 |

*Correlation is significant at the 0.05 level (2-tailed).

In addition, in type 2 Diabetes mellitus patients, a clear relationship can be seen between fecal *Desulfovibrio* relative abundance and plasma 6BT levels. See FIG. 27.

The invention claimed is:

1. A method of treating a subject for diabetes mellitus, the method comprising:

administering to the subject an amount of 6-bromotryptophan to treat the diabetes mellitus, wherein the 6-bromotryptophan is not comprised in fecal matter.

2. The method according to claim 1, wherein the subject has an elevated inflammatory immune profile, wherein the elevated inflammatory immune profile comprises increased levels of TNFα, IFNβ, IFNγ, or a combination thereof.

3. The method according to claim 2, wherein administration of the 6-bromotryptophan reduces secretion of one or more pro-inflammatory cytokines selected from TNFα, IFNβ, and IFNγ.

* * * * *